US012614607B2

(12) United States Patent
Rackham et al.

(10) Patent No.: US 12,614,607 B2
(45) Date of Patent: Apr. 28, 2026

(54) CELL CULTURE METHODS AND COMPOSITIONS

(71) Applicants:Monash University, Clayton (AU); Mogrify Limited, Cambridge (GB); National University of Singapore, Singapore (SG)

(72) Inventors: Owen Rackham, Singapore (SG); Enrico Petretto, Singapore (SG); Uma Kamaraj, Singapore (SG); Jose Polo, Clayton (AU); Joseph Chen, Clayton (AU)

(73) Assignees: Monash University, Clayton (AU); Mogrify Limited, Cambridge (GB); National University of Singapore, Singapore (SG)

( * ) Notice: Subject to any disclaimer, the term of this patent is extended or adjusted under 35 U.S.C. 154(b) by 881 days.

(21) Appl. No.: 17/622,396

(22) PCT Filed: Jun. 26, 2020

(86) PCT No.: PCT/AU2020/050656
§ 371 (c)(1),
(2) Date: Dec. 23, 2021

(87) PCT Pub. No.: WO2020/257867
PCT Pub. Date: Dec. 30, 2020

(65) Prior Publication Data
US 2023/0024424 A1     Jan. 26, 2023

(30) Foreign Application Priority Data
Jun. 26, 2019     (SG) .......................... 10201905939W

(51) Int. Cl.
G16B 5/00      (2019.01)
C12N 5/071     (2010.01)
G16B 25/10     (2019.01)
(52) U.S. Cl.
CPC ............. G16B 5/00 (2019.02); C12N 5/0602 (2013.01); G16B 25/10 (2019.02); C12N 2506/02 (2013.01)
(58) Field of Classification Search
None
See application file for complete search history.

(56) References Cited

U.S. PATENT DOCUMENTS

2017/0002319 A1     1/2017  D'Alessio et al.

FOREIGN PATENT DOCUMENTS

WO     WO 2020/257867     12/2020

OTHER PUBLICATIONS

Benayoun Berenice et al. H3K4me3 breadth is linked to cell identity and transcriptional consistency. Cell 158, 673-688, Jul. 31, 2014. Elsevier Inc. pp. 673-688. (Year: 2014).*
Benayoun et al., "H3K4me3 breadth is linked to cell identity and transcriptional consistency," Cell, Jul. 31, 2014, 158(3):673-88.
Liu et al., "Distinct features of H3K4me3 and H3K27me3 chromatin domains in pre-implantation embryos," Nature, Sep. 2016, 537(7621):558, 20 pages.
PCT International Search Report and Written Opinion in International Appln. No. PCT/AU2020/050656, dated Sep. 1, 2020, 7 pages.
Wu et al., "Clustering-local-unique-enriched-signals (CLUES) promotes identification of novel regulators of ES cell self-renewal and pluripotency," Plos one, Nov. 2018, 13(11):e0206844, 29 pages.
Xia et al., "Machine learning uncovers cell identity regulator by histone code," Nature Communications, Jun. 1, 2020, 11(1):1-2.
JP Office Action in Japanese Appln. No. 2021-576869, mailed on Jul. 21, 2023, 16 pages (with English translation).
Ouyang et al., "Molecular interaction networks to select factors for cell conversion," Computational Stem Cell Biology: Methods and Protocols, May 2019, 333-61.
Rackham et al., "A predictive computational framework for direct reprogramming between human cell types," Nature Genetics, Mar. 2016, 48(3):331, 8 pages.
JP Office Action in Japanese Appln. No. 2021-576869, mailed on Oct. 30, 2023, 8 pages (with English translation).
Watanabe, "Cell Culture," Dictionary of Biotechnology, DNA Research Institute, Sep. 1990, 165, 5 pages (with English translations).
AU Office Action in Australian Appln. No. 2020308962, mailed on May 29, 2023, 4 pages.
Cahan et al., "CellNet: network biology applied to stem cell engineering," Cell, Aug. 2014, 158(4):903, 24 pages.
CN Office Action in Chinese Appln. No. 202080060399.6, mailed on Aug. 31, 2024, 28 pages (with English translation).
D'Alessio et al., "A systematic approach to identify candidate transcription factors that control cell identity," Stem Cell Reports, Nov. 2015, 5(5):763-75.
EP Extended European Search Report in European Appln. No. 20831995.4, mailed on Nov. 7, 2023, 12 pages.

* cited by examiner

*Primary Examiner* — Nghi V Nguyen
(74) *Attorney, Agent, or Firm* — Fish & Richardson P.C.

(57) ABSTRACT

A method for maintaining a cell in vitro that comprises the steps of: providing a cell of interest in cell culture, determining differential breadth of histone 3 trimethylated at lysine 4 (H3K4me3) modified regions and a differential broadness score for each protein-coding gene in said cell, determining a network score for each protein-coding gene in said cell based on the differential broadness score and interactions between the protein products of each protein-coding gene over at least one network, and determining a cell identity score for each protein-coding gene in said cell based on a combination of the differential broadness score and network scores. The cell identity scores are used to prioritise protein-coding genes thereby identifying cell identity genes for said cell, which encode factors associated with cell identity. The cell of interest is cultured in the presence of said factors, thereby maintaining the cell identity of the cell of interest.

17 Claims, 22 Drawing Sheets

D

E

A

Step 1: Compute Differential Broadness Score (DBS)

DBS = fn (ΔPeak breadth, P-value)

B

Step 2: Compute Regulatory DBS (RegDBS)

Step 3: Predictions ranked by RegDBS:

(i) Cell identity genes (Protein-coding genes)

(ii) Signalling molecules for cell maintenance

Figure 2 continued

D    EpiMogrify: Prediction of signaling molecules for cell maintenance

A

B % of cell conversions (x) with significant enrichment for EpiMogrify predicted TFs

CELL CULTURE METHODS AND COMPOSITIONS

FIELD OF THE INVENTION

The present invention relates to methods for the identification of cell culture factors for cell maintenance and cell conversion.

RELATED APPLICATION

This application is a National Stage application under 35 U.S.C. § 371 of International Application No. PCT/AU2020/050656, filed on Jun. 6, 2020, which claims priority from Singaporean patent application 10201905939W, filed on Jun. 26, 2019, the contents of which are hereby incorporated by reference in their entirety.

BACKGROUND OF THE INVENTION

Since embryonic stem cells were first isolated, the ability to culture and control cell state has been increasing. However, one of the most challenging areas in the field is finding the ideal cell culture conditions for maintaining the cells in vitro. If the correct conditions are not employed then the cells either transform into a different cell state or die. Therefore, there is a critical need to mimic in vivo microenvironment conditions as closely as possible in vitro. To increase the media's specificity to the cell type, the addition of cell-specific factors like components of Extracellular Matrix (ECM), growth factors and other environmental cues are required.

Furthermore, the major challenge in the advancement of cell therapies is the requirement for chemically defined cell culture conditions and efforts are being taken to develop serum-free media for the maintenance of various cell types. Similarly, for differentiation, increasing efforts are being made to determine serum-free chemically-defined protocols to obtain cells for cell therapy. These protocols use external cues like signalling molecules which mimic the natural developmental process; for instance, the differentiation of endothelial cells, microglia and cardiac myocytes. Further, signalling molecules like VEGF have been shown to remodel the epigenetic landscape at the master regulator gene loci in endothelial differentiation. This suggests that signalling molecules can initiate epigenetic regulation to either maintain the cell state or differentiate.

There are more than 400 known human cell types and with recent advances in single-cell sequencing technology, more new cell types are being identified during embryonic development, such as sensory neuron types and blood cell types. Therefore, there is an unmet need to systematically identify cell culture conditions and/or differentiation stimuli for any human cell type. Transcription factor (TF)-mediated transdifferentiation is a well-studied field, and there is a growing number of data-driven computational approaches developed for the prediction of TFs using gene expression data such as CellNet, D'Alessio A C et al. and Mogrify. However, there is currently no computational approach to systematically identify signalling molecules for in vitro cell maintenance or cell conversion across a multitude of cell types.

There is a need for new methods for identifying factors for maintaining cells in culture and for converting cells to different cell types.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present invention provides a method of determining the cell identity genes for a cell of interest, the method comprising the steps of:

determining the differential breadth of H3K4me3 modified regions for protein-coding genes in a cell of interest;

determining a network score for each of the protein-coding genes based on the differential breadth of the H3K4me3 modified regions and the interactions between the protein products of each of the protein-coding genes over at least one network, wherein the network contains information of the interactions between the products of the protein-coding genes;

determining a cell identity score for each of the protein-coding genes based on a combination of the differential breadth and network score;

prioritising each of the protein-coding genes according to its cell identity score;

thereby identifying the cell identity genes for the cell of interest.

The present invention provides a method of determining the cell identity genes for a cell of interest, the method comprising the steps of:

determining the differential breadth of H3K4me3 modified regions for each protein-coding gene in a cell of interest;

determining a network score for each protein-coding gene in the cell of interest based on the differential breadth of H3K4me3 modified regions and the interactions between the protein products of each protein-coding gene over at least one network, wherein the network contains information of the interactions between the products of the protein-coding gene;

determining a cell identity score for each protein-coding gene in the cell of interest based on a combination of the differential breadth and network score;

prioritising each protein-coding gene according to its cell identity score;

thereby identifying the cell identity genes for the cell of interest.

The present invention also provides a method of determining the cell identity genes for a cell of interest, the method comprising the steps of:

determining a differential broadness score (DBS) for each protein-coding gene in a cell of interest wherein the DBS is based on the difference in breadth of H3K4me3 modified regions for all protein-coding genes compared to the median breadth of the H3K4me3 modified regions for the same protein-coding genes in a population of different cell types;

determining a network score for each protein-coding gene in the cell of interest based on the DBS and the interactions between the products of each protein-coding gene over at least one network, wherein the network contains information of the interactions between the products of the protein-coding genes in the cell;

determining a cell identity score (RegDBS) for each protein-coding gene in the cell of interest based on a combination of the DBS and network scores;

prioritising each protein-coding gene according to its RegDBS;

thereby identifying the cell identity genes for the cell of interest.

The present invention also provides a method of determining the factors required for maintaining a cell type in vitro, the method comprising the steps of:

determining a differential broadness score (DBS) for each protein-coding gene in a cell of interest wherein the DBS is based on the difference in breadth of H3K4me3 modified regions for all protein-coding genes compared to the median breadth of the H3K4me3 modified regions for the same protein-coding genes in a population of different cell types;

determining a network score for each protein-coding gene in the cell of interest based on the DBS and the interactions between the protein products of each protein-coding gene over at least one network, wherein the network contains information of the interactions between the product of each protein-coding gene and other protein-coding gene products in the cell;

determining a cell identity score (RegDBS) for each protein-coding gene in the cell of interest based on a combination of the DBS and network scores;

prioritising each protein-coding gene according to its RegDBS thereby identifying the cell identity genes for the cell of interest, wherein each cell identity gene encodes a factor associated with the cell identity of the cell of interest;

thereby identifying the factors required for maintaining the cell of interest in vitro.

In any embodiment, the differential breadth of the H3K4me3 modified regions may be determined by obtaining information on the breadth of the H3K4me3 modified region for each protein-coding gene in a cell of interest to obtain a gene peak breadth score (B) for each protein-coding gene in the cell and calculating the difference between the gene breadth score of each gene in the cell and the median gene breadth score for the same gene across a population of cells of different types, thereby determining a differential broadness score (DBS) for each protein-coding gene in the cell of interest.

The breadth of the H3K4me3 modified region may be determined based on ChIP-seq information, more preferably wherein the information is obtained from any of the epigenome Roadmap, BLUEPRINT or ENCODE databases. In any embodiment, determining the gene peak breadth score (B) comprises firstly defining regions of the genome for which there is significant H3K4me3 modification (histone modification reference peak loci, or RPL). Preferably the RPL are obtained by merging ChIP-seq peak regions obtained, across all cell types. Preferably the peak regions that are merged are overlapping peak regions.

Preferably the breadth of the H3K4me3 modified region is determined based on ChIP-seq information, optionally wherein the information is derived from H3K4me3 profiling methods such as CUT&RUN, scChIC-seq, more preferably wherein the information is obtained from the ENCODE database.

In a preferred embodiment, determining the gene peak breadth score (B) for each protein-coding gene may comprise excluding genes for which H3K4me3 and H3K27me3 modified regions are identified (i.e., poised genes).

In any embodiment, determining the DBS may comprise combining information on the difference in breadth of the H3K4me3 modified region for each protein-coding gene (compared to control/background cells) with the significance of that difference in breadth. In certain embodiments, determining the DBS may comprise multiplying, normalising or summing the difference in breadth and the significance of the difference, preferably wherein the DBS is determined by summing the difference in peak breadth with the significance of the difference. More preferably, the DBS is determined by summing difference in H3K4me3 peak breadth and the $-\log_{10}$ value of the significance.

The significance of the difference in breadth of the H3K4me3 modified region can be determined by any standard statistical method. In one example, the method used is a one sample Wilcoxon test.

In any embodiment, determining the network score for each protein-coding gene in the cell of interest comprises combining information on the DBS for each protein-coding gene, the number of outdegree nodes of the gene and the level of connection of the gene in the network. In preferred embodiments, the network score is determined by summing the DBS of connected genes, and weighted for the number of outdegree nodes of the gene and the level of connection to obtain a weighted sum of DBS for the connected protein-coding genes in the network.

Typically, the protein-protein interaction network is the STRING database although any sub-network as referred to herein which contains information relating to the interactions of proteins within a given cell type may be used.

It will be understood that the cell identity score (RegDBS) is an indicator of the regulatory influence of each protein-coding gene on the identity of the cell.

In any embodiment, determining the RegDBS may comprise preferentially weighting protein-coding genes which encode regulatory factors.

In any embodiment, determining the RegDBS for each protein-coding gene may comprise summing the DBS score with the normalised network score across all genes in the cell of interest. Preferably the summing of the DBS and network score further comprises weighting the DBS relative to the network score by a factor of 2:1, 1:1, 3:1, 4:1, 5:1, and 1:2. More preferably, the RegDBS is determined by weighting the DBS score by a factor of 2 relative to the network score.

In any embodiment, the step of prioritising each protein-coding gene according to its RegDBS may comprise ordering the genes based on the RegDBS value.

In a preferred embodiment, the method comprises selecting the cell identity genes which encode receptor-ligand pairs thereby identifying signalling molecules required for maintaining the cell of interest in vitro. Preferably the factors required for maintaining the cell of interest in vitro are selected from the group consisting of cell surface receptors or ligands involved in cell signalling. Preferably, determining the factors required for maintaining the cell of interest in vitro comprises ranking each protein-coding gene that encodes a cell surface receptor according to its RegDBS score. The method may further comprise prioritising ligands associated with the receptors based on the DBS score for each ligand to obtain a combined ranking of receptors and ligands and wherein the combined ranking identifies the ligands for use in supplementing culture media for maintaining the cell of interest in vitro.

In further embodiments, the factors for maintaining the cell of interest in vitro may comprise transcription factors, or epigenetic remodelling factors. Accordingly, the method may further comprise selecting the cell identity genes which encode transcription factors thereby identifying the transcription factors required for maintaining the cell of interest in vitro.

Accordingly, the present invention also provides a method of determining the cell identity genes for a cell of interest, the method comprising the steps of:

determining a H3K4me3 gene peak breadth score (B) for each protein-coding gene (g) in a cell of interest (x), wherein the gene peak breadth score is the sum of the length of the regions in the promoter of each protein-coding gene comprising H3K4me3 modifications;

determining the normalised difference in gene peak breadth score ($\Delta$peakbreadth$^x_g$) between the cell of interest and the median gene peak breadth score of a population of cells representative of background gene peak breadth scores, and the significance of that difference (Pval);

summing the $\Delta$peakbreadth and P val values to obtain a differential broadness score (DBS$^x_g$) for each protein-coding gene in the cell;

determining a network score (N$^x_g$) for each protein-coding gene in the cell of interest by combining information on the differential broadness score (DBS$^x_g$) of connected genes (r) in a network, wherein the network contains information of the interactions between the product of each protein-coding gene and other protein-coding gene products in the cell; wherein the differential broadness score is corrected for the number of outdegree nodes of the gene (O) and the level of connection of the gene (L); wherein preferably the weighted sum of the differential broadness scores (DBS$^x_g$) is calculated up to the third level of connection;

normalising the network score Net$^x_g$ across all protein-coding genes (g) in the cell of interest (x);

scoring each protein-coding gene in the cell of interest based on a combination of the differential broadness score (DBS$^x_g$) and network scores (Net$^x_g$), thereby determining a regulatory differential broadness score (RegDBS$^x_g$) for each protein-coding gene in the cell of interest; wherein the RegDBS$^x_g$ is an indicator of the regulatory influence of each protein-coding gene on the identity of the cell;

prioritising each gene according to its RegDBS$^x_g$ thereby identifying the cell identity genes for the cell of interest.

Preferably, the interactions between gene nodes are selected if the experimental score in the network is greater than zero and the combined score is greater than 500.

In further embodiments, determining the network score comprises removing protein-coding genes with no associated peak H3K4me3 breadth from the protein-protein interaction network.

Preferably, scoring each protein-coding gene in the cell of interest comprises summing the differential broadness score (DBS$^x_g$) with the normalised network score (Net$^x_g$) for the gene, more preferably wherein the differential broadness score (DBS$^x_g$) is weighted by a factor of at least 2 with respect to the normalised network score (Net$^x_g$).

The present invention also provides a method of determining the factors required for conversion of a source cell to a cell exhibiting at least one characteristic of a target cell type, the method comprising the steps of:

determining the differential breadth of H3K4me3 modified regions for protein-coding genes in a source cell and a target cell type to obtain a score of the H3K4me3 modification for protein-coding genes (DBS) in the source and target cell type;

calculating the difference between the DBS of the source cell and the DBS of the target cell to obtain a measure of the difference in H3K4me3 modification (cell conversion DBS) between the source and target cell for each of the protein-coding genes;

determining a network score for conversion from the source cell type to the target cell type based on the cell conversion DBS and the interactions between the protein products of each of the protein-coding genes over at least one network, wherein the network contains information of the interactions between the products of protein-coding genes in a cell;

determining a cell identity conversion score for each of the protein-coding genes in the target cell based on a combination of the cell conversion $\Delta$DBS and network score;

prioritising each of the protein-coding genes according to its cell identity conversion score to identify the cell identity genes for the target cell wherein each cell identity gene encodes a factor associated with the cell identity of the target cell;

thereby determining the factors required for conversion of a source cell to a cell exhibiting at least one characteristic of a target cell type.

The present invention also provides a method of determining the factors required for conversion of a source cell to a cell exhibiting at least one characteristic of a target cell type, the method comprising the steps of:

determining the differential breadth of H3K4me3 modified regions for each protein-coding gene in a source cell and a target cell type to obtain a score of the H3K4me3 modification for each protein-coding gene (DBS) in the source and target cell type;

calculating the difference between the DBS of the source cell and the DBS of the target cell to obtain a measure of the difference in H3K4me3 modification (cell conversion $\Delta$DBS) between the source and target cell for each protein-coding gene;

determining a network score for conversion from the source cell type to the target cell type based on the cell conversion $\Delta$DBS and the interactions between the protein products of each protein-coding gene over at least one network, wherein the network contains information of the interactions between each protein-coding gene product and other gene products in a cell;

determining a cell identity conversion score for each protein-coding gene in the target cell based on a combination of the cell conversion $\Delta$DBS and network score;

prioritising each protein-coding gene according to its cell identity conversion score to identify the cell identity genes for the target cell wherein each cell identity gene encodes a factor associated with the cell identity of the target cell;

thereby determining the factors required for conversion of a source cell to a cell exhibiting at least one characteristic of a target cell type.

The present invention also provides a method of determining the factors required for conversion of a source cell to a cell exhibiting at least one characteristic of a target cell type, the method comprising the steps of:

determining a differential broadness score (DBS) for each protein-coding gene in a source cell and in a target cell, wherein the DBS is based on the difference in breadth of H3K4me3 modified regions for all protein-coding genes compared to the median breadth of the H3K4me3 modified regions for the same protein-coding genes in a population of different cell types;

calculating the difference between the DBS of the source cell and the DBS of the target cell to obtain a cell conversion ΔDBS for each protein-coding gene;

determining a network score for cell conversion from the source cell type to the target cell type, based on the cell conversion ΔDBS and the interactions between the protein products of each gene over at least one network, wherein the network contains information of the interactions between the product of each protein-coding gene and other protein-coding gene products in the cell;

determining a cell identity conversion score (RegΔDBS) for each protein-coding gene in the target cell based on a combination of the cell conversion ΔDBS and network score prioritising each protein-coding gene according to its cell conversion RegΔDBS to identify the cell identity genes for the target cell, wherein each cell identity gene encodes a factor associated with the cell identity of the target cell;

thereby determining the factors required for conversion of a source cell to a cell exhibiting at least one characteristic of a target cell type.

In any embodiment, the differential breadth of the H3K4me3 modified regions is determined by obtaining information on the breadth of the H3K4me3 modified region for each protein-coding gene in the source cell and the target cell to obtain a gene peak breadth score (B) for each gene in each cell type and calculating the difference between the gene peak breadth score of each protein-coding gene in the cell type and the median gene peak breadth score for the same gene across a population of cells of different types, thereby determining a differential broadness score (DBS) for each gene in both the source and target cells.

The breadth of the H3K4me3 modified region may be determined based on ChIP-seq information, more preferably wherein the information is obtained from any of the epigenome Roadmap, BLUEPRINT or ENCODE databases. In any embodiment, determining the gene peak breadth score (B) comprises firstly defining regions of the genome for which there is significant H3K4me3 modification (histone modification reference peak loci, or RPL). Preferably the RPL are obtained by merging ChIP-seq peak regions obtained, across all cell types. Preferably the peak regions that are merged are overlapping peak regions.

Preferably the breadth of the H3K4me3 modified region is determined based on ChIP-seq information, more preferably wherein the information is obtained from the ENCODE database.

In a preferred embodiment, determining the gene peak breadth score (B) for each protein-coding gene includes excluding genes for which H3K4me3 and H3K27me3 modified regions are identified (i.e., poised genes).

In any embodiment, determining the DBS for each protein-coding gene in the source cell and the target cell may comprise combining information on the difference in H3K4me3 breadth for each protein-coding gene (compared to background H3K4me3 breadth), with the significance of that difference. In certain embodiments, determining the DBS may comprise multiplying, normalising or summing the difference in peak breadth and the significance of the difference, preferably wherein the DBS is determined by summing the difference in peak breadth with the significance of the difference. More preferably, the DBS is determined by summing difference in peak breadth and the −log 10 value of the significance.

The significance of the difference in breadth of the H3K4me3 modified region can be determined by any standard statistical method. In one example, the method used is a one sample Wilcoxon test.

In a preferred embodiment, calculating the difference between the DBS of the source cell and the DBS of the target cell to obtain a cell conversion ΔDBS for each gene comprises subtracting the source cell DBS for each protein-coding gene from the target cell DBS for each gene to obtain a cell conversion ΔDBS for each gene. The cell conversion ΔDBS for each protein-coding gene provides a measure of the difference in the breadth of the H3K4me3 modified region for a given protein-coding gene between the source cell and the target cell.

Preferably, the network score for cell conversion from a source cell to a target cell is the weighted combination of the cell conversion ΔDBS of the connected genes in the network. For example, determining the network score for cell conversion may comprise combining information on the cell conversion ΔDBS for each gene, the number of outdegree nodes of the gene and the level of connection of the gene in the network. In preferred embodiments, the network score is determined by summing the cell conversion ΔDBS of connected genes, and weighted for the number of outdegree nodes of the gene and the level of connection to obtain a weighted sum of cell conversion ΔDBS for the connected genes in the network.

Typically, the protein-protein interaction network is the STRING database although any sub-network as referred to herein which contains information relating to the interactions of proteins within a given cell type may be used.

It will be understood that the cell conversion identity score (cell conversion RegΔDBS) is an indicator of the regulatory influence of each protein-coding gene on the change in identity of the cell.

In any embodiment, determining the cell conversion RegΔDBS may comprise preferentially weighting protein-coding genes which encode regulatory factors.

In any embodiment, determining the cell conversion RegΔDBS for each protein-coding gene comprises summing the cell conversion ΔDBS score with the normalised cell conversion network score across all protein-coding genes. Preferably the summing of the cell conversion ΔDBS and cell conversion network score further comprises weighting the cell conversion ΔDBS relative to the cell conversion network score by a factor of 2:1, 1:1, 3:1, 4:1, 5:1, and 1:2. More preferably, the cell conversion RegΔDBS is determined by weighting the cell conversion ΔDBS score by a factor of 2 relative to the network score.

In any embodiment, the step of prioritising each protein-coding gene according to its cell conversion RegΔDBS comprises ordering the genes based on the cell conversion RegΔDBS value.

In a preferred embodiment, the cell conversion factors comprise transcription factors, or epigenetic remodelling factors. Accordingly, the method may further comprise selecting the genes which encode transcription factors thereby identifying the transcription factors required for conversion of a source cell to a cell exhibiting at least one characteristic of a target cell type. Preferably, the conversion is transdifferentiation of a differentiated source cell to a differentiated target cell.

In an alternative embodiment, the method comprises selecting the protein-coding genes which encode receptor-ligand pairs thereby identifying the signalling molecules required for conversion of a source cell to a target cell. Preferably the factors required for conversion of a source cell to a target cell are selected from the group consisting of cell surface receptors or ligands involved in cell signalling. Preferably, determining the factors required for conversion of a source cell to a target cell comprises ranking each gene that encodes a cell surface receptor according to its cell conversion RegΔDBS score. The method may further comprise prioritising ligands associated with the receptors based on the cell conversion ΔDBS score for each ligand to obtain a combined ranking of receptors and ligands and wherein the combined ranking identifies the ligands for use in supplementing culture media for conversion of a source cell to a target cell. Preferably the conversion is directed differentiation from a pluripotent source cell to a differentiated target cell.

Accordingly, the present invention also provides a method of determining the factors required for conversion of a source cell to a cell exhibiting at least one characteristic of a target cell type, the method comprising the steps of:

determining a H3K4me3 gene peak breadth score (B) for each protein-coding gene (g) in a source cell interest (S), and in a target cell (T) wherein the gene peak breadth score is the sum of the length of the regions in the promoter of each protein-coding gene comprising H3K4me3 modifications;

determining the normalised difference in gene peak breadth score ($\Delta peakbreadth^S_g$) between the source cell and the median gene peak breadth score of a population of cells representative of background gene peak breadth scores, and the significance of that difference ($Pval^S_g$);

determining the normalised difference in gene breadth score ($\Delta peakbreadth^T_g$) between the target cell and the median gene breadth score of a population of cells representative of background gene breadth scores, and the significance of that difference ($Pval^T_g$);

summing the $\Delta peakbreadth^S_g$ and $Pval^S_g$ values to obtain a differential broadness score ($DBS^S_g$) for each protein-coding gene in the source cell;

summing the $\Delta peakbreadth^T_g$ and $Pval^T_g$ values to obtain a differential broadness score ($DBS^T_g$) for each protein-coding gene in the target cell;

subtracting the differential broadness score ($DBS^S_g$) for each protein-coding gene in the source cell from the differential broadness score ($DBS^T_g$) for the same gene in the target cell to obtain a cell conversion ΔDBS ($\Delta DBS^{T-S}_g$) for each protein-coding gene in the target cell;

determining a network score ($N^{T-S}_g$) for each gene in the target cell by combining the cell conversion differential broadness score ($\Delta DBS^{T-S}_g$) of connected genes (r) in a network, wherein the network contains information of the interactions between the products of each protein-coding gene in the cell; wherein the differential broadness score is corrected for the number of outdegree nodes of the gene (O) and the level of connection of the gene (L); wherein preferably the weighted sum of the cell conversion differential broadness scores ($\Delta DBS^{T-S}_g$) is calculated up to the third level of connection;

normalising the cell conversion network score $Net^{T-S}_g$ across all protein-coding genes;

scoring each protein-coding gene based on a combination of the cell conversion differential broadness score ($\Delta DBS^{T-S}_g$) and cell conversion network scores ($Net^{T-S}_g$), thereby determining a cell conversion regulatory differential broadness score ($Reg\Delta DBS^{T-S}_g$) for each protein-coding gene; wherein the $Reg\Delta DBS^{T-S}_g$ is an indicator of the difference in the regulatory influence of each protein-coding gene on the target cell compared to the source cell;

prioritising each protein-coding gene according to its $Reg\Delta DBS^{T-S}_g$ thereby identifying the factors required for conversion of a source cell to a cell exhibiting at least one characteristic of a target cell type.

Preferably, the interactions between gene nodes are selected if the experimental score in the network is greater than zero and the combined score is greater than 500.

In further embodiments, determining the network score comprises removing genes with no associated peak H3K4me3 breadth from the protein-protein interaction network.

Preferably, scoring each protein-coding gene in the cell of interest comprises summing the differential broadness score ($\Delta DBS^{T-S}_g$) with the network score ($Net^{T-S}_g$) for the gene, more preferably wherein the differential broadness score ($\Delta DBS^{T-S}_g$) is weighted by a factor of at least 2 with respect to the network score ($Net^{T-S}_g$).

In any embodiment of the above aspect, the method comprises selecting the subset of protein-coding genes encoding transcription factors, thereby identifying the transcription factors required for conversion of a source cell to a cell exhibiting at least one characteristic of a target cell type. Preferably, the factors identified are for transdifferentiation of a differentiated source cell to a differentiated target cell.

In a further embodiment of the above aspect, the method comprises selecting the protein-coding genes encoding receptor-ligand pairs, thereby identifying the signalling molecules required conversion of a source cell to a cell exhibiting at least one characteristic of a target cell type. Preferably, the factors identified are for directed differentiation of a pluripotent source cell to a differentiated target cell.

In further embodiments, the method further comprises determining the combined ranks of genes encoding receptors and of genes encoding the receptor ligands in receptor-ligand pairs, wherein the ranking is based on RegDBS, and DBS for the receptors and ligands respectively, thereby identifying the receptor-ligand pairs required for cell maintenance.

In further embodiments of the above aspects, the method further comprises the step of removing transcriptionally redundant TFs from the ranked lists from each cell type.

Further still, in any of the above methods, the method may comprise subsequently contacting a population of the cell of interest, or a source cell, with one or more of the identified factors so as to maintain the cell of interest in vitro or to convert the source cell to a cell exhibiting at least one characteristic of the target cell. Alternatively, the method may comprise transfecting a cell of interest source cell with a nucleic acid encoding the one or more factors, so as to maintain the cell of interest in vitro or to convert the source cell to a cell exhibiting at least one characteristic of the target cell.

The present invention also provides a method of maintaining a population of cells in vitro, the method comprising:

providing a population of a cell of interest in a cell culture;

determining a differential broadness score (DBS) for each protein-coding gene in the cell of interest wherein the DBS is based on the difference in breadth of H3K4me3 modified regions for all protein-coding genes compared to the median breadth of the H3K4me3 modified regions for the same genes in a population of different cell types;

determining a network score for each protein-coding gene in the cell of interest based on the DBS and the interactions between the protein products of each gene over at least one network, wherein the network contains information of the interactions between the product of each protein-coding gene and other protein-coding gene products in the cell;

scoring each protein-coding gene in the cell of interest based on a combination of the DBS and network scores, thereby determining a RegDBS for each protein-coding gene in the cell of interest; wherein the RegDBS is an indicator of the importance of each protein-coding gene for cell identity;

prioritising each protein-coding gene according to its RegDBS thereby identifying the cell identity genes for the cell of interest, wherein each cell identity gene encodes a factor associated with the cell identity of the cell of interest;

contacting the population of the cell of interest with one or more of the factors associated with the cell identity of the cell of interest;

culturing the population of cells for a sufficient time and under conditions to allow for the maintenance of the cell of interest in the cell culture thereby maintaining a population of cells in vitro.

In certain embodiments, contacting the cells with the factors may comprise transfecting the cells with one or more nucleic acid molecules encoding the factors and expressing the factors in the cell. Alternatively, contacting may comprise contacting the cell with an agent that increases the expression of the one or more factors.

The present invention also provides a method of maintaining a population of astrocytes in vitro, the method comprising the following steps in order:

providing a population of astrocytes in a cell culture;

contacting the population of astrocytes with a set of factors selected from: FN1, COL4A1, LAMB1, ADAM12, WNT5A, COL1A2 and EDIL3, or variants thereof, for maintaining at least one characteristic of an astrocyte, culturing the population of astrocytes for a sufficient time and under conditions to allow for the maintenance of the astrocytes in the cell culture;

thereby maintaining the population of astrocytes in vitro.

Preferably the factors comprise, consist or consist essentially of: FN1, COL4A1, LAMB1, ADAM12, WNT5A, COL1A2 and EDIL3.

In certain embodiments, the method comprises contacting the astrocytes with one or more of, two or more, three or more, four or more, five or more, or 6 of FN1, COL4A1, LAMB1, ADAM12, WNT5A, COL1A2 and EDIL3.

In a preferred embodiment, the method comprises contacting the astrocytes with FN1, COL4A1, LAMB1, ADAM12, WNT5A, COL1A2 and EDIL3.

In one embodiment, the method comprises contacting the astrocytes with at least FN1, LAMB1 or COL1A2 (optionally contacting the astrocytes with FN1 and LAMB1 or with FN1 and COL1A2 or with all three of FN1, LAMB1 and COL1A2). Optionally one or more of COL4A1, ADAM12, and EDIL3 are also used for contacting the astrocytes.

In any embodiment, a functional variant of any one of the factors, e.g. FN1, COL4A1, LAMB1, ADAM12, WNT5A, COL1A2 and EDIL3, may be used.

In any method described herein, the method may further include the step of administering the astrocytes, or cell population made according to the present methods, to an individual.

The present invention also provides a method of maintaining a population of cardiomyocytes in vitro, the method comprising:

providing a population of cardiomyocytes in a cell culture;

contacting the population of cardiomyocytes with one or more factors selected from: FN1, COL3A1, TFPI, FGF7, APOE, C3, COL1A2, SERPINE1, COL6A3, CXCL12, for maintaining at least one characteristic of a cardiomyocyte, culturing the population of cardiomyocytes for a sufficient time and in conditions suitable for maintaining the cardiomyocytes in the cell culture;

thereby maintaining the population of cardiomyocytes in vitro.

Preferably the factors comprise, consist or consist essentially of: FN1, COL3A1, TFPI, FGF7, APOE, C3, COL1A2, SERPINE1, COL6A3, CXCL12.

In certain embodiments, the method comprises contacting the cardiomyocytes with one or more, two or more, three or more, four or more, five or more, 6 or more, 7 or more, 8 or more or 9 of: FN1, COL3A1, TFPI, FGF7, APOE, C3, COL1A2, SERPINE1, COL6A3, CXCL12.

In a preferred embodiment, the method comprises contacting the cardiomyocytes with at least FN1, COL3A1 (Collagen III), TFP1, FGF7 and APOE, or functional variants thereof.

In a further preferred embodiment, the method comprises contacting the cardiomyocytes with FN1, COL3A1, TFPI, FGF7, APOE, C3, COL1A2, SERPINE1, COL6A3 and CXCL12.

In any embodiment, a functional variant of any one of the factors, e.g. FN1, COL3A1, TFPI, FGF7, APOE, C3, COL1A2, SERPINE1, COL6A3 and CXCL12, may be used.

In any method described herein, the method may further include the step of administering the cardiomyocytes, or cell population made according to the present methods, to an individual.

The present invention also provides a method of maintaining a population of smooth muscle cells in vitro, the method comprising:

providing a population of smooth muscle cells in a cell culture;

contacting the population of smooth muscle cells with one or more factors selected from: LAMA5, COL4A1, LAMA4, NID1, COL6A3, COL4A6, COL4A5, FGF10, FGF7, GNAS, COL7A1, COL1A1 and THBS1, for maintaining at least one characteristic of a smooth muscle cell, culturing the population of smooth muscle cells for a sufficient time and in conditions suitable for maintaining the smooth muscle cells in the cell culture;

thereby maintaining the population of smooth muscle cells in vitro.

Preferably the factors comprise, consist or consist essentially of: LAMA5, COL4A1, LAMA4, NID1, COL6A3, COL4A6, COL4A5, FGF10, FGF7, GNAS, COL7A1, COL1A1 and THBS1.

In certain embodiments, the method comprises contacting the smooth muscle cells with one or more, two or more, three or more, four or more, five or more, 6 or more, 7 or more, 8 or more or 9 or more of: LAMA5, COL4A1, LAMA4, NID1, COL6A3, COL4A6, COL4A5, FGF10, FGF7, GNAS, COL7A1, COL1A1 and THBS1.

In a preferred embodiment, the method comprises contacting the smooth muscle cells with Collagen 4, NID1, Collagen 6, FGF10, FGF7, Collagen 1 and THBS1.

In any embodiment, a functional variant of any one of the factors, e.g. LAMA5, COL4A1, LAMA4, NID1, COL6A3, COL4A6, COL4A5, FGF10, FGF7, GNAS, COL7A1, COL1A1 and THBS1, may be used.

In any method described herein, the method may further include the step of administering the smooth muscle cells, or cell population made according to the present methods, to an individual.

The present invention also provides a method of maintaining a population of endothelial cells, preferably aortic endothelial cells, in vitro, the method comprising:

provide a population of endothelial cells in a cell culture;

contacting the population of endothelial cells with one or more factors selected from: BMP6, ADAM9, LAMB1, LAMA4, THBS1, CTGF, BMP4, PDGFB, FN1 and CYR61, for maintaining at least one characteristic of an endothelial cell, culturing the population of endothelial cells for a sufficient time and in conditions suitable for maintaining the endothelial cells in the cell culture;

thereby maintaining the population of endothelial cells in vitro.

Preferably the factors comprise, consist or consist essentially of: BMP6, ADAM9, LAMB1, LAMA4, THBS1, CTGF, BMP4, PDGFB, FN1 and CYR61.

In certain embodiments, the method comprises contacting the endothelial cells with one or more, two or more, three or more, four or more, five or more, 6 or more, 7 or more, 8 or more or 9 or more of: BMP6, ADAM9, LAMB1, LAMA4, THBS1, CTGF, BMP4, PDGFB, FN1 and CYR61.

In a preferred embodiment, the method comprises contacting the endothelial cells with BMP6, THBS1, CTGF, BMP4, PDGFB, FN1 and CYR61.

In any embodiment, a functional variant of any one of the factors, e.g. MP6, ADAM9, LAMB1, LAMA4, THBS1, CTGF, BMP4, PDGFB, FN1 and CYR61, may be used.

In any method described herein, the method may further include the step of administering the endothelial cells, or cell population made according to the present methods, to an individual.

In any of the above methods for maintaining a cell of interest, the methods may include methods of maintaining transdifferentiating, undifferentiated, differentiated and transdifferentiated cells.

The present invention also provides a method of conversion of a source cell to a cell exhibiting at least one characteristic of a target cell type, the method comprising the steps of:

identifying the factors required for conversion of a source cell to a cell exhibiting at least one characteristic of a target cell type by any method described herein;

providing a source cell, contacting the source cell with one or more of the factors identified for conversion of the source cell to a target cell, culturing the source cell for a sufficient time and under conditions to allow conversion of the source cell to a cell exhibiting at least one characteristic of a target cell type;

thereby converting a source cell to a cell exhibiting at least one characteristic of a target cell type.

The present invention also provides a method of conversion of a source cell to a cell exhibiting at least one characteristic of a target cell type, the method comprising the steps of:

identifying the factors required for conversion of a source cell to a cell exhibiting at least one characteristic of a target cell type by any method described herein;

providing a source cell, contacting the source cell or increasing the amount of, one or more factors identified for conversion of the source cell to a target cell, culturing the source cell for a sufficient time and under conditions to allow conversion of the source cell to a cell exhibiting at least one characteristic of a target cell type;

thereby converting a source cell to a cell exhibiting at least one characteristic of a target cell type.

In preferred embodiments, the source cell is an H9 embryonic stem cell and the target cell type is any of the cell types listed in Table 3.

"Increasing" the amount may comprise expressing a nucleic acid encoding the one or more factors in the source cell; or contacting the source cell with an agent for increasing expression of the factor by the cell.

The present invention provides a method for differentiation of a source cell, the method comprising contacting the source cell or increasing the protein expression of one or more factors, or variant thereof, in the source cell, wherein the source cell is differentiated to exhibit at least one characteristic of a target cell, wherein:

the source cell is a pluripotent stem cell or progenitor cell and the target cell is any of the cells listed in Table 3; and the factors are selected from the factors listed in Table 3 for a given target cell type. Optionally, two or more, three or more, four or more, five or more, six or more, seven or more, eight or more, or nine or more, or 10 or more, or 11 or more, or 12 or more, or 13 or more, or 14 or more of the factors listed in Table 3 are used in the method.

The present invention provides a method for differentiation of a source cell, the method comprising increasing the protein expression of one or more factors, or variant thereof, in the source cell, wherein the source cell is differentiated to exhibit at least one characteristic of a target cell, wherein:

the source cell is a pluripotent stem cell or progenitor cell and the target cell is an astrocyte; and the factors are selected from: FN1, COL4A1, LAMB1, ADAM12, WNT5A, COL1A2 and EDIL3.

The present invention provides a method of generating a cell exhibiting at least one characteristic of an astrocyte from a pluripotent stem cell or progenitor cell, the method comprising:

contacting a pluripotent stem cell or progenitor cell with one or more of the factors selected from FN1, COL4A1, LAMB1, ADAM12, WNT5A, COL1A2 and EDIL3.

or variant thereof, in the source cell; and culturing the pluripotent stem cell or progenitor cell for a sufficient time and under conditions to allow differentiation to an astrocyte; thereby generating the cell exhibiting at least one characteristic of an astrocyte from a pluripotent stem cell or progenitor cell.

The present invention also provides a method for differentiation of a pluripotent stem cell, preferably an embryonic stem cell, or progenitor cell, the method comprising increasing the protein expression of one or more of FN1, COL4A1, LAMB1, ADAM12, WNT5A, COL1A2 and EDIL3 or variants thereof, in the stem cell, wherein the stem cell is differentiated to exhibit at least one characteristic of an astrocyte.

The present invention provides a method for differentiation of a pluripotent stem cell, preferably an embryonic stem cell, or progenitor cell to a cell that exhibits at least one characteristic of an astrocyte comprising: i) providing a pluripotent stem cell or progenitor cell, or a cell population comprising a pluripotent stem cell or progenitor cell; ii) transfecting said pluripotent stem cell with one or more nucleic acids comprising a nucleotide sequence that encodes one or more factors important for astrocyte cell identity; and iii) culturing said cell or cell population, and optionally monitoring the cell or cell population for at least one characteristic of the astrocyte cell, wherein preferably, the factors for differentiating a pluripotent stem cell or progenitor cell to an astrocyte, or the factors for generating a cell exhibiting at least one characteristic of an astrocyte comprise, consist or consist essentially of: FN1, COL4A1, LAMB1, ADAM12, WNT5A, COL1A2 and EDIL3.

In certain embodiments, the progenitor cell is preferably a neural progenitor cell or a cell obtained from a population of neural progenitor cells.

Preferably, the pluripotent stem cell is an embryonic stem cell.

The present invention provides a method of generating a cell exhibiting at least one characteristic of an astrocyte from an embryonic stem cell, the method comprising:

increasing the amount of any one or more of FN1, COL4A1, LAMB1, ADAM12, WNT5A, COL1A2 and EDIL3 or variant thereof, in the embryonic stem cell; and culturing the embryonic stem cell for a sufficient time and under conditions for differentiation into an astrocyte; thereby generating the cell exhibiting at least one characteristic of an astrocyte from an embryonic stem cell.

In certain embodiments, increasing the amount of one or more of the above recited factors comprises expressing a nucleic acid encoding one or more of the factors in the source cell (i.e., the stem cell). Alternatively, the factor may be provided directly to the cell by way of the cell culture medium.

Typically, conditions suitable for target cell differentiation include culturing the cells for a sufficient time and in a suitable medium. A sufficient time of culturing may be at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days. A suitable medium may be one shown in Table 4.

Preferably, the at least one characteristic of the astrocyte is up-regulation of any one or more astrocyte markers and/or change in cell morphology. Relevant markers are described herein and known to those in the art. Exemplary markers for astrocytes include: GFAP, S100B, ALDH1L1, CD44 and GLAST1, or any of the markers listed in Table 1.

Preferably, the at least one characteristic of the cardiomyocyte is up-regulation of any one or more cardiomyocyte markers and/or change in cell morphology. Relevant markers are described herein and known to those in the art. Exemplary markers for cardiomyocytes include: NKX2.5, GATA4, GATA6, MEF2C, MYH6, ACTN1, CDH2 and GJA1, or any of the markers listed in Table 1.

Preferably, the at least one characteristic of the smooth muscle cell is up-regulation of any one or more smooth muscle cell markers and/or change in cell morphology. Relevant markers are described herein and known to those in the art. Exemplary markers for smooth muscle cells include: SM22 and α-SMA, or any of the markers listed in Table 1.

Preferably, the at least one characteristic of the endothelial cell is up-regulation of any one or more endothelial cell markers and/or change in cell morphology. Relevant markers are described herein and known to those in the art. Exemplary markers for endothelial cells include: CD31 and VWF, or any of the markers listed in Table 1.

The present invention also provides a cell exhibiting at least one characteristic of an astrocyte cell, a cardiomyocyte, a smooth muscle cell, or an endothelial cell produced by a method as described herein.

In any method described herein, the method may further include the step of expanding the cells exhibiting at least one characteristic of an astrocyte to increase the proportion of cells in the population exhibiting at least one characteristic of an astrocyte. The step of expanding the cells may be in culture for a sufficient time and under conditions for generating a population of cells as described below.

In any method described herein, the method may further include the step of expanding the cells exhibiting at least one characteristic of a cardiomyocyte to increase the proportion of cells in the population exhibiting at least one characteristic of a cardiomyocyte. The step of expanding the cells may be in culture for a sufficient time and under conditions for generating a population of cells as described below.

In any method described herein, the method may further include the step of administering the cells, or cell population including a cell, exhibiting at least one characteristic of an astrocyte, cardiomyocyte, smooth muscle cell or endothelial cell to an individual.

The present invention also provides a composition comprising a set of factors for (i) maintaining a population of astrocytes in vitro, or (ii) for generating a cell exhibiting at least one characteristic of an astrocyte from a pluripotent stem cell. Preferably, the composition comprises a set of factors selected from: FN1, COL4A1, LAMB1, ADAM12, WNT5A, COL1A2 and EDIL3, or variants thereof. Preferably the set of factors comprise, consist or consist essentially of: FN1, COL4A1, LAMB1, ADAM12, WNT5A, COL1A2 and EDIL3, or variants thereof. In certain embodiments, the composition may comprise one or more, two or more, three or more, four or more, five or more, or 6 of FN1, COL4A1, LAMB1, ADAM12, WNT5A, COL1A2 and EDIL3, or variants thereof. In one embodiment, the composition comprises at least FN1, LAMB1 or COL1A2 (optionally FN1 and LAMB1 or FN1 and COL1A2 or all three). Optionally the composition further comprises one or more of COL4A1, ADAM12, and EDIL3.

The present invention also provides a composition comprising a set of factors for maintaining a population of cardiomyocytes in vitro. Preferably, the composition comprises a set of factors selected from: FN1, COL3A1, TFPI, FGF7, APOE, C3, COL1A2, SERPINE1, COL6A3, CXCL12, or variants thereof. Preferably the set of factors comprise, consist or consist essentially of FN1, COL3A1, TFPI, FGF7, APOE, C3, COL1A2, SERPINE1, COL6A3, CXCL12, or variants thereof. In certain embodiments, the composition may comprise one or more, two or more, three or more, four or more, five or more, 6 or more, 7 or more, 8 or more or 9 of: FN1, COL3A1, TFPI, FGF7, APOE, C3, COL1A2, SERPINE1, COL6A3, CXCL12, or variants thereof. Most preferably, the factors comprise, consist or consist essentially of FN1, COL3A1 (Collagen III), TFP1, FGF7 and APOE.

In any aspect, the composition may further comprise one or more components for supporting the growth or maintenance of cells in culture in vitro.

In any aspect, the composition may be a cell culture media.

In any aspect, the composition may comprises the factors (i.e. proteins) or nucleic acids encoding the factors.

The present invention also provides methods of producing a cell culture media for (i) maintaining a population of astrocytes in vitro, (ii) for generating a cell exhibiting at least one characteristic of an astrocyte from a pluripotent stem cell or progenitor cell, or (iii) maintaining a population of cardiomyocytes in vitro, (iv) maintaining a population of smooth muscle cells in vitro, or (v) maintaining a population of endothelial cells in vitro, the methods comprising adding a composition as described herein to a cell culture media.

The present invention also provides a population of cells, wherein at least 5% of cells exhibit at least one characteristic of a cardiomyocyte and those cells are produced by a method as described herein. Preferably, at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% of the cells in the population exhibit at least one characteristic of a cardiomyocyte.

The present invention also provides a population of cells, wherein at least 5% of cells exhibit at least one characteristic of an astrocyte and those cells are produced by a method as described herein. Preferably, at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% of the cells in the population exhibit at least one characteristic of an astrocyte.

The present invention also provides a population of cells, wherein at least 5% of cells exhibit at least one characteristic of a smooth muscle cell and those cells are produced by a method as described herein. Preferably, at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% of the cells in the population exhibit at least one characteristic of a smooth muscle cell.

The present invention also provides a population of cells, wherein at least 5% of cells exhibit at least one characteristic of an endothelial cell and those cells are produced by a method as described herein. Preferably, at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% of the cells in the population exhibit at least one characteristic of an endothelial cell.

The present invention also relates to kits for use in maintaining a cell in vitro as disclosed herein. In some embodiments, a kit comprises one or more nucleic acids having one or more nucleic acid sequences encoding a factor described herein or variant thereof. Alternatively, the kit comprises one or more protein factors for supplementation of cell culture media for use as described herein. Preferably, the kit can be used to maintain an astrocyte, cardiomyocyte, smooth muscle cell or endothelial cell in culture. In some embodiments, the kit further comprises instructions for maintaining a cell, preferably an astrocyte, cardiomyocyte, smooth muscle cell or endothelial cell in vitro.

The present invention also relates to kits for producing a cell exhibiting at least one characteristic of a target cell, preferably an astrocyte or cardiomyocyte as disclosed herein. In some embodiments, a kit comprises one or more nucleic acids having one or more nucleic acid sequences encoding a factor described herein or variant thereof. Alternatively, the kit may comprise one or more proteins for supplementation of media for use in directed differentiation as described herein. Preferably, the kit can be used to produce a cell exhibiting at least one characteristic of an astrocyte or at least one characteristic of a cardiomyocyte. Preferably, the kit can be used with an embryonic stem cell. In some embodiments, the kit further comprises instructions for converting a source cell to a cell exhibiting at least one characteristic of a target cell according to the methods as disclosed herein. Preferably, the present invention provides a kit when used in a method of the invention described herein.

Preferred Embodiments

The following statements relate to preferred embodiments of the invention:

1. A method for maintaining a cell in vitro, the method comprising the steps of:
    providing a cell of interest in cell culture;
    determining the differential breadth of H3K4me3 modified regions for each protein-coding gene in said cell;
    determining a differential broadness score (DBS) for each protein-coding gene in said cell;
    determining a network score for each protein-coding gene in said cell based on the DBS and the interactions between the protein products of each protein-coding gene over at least one network,
    determining a cell identity score (RegDBS) for each protein-coding gene in said cell based on a combination of the DBS and network scores;
    prioritising each protein-coding gene according to its RegDBS thereby identifying the cell identity genes for said cell, wherein each cell identity gene encodes a factor associated with the cell identity of the cell of interest;
    contacting said cell of interest with one or more of the factors associated with the cell identity of said cell;
    culturing said cell of interest for a sufficient time and under conditions to allow for the maintenance of said cell in the cell culture;
    thereby maintaining the cell of interest in vitro.

2. A method of maintaining a cell in vitro, the method comprising:
    i. providing a cell of interest in a cell culture;
    ii. identifying a protein-coding gene encoding a factor, or variants thereof, that promotes maintenance of said cell, wherein the protein-coding gene comprises at least one H3K4me3 modified region;
    iii. contacting said cell of interest with at least two factors, or variants thereof, for maintaining at least one characteristic of said cell;
    iv. culturing said cell of interest for a sufficient time and under conditions to allow for the maintenance of said cell in the cell culture;
thereby maintaining the cell of interest in vitro.

3. A method of maintaining a cell in vitro, the method comprising:
    i. providing a cell of interest in a cell culture;
    ii. identifying a protein-coding gene encoding a factor, or variants thereof, that promotes maintenance of said cell, wherein the protein-coding gene comprises at least one H3K4me3 modified region;
    iii. contacting said cell of interest with one or more factors, or variants thereof, for maintaining at least one characteristic of said cell;
    iv. culturing said cell of interest for a sufficient time and under conditions to allow for the maintenance of said cell in the cell culture;

thereby maintaining the cell of interest in vitro.

4. A method according to any one of statements 1 to 3, wherein a cell of interest is a differentiated cell, differentiating cell, undifferentiated cell or transdifferentiated cell 5. A method according to any one of statements 1 to 4, wherein the cell of interest is a tissue.

6. A method of any one of statements 1 to 5, wherein the cell of interest is selected from a cell derived from the ectoderm, mesoderm and endoderm germ layers.

7. A method of any one of statements 1 to 6, wherein the cell of interest is selected from the group consisting of: astrocytes, neurospheres, cardiomyocytes, smooth muscle cells, endothelial cells, muscle cells, fibroblasts, melanocytes, epithelial cells, keratinocytes, melanocytes, and mononuclear cells, or any of the cells or tissues listed in Table 2.

8. A method of any one of statements 1 to 7, wherein the factor associated with the cell identity is any one or more of the factors listed in Table 2.

9. A method of any one of statements 1 to 8, wherein the cell of interest is cultured for sufficient for a sufficient time and under conditions to allow maintenance of said cell including culturing the cell for at least 3, 4, 5, 6, 7, 8, 9, 10, 11, 12, 13, 14, 15, 16, 17, 18, 19, 20, 21, 22, 23, 24, 25, 26, 27, 28, 29, 30 or more days.

10. A method of any one of statements 1 to 9, wherein the differential breadth of the H3K4me3 modified regions is determined by:

obtaining information on the breadth of the H3K4me3 modified region for each protein-coding gene in the cell of interest to obtain a gene peak breadth score (B) for each protein-coding gene in the cell; and calculating the difference between the gene breadth score of each gene in the cell and the average gene peak breadth score for the same gene across a population of cells of different types, thereby determining a differential broadness score (DBS) for each protein-coding gene in the cell of interest.

11. A method of statement 10, wherein determining the gene peak breadth score (B) comprises firstly defining regions of the genome for which there is significant H3K4me3 modification and defining those regions as histone modification reference peak loci (RPL).

12. A method of statement 10 wherein the RPL are obtained by merging ChIP-seq peak regions obtained, across all cell types, preferably wherein the peak regions that are merged are overlapping peak regions.

13. A method of any one of statements 9 to 12 wherein the gene peak breadth score (B) for each protein-coding gene comprises excluding genes for which H3K4me3 and H3K27me3 modified regions are identified, wherein the genes are identified as poised genes.

14. A method of any one of statements 1 to 13, wherein determining the cell identity score (RegDBS) comprises preferentially weighting protein-coding genes which encode regulatory factors.

15. A method of any one of statements 1 to 14, wherein the factors for maintaining the cell of interest in vitro are selected from the group consisting of: receptor-ligand pairs involved in cell signalling, preferably the ligands of the receptor-ligand pairs, transcription factors, and epigenetic remodelling factors.

16. A method of any one of statements 1 to 15, wherein the method comprises selecting the cell identity genes which encode receptor-ligand pairs involved in cell signalling, thereby identifying signalling molecules required for maintaining the cell of interest in vitro.

17. A method of statement 16, wherein each protein-coding gene that encodes a cell surface receptor is ranked according to its RegDBS score and each ligand associated with the receptor is ranked according to its DBS score, to obtain a combined ranking of receptors and ligands and wherein the combined ranking identifies the ligands for use in supplementing culture media for maintaining the cell of interest in vitro.

18. A method of statements 16 or 17, wherein the cell identity genes encode receptor-ligand pairs involved in cell signalling pathways such as signalling by WNT, NOTCH, Hegdehog, Hippo, GPCR, Integrins, TGFB family (BMP, Activin, TGFB receptor), receptor tyrosine kinases (such as EGFR, FGFR, VEGF, PDGF, MET, MST, SCF-KIT, Insulin receptors, ERBB2, NTRKs), non-receptor tyrosine kinases (PTK6), MTOR, and Retinoic acid.

19. A method of any one of statements 1 to 18, wherein the method further comprises selecting the cell identity genes which encode transcription factors thereby identifying the transcription factors required for maintaining the cell of interest in vitro.

20. A method of any one of statements 1 to 19, wherein determining the network score comprises removing protein-coding genes with no associated peak H3K4me3 breadth from the protein-protein interaction network.

21. A method of any one of statements 1 to 20, wherein the cell of interested in contacted with the two or more of factors by contacting the cell with an agent that increases the expression of the two or more factors.

22. A method of statement 21, wherein an agent is selected from the group consisting of a nucleotide sequence, a protein, an aptamer and small molecule and analogues or variants thereof.

23. A method of maintaining a population of cells in vitro by performing the method according to any one of statements 1 to 22.

24. A population of cells, wherein at least 5% of cells exhibit at least one characteristic of the cell of interest and those cells are produced by a method according to any one of statements 1 to 22.

25. A population of cells according to statement 24, wherein at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% of the cells in the population exhibit at least one characteristic of the cell of interest.

26. A method of any one of statements 1 to 23, wherein the method further includes the step of administering the cell of interest to an individual, or administering a population of cells according to statement 22 or 23 to an individual.

27. A method of conversion of a source cell to a cell exhibiting at least one characteristic of a target cell type, the method comprising the steps of:

providing a source cell;

determining the differential breadth of H3K4me3 modified regions for each protein-coding gene in a source cell and a target cell type to obtain a score of the H3K4me3 modification for each protein-coding gene (DBS) in the source and target cell type;

calculating the difference between the DBS of the source cell and the DBS of the target cell to obtain a measure of the difference in H3K4me3 modification (cell conversion ΔDBS) between the source and
target cell for each protein-coding gene;

determining a network score for conversion from the
source cell type to the target cell type based on the
cell conversion ΔDBS and the interactions between
the protein products of each protein-coding gene
over at least one network, wherein the network
contains information of the interactions between
each protein-coding gene product and other gene
products in a cell;

determining a cell identity conversion score for each
protein-coding gene in the target cell based on a
combination of the cell conversion DBS and network
score;

prioritising each protein-coding gene according to its
cell identity conversion score to identify the cell
identity genes for the target cell, wherein each cell
identity gene encodes a factor associated with the
cell identity of the target cell;

culturing the source cell for a sufficient time and under
conditions to allow conversion of the source cell to
a cell exhibiting at least one characteristic of a target
cell type;

thereby converting a source cell to a cell exhibiting at least
one characteristic of a target cell type, optionally, wherein
increasing the amount of the one or more factors comprises
i) contacting the source cell with factor or an agent which
increases expression of the factor by the cell; or ii) trans-
fecting the source cell with a nucleic acid that encodes the
factor and expressing the nucleic acid in the cell.

28. A method according to statement 27, wherein a
method of conversion is a method of differentiating,
reprogramming or transdifferentiating.

29. A method according to statement 27, wherein a source
cell is a differentiated cell, differentiating cell, undif-
ferentiated cell or transdifferentiated cell.

30. A method according to statement 27, wherein a source
cell is an embryonic stem cell and the target cell is one
of the cells listed in Table 3.

31. A method according to statement 30, wherein a source
cell is an embryonic stem cell and the factors for
conversion of the source cell are listed in Table 3.

As used herein, except where the context requires other-
wise, the term "comprise" and variations of the term, such
as "comprising", "comprises" and "comprised", are not
intended to exclude further additives, components, integers
or steps.

Further aspects of the present invention and further
embodiments of the aspects described in the preceding
paragraphs will become apparent from the following
description, given by way of example and with reference to
the accompanying drawings.

DETAILED DESCRIPTION OF THE EMBODIMENTS

Figure 1:
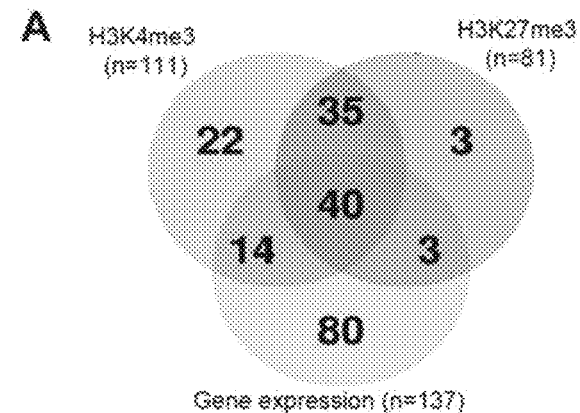
FIG. 1: H3K4me3 histone modifications mark cell iden-
tity genes. (A) A Venn-diagram depicting the number of cell
types used in this study. Histone modification data by
H3K4me3 and H3K27me3 ChIP-seq and gene expression
data by RNA-seq obtained from ENCODE repository. (B)
An illustration defining ChIP-seq peak breadth and peak
height. (C) An illustration of gene annotation to the cell type
representative ChIP-seq profiles. The ChIP-seq profiles were
mapped to the human genome (GRCh38) and to compare
peaks between cell types, we defined reference peak loci
(RPL) by merging ChIP-seq profiles across all cell types.
The table summarizes the genes assigned to each RPL and the calculated peak breadth (B) and height (H) values at each
locus. (D) The enrichment for cell identity and housekeeping
genesets by genes ordered by associated H3K4me3 peak
breadth and gene expression across 40 common cell types.
The x-axis consists of cumulative bins of genes with
H3K4me3 breadth values or gene expression levels ranked
in descending order and the cumulative bins increases by
one percentile interval. The enrichment score is computed
using FET (Fisher exact test). (E) Similarly, across 111 cell
types, the highest enrichment score for cell identity genesets
is attained for genes ranked by H3K4me3 breadth value and
with an associated H3K4me3 breadth greater than 87% of
the peak breadth distribution. n refers to the number of cell
types.
Figure 1:
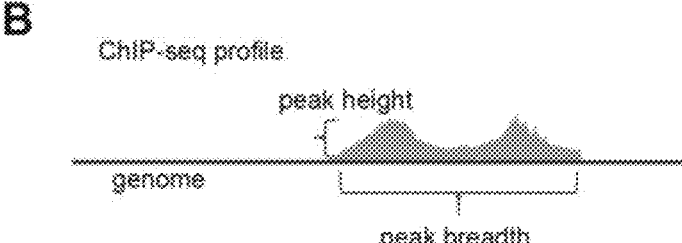
Figure 1:
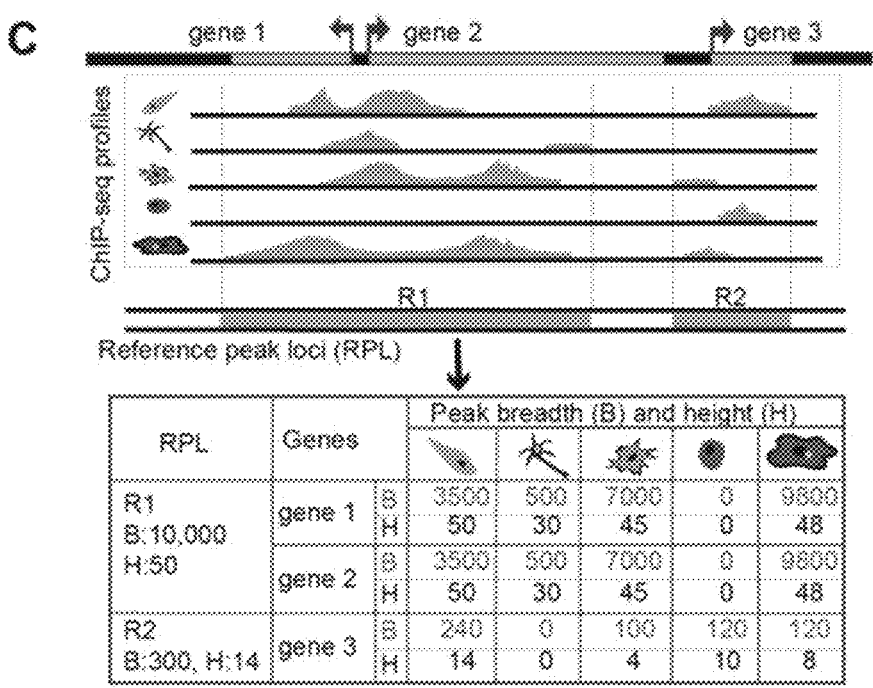
Figure 1:
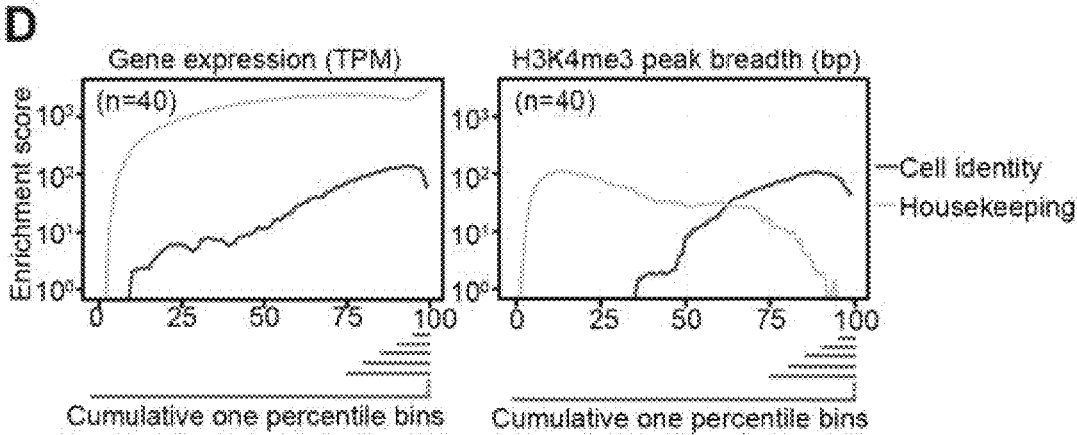
Figure 1:
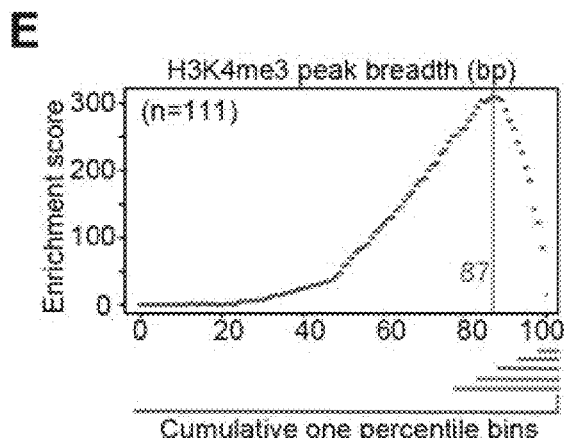

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

For purposes of interpreting this specification, terms used in the singular will also include the plural and vice versa.

The present inventors aimed to systematically identify factors that facilitate the development of serum-free chemically defined cell maintenance and differentiation media. In order to identify factors for cell maintenance or cell conversion, it was necessary to model the cell's identity or the change in cellular identity respectively.

The present invention provides a new computational approach (EpiMogrify) that takes advantage of available epigenetic datasets (e.g., via ENCODE and Roadmap consortia) and models the cell's epigenetic state using H3K4me3 and H3K27me3 histone modifications. EpiMogrify uses data-driven thresholds, statistics and incorporates protein-protein interaction networks information to prioritise key genes that regulate cellular identity (and thereby identify the cell identify genes for a given cell). The method of the invention systematically predicts signalling molecules for cell maintenance and directed differentiation in a multitude of cell types. Moreover, the methods of the invention can also prioritize other protein classes such as transcription factors (TFs) or epigenetic remodelers for cell maintenance or cell conversion.

The EpiMogrify Algorithm

The present invention provides a method of determining cell identity genes for a cell type, the method comprising:

selecting a subset of protein-coding genes based on prioritisation of the protein coding genes in the cell type according to the influence of the protein-coding gene on cell identity, wherein the prioritisation for a given protein-coding gene is based on combining information on the breadth of H3K4me3 modified regions of each protein-coding gene and the regulatory influence of the protein-coding gene products with other protein-coding gene products in the cell.

The method of the present invention (as described herein as "EpiMogrify") models the epigenetic state of the cell to predict factors important for cell identity, cell maintenance and cell conversion. The major sections of the algorithm include:

(i) Defining histone modification reference peak loci (ii) Identification of cell identity and cell maintenance factors (iii) Identification of cell conversion factors for directed differentiation and transdifferentiation.

The approach aims to model the cell state by leveraging on epigenetic histone modifications, for example H3K4me3 modifications, which are well-known transcriptional activator marks. ChIP-seq data for H3K4me3 and H3K27me3 (a repressor mark) histone modification profiles are available for various human cell types, including from ENCODE and Roadmap consortia data repositories.

The breadth of a ChIP-seq peak may be defined as the length of the genomic region with histone modification deposition in base pairs (bp), and the height of a ChIP-seq peak may be defined as the average enrichment of histone modification or signal value. It will be understood that ChIP-seq peak breadth may range from narrow to broad peaks and ChIP-seq peak heights may range from short to tall peaks.

(i) Defining Histone Modification Reference Peak Loci

For each cell type, samples may be pooled together to obtain a cell type representative ChIP-seq profile. The cell type representative ChIP-seq peak breadth is typically calculated by merging peak regions across the samples and peak height calculated by the maximum peak height across all samples. To compare the ChIP-seq peaks across various cell types, we defined reference peak loci (RPL) which is a set of regions obtained by combining the representative peaks across all cell types.

Let n be the number of cell types. For each cell type ranging from x1, x2, . . . xn, let b be the cell type ChIP-seq peak breadth and h be the ChIP-seq peak height. The genomic locations of reference peak loci (RPL) are obtained by merging the peak regions across all cell types. For each locus R1, R2, . . . Rn in RPL, the peak breadth (b) is calculated by merging overlapping peaks across cell types and peak height (h) is given by the maximum peak height of overlapping peaks.

$$RPL_b = U_{i=1}^{n} b_{xi}$$

$$RPL_h = \max_{i=1}^{n} h_{xi}$$

Protein-coding genes can be assigned to RPL based on the peak's genomic location and the gene's transcription start site (TSS). As H3K4me3 histone modification is a well-known promoter mark, the genes are typically assigned to a peak locus if the peaks overlap with the gene's promoter region (500 bp from the TSS). However it will be understood that the RPL can be located in another region of the gene relative to its TSS (including expanding the region beyond 500 bp from the TSS, including 1000 bp, 2000 bp or further from the TSS).

Preferably, in each cell type (x), the peak breadth score (B) of a gene (g) is calculated as the sum of the peak breadth of n peaks annotated to the gene. Whereas the peak height value of a gene is calculated as the maximum height of the n peaks annotated to the gene.

$$RPL_b^x$$

is the peak breadth profile of a given cell type x at the RPL (reference peak loci).

$$B_g^x = \sum_{b=1}^{n} (RPL_b^x)$$

(ii) Identification of Cell Identity Genes and Cell Maintenance Factors

EpiMogrify employs H3K4me3 ChIP-seq peak breadth to model cell state.

EpiMogrify uses a three-step approach to identify factors that are specific to the cell type. Firstly, the differential broadness score is computed at each RPL based on H3K4me3 ChIP-seq peak breadth. Secondly, the regulatory influence of each gene is determined based on the value of connected genes on the protein-protein interaction network. Finally, cell identity genes are predicted based on the ranked protein-coding genes and EpiMogrify predicts signalling molecules for cell state maintenance.

As used herein, the term "each" in reference to the protein-coding genes may refer to a plurality of the protein-coding genes in a given cell type. The plurality may comprise every protein-coding gene in the cell type. Alternatively, the plurality may comprise a subset of the protein-coding genes in the cell type. Thus, "each protein-coding gene" may comprise "each protein-coding gene in the cell type" or "each protein-coding gene in the cell type, further refined to include only a subset of the genes".

Further, it will be understood that where the methods of the invention require "determining the differential breadth of H3K4me3 modified regions for each protein-coding gene in a cell of interest" and the gene does not comprise an H3K4me3 modified region, the relevant gene will be excluded from further analysis. Thus, the present invention is limited to an assessment of genes for which there is at least H3K4me3 modification.

In certain embodiments, a subset of the plurality of protein-coding genes may be excluded at one or more of the steps of the method. For example, poised genes with the presence of both H3K4me3 and H3K27me3 ChIP-seq peaks at the gene's TSS are preferably removed from the model prior to calculating the DBS.

The skilled person will appreciate that the greater the number of protein-coding genes included in the analysis, the more robust the prediction of the cell identity factors. Further, the skilled person will recognise the need to balance this with the need to also consider the inclusion of protein-coding genes which provide the greatest information on cell identity (such as those protein-coding genes comprising only H3K4me3 modification at or about the TSS).

Moreover, it will be understood that in the subsequent steps of the EpiMogrify method, those genes for which differential H3K4me3 breadth is determined, will also be included in the subsequent network analysis. In other words, the genes considered in the first step of the method (determining differential broadness scores) will typically also be considered in the subsequent network score calculation.

Step 1: Calculate Differential Broadness Score

To obtain target cell type-specific ChIP-seq profile, the target cell type of interest may be compared with a set of background cell types within the group. For example, if the target cell type of interest is a primary cell type then the cell types in the background would be remaining primary and stem cell types.

The statistical significance of the modelling is improved if the cell types in the background set are not similar to the target cell type. Thus, in a preferred embodiment, the background cell types are only selected if the Spearman correlation of the ChIP-seq profiles with the target cell type is less than 0.9.

In the target cell type of interest (x), if more than one reference peak locus (RPL) is assigned to the gene (g), then the gene peak breadth score (B) is given by the union of assigned RPL's peak breadth (b) values. $BG_g^x$ is a set of gene peak breadth scores of background cell types at gene g and the background cell types are selected based on the distinctiveness from the target cell type (x). $\Delta peakbreadth_g^x$ is the normalised difference in gene breadth score between target cell type and average gene peak breadth score of background cell types. It will be appreciated that a number of approaches can be adopted for averaging gene peak breadth score in order to determine $\Delta peakbreadth_g^x$. Although median is used in this example, the skilled person will appreciate that it may also be possible to use means, modes or other indicators of averages.

The significance (p.value) of this difference can be estimated by any suitable statistical method known to the skilled person (on example is one sample Wilcoxon test). The differential broadness score (DBS) of cell type (x) and gene (g) can be measured as the sum of normalised Δpeakbreadth and Pval, as shown below, although it will be appreciated that any number of methods for combining the difference in peak breadth, and the significance of that difference may be used (including multiplication, subtraction, normalisation or a combination thereof).

$$B_g^x = \sum_{b=1}^{n}(RPL_b^x)$$

$$\Delta peakbreadth_g^x = \left[B_g^x - \text{median}\left(BG_g^x\right)\right] / \max_{i=1}^{n}[B_i^x - \text{median}(BG_i^x)]$$

$$p.val = \text{one sample Wilcoxon test}\left(B_g^x, BG_g^x\right)$$

$$Pval_g^x = -\log10 p.value\left(B_g^x, BG_g^x\right) / \max_{i=1}^{n}[-\log10]p.value(B_i^x, BG_i^x)$$

$$DBS_g^x = \Delta peakbreadth_g^x + Pval_g^x$$

Step 2: Calculate Regulatory Differential Broadness Score

To compute a gene's regulatory influence on cell identity genes of the cell type, STRING V10, a protein-protein interaction network, information is included.

Protein-protein interaction networks such as STRING, provide information on the source of the information which predicts interactions. For example, the interactions may be based on experimental data or in silico data, or both. In STRING, those interactions are also scored, which provides a measure of the reliability of the predicted interaction. In certain embodiments of the present invention, the interactions between the gene nodes are selected if the experimental score provided in the Network is greater than zero and the combined score is greater the 500. This ensures that high-quality network with experimental evidence is used to determine the regulatory influence of the gene.

For all genes in the STRING network (V), network score can be computed based on the combination of DBS of connected genes (r) in the gene's sub-network ($V_g$) and corrected for the number of outdegree nodes (O) of the gene and the level (L) of connection. To obtain a cell-specific network, genes with no associated broad H3K4me3 peak from the STRING network can be removed. The weighted sum of DBS scores of the connected genes can be calculated up to the third level of connection.

$$N_g^x = \sum_{r \in V_g} DBS_r^x / (L_r * O_r)$$

Normalised network score (Net) across all protein-coding genes G in the cell types x $$Net_g^x = N_g^x \big/ \max_{i \in G} N_i^x$$

Different combinations of DBS and Net scores can be used to determine the cell identity score (RegDBS). In a preferred embodiment, a 2:1 ratio of DBS to Network score (Net) is used as shown below.

$$RegDBS_g^x = DBS_g^x + \left(0.5 * Net_g^x\right)$$

Step 3: Predict Cell Identity Genes and Cell Maintenance Factors

EpiMogrify predicts protein-coding genes that mark the cell's identity by ranking the genes based on a cell identity score (RegDBS).

It will be understood that a protein-protein interaction network provides information on the connectedness of the products of protein-coding genes (i.e., proteins) rather than the connectedness of the genes themselves. Moreover, the skilled person will appreciate that there may be more than one "product" of a protein coding gene. Accordingly, in the method of the present invention, the product of a protein-coding gene will be understood to comprise any single, or all combinations of all products from a given protein-coding gene.

For cell maintenance, EpiMogrify predicts signalling molecules such as receptor and ligands essential for cell growth and survival. The inventors have recognised that about two-thirds of ligands are produced by the cell in an autocrine manner and the rest of the ligands are produced by supporting cell types to mimic the microenvironment. Therefore, to incorporate this into the present model, the receptors based on cell-specific RegDBS may be prioritised, as they should be both cell-specific and have a regulatory influence on the cell type of interest. Ligands from the cell type of interest and the supporting cell types based on DBS can then prioritized. Finally, the receptor-ligand pairs can then prioritized by the combined ranks of receptors and ligands. This approach enables the identification and prioritisation of ligands in the predicted receptor-ligand pairs for use in supplementing cell culture conditions.

(iii) Identification of Cell Conversion Factors for Directed Differentiation and Transdifferentiation EpiMogrify employs a three-step approach to identify cell conversion factors. Firstly, for cell conversion from source cell type to target cell type the change in differential broadness score is computed. Then the regulatory influence of the genes exerted on the change in cell state is determined. Finally, transcription factors are predicted for transdifferentiation and signalling molecules are predicted for directed differentiation.

Briefly: the cell conversion differential broadness score is calculated by $$DBS_g^S = \Delta peakbreadth_g^S + Pval_g^S$$

$$DBS_g^T = \Delta peakbreadth_g^T + Pval_g^T$$

$$\Delta DBS_g^{T-S} = DBS_g^T - DBS_g^S$$

where S is the source cell type and T is the target cell type. First, the differential broadness score (DBS) is computed for both the source and target cell types. Then, to obtain cell conversion ΔDBS, the difference between the source and target DBS scores are computed.

Next, the regulatory network score (N) for cell conversion from source cell type to target cell type is computed as the weighted sum of the cell conversion ΔDBS scores of the connected nodes. Similar to the cell-specific RegDBS calculation, the cell conversion RegDBS is calculated as the composite score of cell conversion ΔDBS and normalized network score (Net) in the ratio of 2:1.

$$N_g^{T-S} = \sum_{r \in V_g} \Delta DBS_r^{T-S} \big/ L_r * O_r$$

$$Net_g^{T-S} = N_g^{T-S} \big/ \max_{i \in G} N_i^{T-S}$$

$$Reg\Delta DBS_g^{T-S} = \Delta DBS_g^{T-S} + \left(0.5 * Net_g^{T-S}\right)$$

For each cell conversion, the protein-coding genes are ranked by RegΔDBS value. For transdifferentiation, EpiMogrify predicts transcription factors (TFs) which is a subset of protein-coding genes defined based on TFClass classification. For directed differentiation, EpiMogrify predicts signalling molecules such as receptors and ligands pairs. The receptors are prioritized by cell conversion RegΔDBS and the corresponding ligands are prioritized by cell conversion ΔDBS. Finally, the receptor-ligand pairs are prioritized by the combined ranks of receptors and ligands. The ligands in the predicted receptor-ligand pairs can be supplemented to the differentiation protocol.

In summary, EpiMogrify models the broad H3K4me3 histone modification feature and predicts cell identity protein-coding genes, signalling molecules for cell maintenance, signalling molecules for directed differentiation and TFs for transdifferentiation.

Definitions

As used herein, a "factor" for maintaining a cell in culture or factor for converting a source cell to a target cell, may comprise a protein, small molecule or other agent for use in supplementing cell culture media. Preferably the factor is a protein. The protein may be a signalling molecule, including a ligand which binds to cognate receptors, preferably on the cell surface, and which elicits a signalling cascade within the cell, to maintain at least one characteristic of the cell type. Alternatively, the factor may be a transcription factor, which promotes expression of genes associated with cell identity, and thereby facilitates maintenance of the cell type in vitro. Where the factors are transcription factors, the transcription factors can be provided directly to the cells, or alternatively, expressed in the cells by way of a nucleic acid expression vector or the like.

In certain embodiments, the present methods include the use of a small molecule which replicates the action of a factor identified herein, or which acts on the cell to increase the amount of a factor as described herein (e.g., to increase transcription of a gene encoding the factor).

In certain embodiments, the factor may be provided exogenously, e.g., in the form of recombinant protein or synthetic protein/peptide for supplementation into the culture media. In further embodiments, the factor may be provided in a paracrine manner, e.g., wherein the factor is secreted from a different cell to the cell of interest. Still further, the factor may be provided in an autocrine fashion whereby the cell of interest is treated so as to induce expression/production of the factor (e.g., expression of a nucleic acid molecule or vector encoding the factor, by the cell of interest or source cell, as the case may be). It will also be understood that a combination of exogenous, paracrine and autocrine approaches to providing the factors may be utilised.

As used herein, "H3K4" modification refers to an epigenetic modification of chromatin which influences the regulation of gene expression. H3K4 refers to the addition of a methyl group to the lysine 4 on the histone H3 protein. Thus H3K4me3 refers to the addition of 3 methyl groups (trimethylation at the same lysine residue). The histone H3 protein is used to package DNA in eukaryotic cells and modifications to the histone alter the accessibility of genes for transcription. H3K4me3 is commonly associated with the activation of transcription of nearby genes. H3K4 trimethylation regulates gene expression through chromatin remodeling by the NURF complex. In bivalent chromatin, H3K4me3 can be co-localized with the repressive modification H3K27me3 to control gene regulation.

The methods of the present invention find utility in identifying factors for use in cell maintenance of a cell or collection of cells of interest, transdifferentiation, reprogramming, directed differentiation and/or conversion of source cells to target cells.

It will be understood that "maintaining the cell of interest in vitro" may include culturing the cell in cell culture conditions such that the cell retains is primary morphological and biophysical characteristics. This may be measured, for example, by confirming that the markers associated with a cell of interest are retained following several passages in cell culture. It will be understood that "maintaining the cell of interest" and "retaining primary morphological and biophysical characteristics" may include maintaining the viability of at least 50%, at least 60%, at least 70%, at least 80%, at least 90% or more of the cells in culture. Preferably, the cells are maintained for at least 2 days, at least 5 days, at least 10 days, at least 20 days, at least 30 days, at least 60 days or longer. Further, "retaining primary and biophysical characteristics" may be understood to mean that the cells maintained in culture according to the present methods, will retain at least 90%, at least 80%, at least 70%, at least 60% or at least 50% of the markers that are associated with the cell of interest. Preferably the cells will retain at least 70% of the markers during the period of culture. Further, "retaining primary and biophysical characteristics" may also be understood to mean that the cells maintained in culture according to the present methods, will retain at least 90%, at least 80%, at least 70%, at least 60% or at least 50% of the morphological properties that are associated with the cell of interest. Preferably the cells will retain at least 70% of the morphological properties associated with the cell of interest, during the period of culture.

It will be understood that the term "cell conversion" (for example, from a source cell to a target cell) can refer to dedifferentiation, transdifferentiation, reprogramming or directed differentiation.

As used herein, dedifferentiation refers to a method of reverting a terminally differentiated cell back to a less-differentiated stage from within its own lineage, which allows it to proliferate. Directed differentiation refers to the differentiation from a pluripotent cell state (e.g., a stem cell) to a differentiated target cell of a specific type.

Transdifferentiation typically refers to a process whereby a cell is modified to a point where it can switch lineages or can also occur directly between two different cell types.

Cell reprogramming typically refers to a process of reverting mature, specialised cells into induced pluripotent stem cells.

As used herein a cell of interest is any cell for which it is necessary to identify the factors (including receptor/ligand pairs, ligands, transcription factors or other agent) for maintaining the cell in vitro. The cell of interest may be any cell found in any of the three embryonic germ layers, i.e., the ectoderm, mesoderm and endoderm germ layers. As used herein, ectoderm refers to outer body tissue such as skin, nails; mesoderm refers to tissue such as muscle but also includes blood; endoderm refers to the inner lining such as digestive tract cells. Examples of various cells of interest are provided in Table 2. Examples of cells of interest derived from the mesoderm include cells of skeletal muscle, skeleton, dermis of skin, connective tissue, urogenital system, heart, blood (lymph cells), and spleen. Examples of cells derived from the endoderm include cells of the stomach, colon, liver, pancreas, urinary bladder; lining of urethra, epithelial parts of trachea, lungs, pharynx, thyroid, parathyroid, intestine. Examples of cells derived from the ectoderm include cells of the central nervous system, retina and lens, cranial and sensory, ganglia and nerves, pigment cells, head connective tissue, epidermis, hair, and mammary glands.

A "cell of interest" may include any cell that is suitable for being maintained in tissue culture. Non-limiting examples of a cell of interest include those cells listed in Table 2. More particularly, a "cell of interest" or "a source cell" as used herein may be a primary cell (non-immortalized cell), or may be a cell derived from a cell line (immortalized cell), or may be a tissue isolated from an individual. A cell of interest may also be a progenitor cell, for example a neural progenitor cell, haematopoietic progenitor cell, myogenic progenitor cell, endothelial progenitor cell, and a common lymphocyte or myeloid progenitor cell. A cell of interest may refer to a population of cells, for example a mixed population of cells such as a tissue or those obtained from a tissue. In some embodiments, a cell of interest or a source cell is an undifferentiated cell. In other embodiments, a cell of interest or a source cell is a transdifferentiated cell or transdifferentiating cell. A transdifferentiated cell is a cell that has been generated from the process of transdifferentiation i.e. changing the phenotype of a somatic cell to another somatic cell. "Somatic cells" as used herein are cells derived from one of the germ layers (ectoderm, endoderm or mesoderm). A transdifferentiating cell is a cell that is undergoing the process of transdifferentiation i.e. the phenotype of the somatic cell is changing towards the phenotype of another somatic cell wherein the markers of the final somatic cell have not yet been fully established. In other embodiments, a cell of interest or a source cell is a differentiated cell which is a specialised cell type.

As used herein, a source cell or cell of interest may be any cell type described herein, including a somatic cell or a diseased cell. The somatic cell may be an adult cell or a cell derived from an adult which displays one or more detectable characteristics of an adult or non-embryonic cell. Other examples of source cells include progenitor cells such as hematopoietic cell, e.g. lymphocyte, myeloid cell; a buccal mucosa cell, an epidermal cell, a mesenchymal cell, a keratinocyte, a hepatocyte, embryonic cell, stem cell or cell that has been treated to have one or more characteristics of a stem cell. In the case of diseased cells, the diseased cell may be a cell displaying one or more detectable characteristics of a disease or condition, for example the diseased cell may be a cancer cell displaying one or more clinical or biochemical markers of a cancer.

The source cell or cell of interest may also be a stem cell, including a pluripotent stem cell, preferably induced pluripotent stem cell (iPSC).

As used herein, the term "somatic cell" refers to any cell forming the body of an organism, as opposed to germline cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro. The somatic cells may be immortalized to provide an unlimited supply of cells, for example, by increasing the level of telomerase reverse transcriptase (TERT). For example, the level of TERT can be increased by increasing the transcription of TERT from the endogenous gene, or by introducing a transgene through any gene delivery method or system.

Unless otherwise indicated the methods for conversion of somatic cells can be performed both in vivo and in vitro (where in vivo is practised when somatic cells are present within a subject, and where in vitro is practised using isolated somatic cells maintained in culture).

An embryonic cell, such as an embryonic stem cell, may be a cell derived from an embryonic cell line and not directly derived from an embryo or fetus. Alternatively, the embryonic cell may be derived from an embryo or fetus however the cell is obtained or isolated without destruction of, or any negative influence on the development of, the embryo or fetus.

The present invention also contemplates the use of induced pluripotent stem cells (iPSCs).

Differentiated somatic cells, including cells from a fetal, newborn, juvenile or adult primate, including human, individual, are suitable source cells (or cells of interest) in the methods of the invention. Suitable somatic cells include, but are not limited to, bone marrow cells, epithelial cells, endothelial cells, fibroblast cells, hematopoietic cells, keratinocytes, hepatic cells, intestinal cells, mesenchymal cells, myeloid precursor cells and spleen cells. Alternatively, the somatic cells can be cells that can themselves proliferate and differentiate into other types of cells, including blood stem cells, muscle/bone stem cells, brain stem cells and liver stem cells. Suitable somatic cells are receptive, or can be made receptive using methods generally known in the scientific literature, to uptake of transcription factors including genetic material encoding the transcription factors. Uptake-enhancing methods can vary depending on the cell type and expression system. Exemplary conditions used to prepare receptive somatic cells having suitable transduction efficiency are well-known by those of ordinary skill in the art. The starting somatic cells can have a doubling time of about twenty-four hours.

The term "isolated cell" as used herein refers to a cell that has been removed from an organism in which it was originally found or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein, refers to a population of cells that has been removed and separated from a mixed or heterogeneous population of cells. In some embodiments, an isolated population is a substantially pure population of cells as compared to the heterogeneous population from which the cells were isolated or enriched.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a population of target cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not target cells or their progeny as defined by the terms herein.

As used herein, reference to a "target cell" may be a reference to any one or more of the cells referred to herein as target cells or target cell types.

The target cells may be cells representing any of three embryonic germ layers, i.e., endoderm, mesoderm, and ectoderm. For example, the target cells be cells that are typically found in skeletal muscle, skeleton, dermis of skin, connective tissue, urogenital system, heart, blood (lymph cells), and spleen (mesoderm); stomach, colon, liver, pancreas, urinary bladder; lining of urethra, epithelial parts of trachea, lungs, pharynx, thyroid, parathyroid, intestine (endoderm); or central nervous system, retina and lens, cranial and sensory, ganglia and nerves, pigment cells, head connective tissue, epidermis, hair, mammary glands (ectoderm).

A source cell is determined to be converted to a target cell, or become a target-like cell, by a method of the invention when it displays at least one characteristic of the target cell type. For example, a human fibroblast will be identified as converted to a keratinocyte-like cell, when a cell displays at least one characteristic of the target cell type. Typically, a cell will display 1, 2, 3, 4, 5, 6, 7, 8 or more characteristics of the target cell type. For example, where the target cell is a keratinocyte cell, a cell is identified or determined to be a keratinocyte-like cell when up-regulation of any one or more keratinocyte markers and/or change in cell morphology is detectable, preferably, the keratinocyte markers include keratin1, keratin14 and involucrin and the cell morphology is cobblestone appearance. In any aspect of the invention, the target cell characteristic may be determined by analysis of cell morphology, gene expression profiles, activity assay, protein expression profile, surface marker profile, or differentiation ability. Examples of characteristics or markers include those that are described herein and those known to the skilled person. Other examples of relevant markers include, for example for a conversion of keratinocytes to haemopoietic stem cells (HSC): CD45 (pan haematopoietic marker), CD19/20 (B-cell markers), CD14/15 (myeloid), CD34 (progenitor/SC markers), CD90 (SC) and alpha-integrin (keratinocyte marker not expressed by HSC); for human embryonic stem cells to haemopoietic stem cells: Runx1 (GFP), CD45 (pan haematopoietic marker), CD19/20 (B-cell markers), CD14/15 (myeloid), CD34 (progenitor/SC markers), CD90 (SC), Tra-1-160 (ESC marker not expressed in HSC); for rejuvenation of aged or adult HSC: a comparison between the transcriptional signatures of young and aged human HSC (e.g. using RNA-seq), and functional characterisation of "rejuvenated HSC" by transplanting rejuvenated cells into animals then assessed after 1, 3 and 6 months to determine the myeloid bias, wherein a disappearance of the myeloid bias indicates "rejuvenated" HSC. Examples of markers for many of the conversions described herein are shown in Table 1 below.

TABLE 1

Exemplary markers for cells of interest or target cells

| Target cell | Marker |
|---|---|
| Astrocytes | GFAP, S100B, ALDH1L1, CD44, GLAST1 |
| Chondrocytes | CD49. CD10, CD9, CD95, Integrin α10β1, 105 and Production of sulphated glycosamino-glycans (GAG) |
| Epithelial cells | cytokeratin 15 (CK15), cytokeratin 3 (CK3), involucrin and connexin 4. |
| Endothelial cells (such as aortic endothelial cells) | VEGFR2, VE-Cadherin, Pe-CAM (CD31), VWF |
| Hair follicles | CD200, PHLDA1, follistatin |
| Keratinocytes | Pan-keratin, Keratin 14, Keratin 1, involucrin |

TABLE 1-continued

Exemplary markers for cells of interest or target cells

| Target cell | Marker |
|---|---|
| CD4+ T-cell | CD3, CD4 |
| CD8+ T-cell | CD3, CD8 |
| NK-cell | CD56, CD2 |
| HSCs | CD45 (pan haematopoietic marker), CD19/20 (B-cell markers), CD14/15 (myeloid), CD34 (progenitor/SC markers), CD90 (SC) |
| MSCs of adipose | CD13, CD29, CD90, CD105, CD10, CD45-and differentiate in vitro towards osteoblasts, adipocytes and chondrocytes |
| MSCs of bone marrow | CD13, CD29, CD90, CD105, CD10, and differentiate in vitro towards osteoblasts, adipocytes and chondrocytes |
| Oligodendrocytes precursor | NG2 and PDGFRα QPCR for Olig2 and Nkx2.2 |
| Skeletal muscle cell | MyoD, Myogenin and Desmin |
| Smooth muscle cell | Myocardin, Smooth Muscle Alpha Actin (ACTA2/α-SMA), Smooth muscle myosin heavy chain, TAGLN/SM22 |
| Fetal cardiomyocytes cardiomyocytes | MEF2C, MYH6, ACTN1, CDH2 and GJA1 SIRPA, GATA4, NKX2.5, CD82, CD13, cardiac troponin T (cTNT) |
| Pluripotent stem cells | SSEA-4, TRA-1-60, OCT4 |

TABLE 2

Cell identity/maintenance factors identified for various cells

| Cell or tissue type | Cell identity factors |
|---|---|
| | Primary cells: |
| astrocytes | FN1, COL4A1, LAMB1, ADAM12, WNT5A, COL1A2, EDIL3 |
| cardiomyocytes | FN1, COL3A1, TFPI, FGF7, APOE, C3, COL1A2, SERPINE1, COL6A3, CXCL12 |
| smooth muscle cells | LAMA5, COL4A1, LAMA4, NID1, COL6A3, COL4A6, COL4A5, FGF10, FGF7, GNAS, COL7A1, COL1A1 and THBS1. |
| endothelial cells (e.g., from aorta) | MP6, ADAM9, LAMB1, LAMA4, THBS1, CTGF, BMP4, PDGFB, FN1 and CYR61 |
| astrocyte of the cerebellum | WNT5A, WNT7B, FN1, PLAU, GDF5, COL6A3, BMP4, SFRP1, LAMB1, VEGFC, EFNA1, WNT11, COL5A1, COL1A2, COL4A6, COL4A5, CYR61, COL1A1, SEMA3B, VCAN, THBS1, ADAM9, LAMC1, CALR, VEGFA, VEGFB, TNFSF13 |
| astrocyte of the spinal cord | WNT5A, NRG1, COL4A1, FN1, GDF5, TGFB3, COL6A3, PDGFC, PLAU, COL3A1, WNT7B, COL1A2, BMP4, VEGFC, COL5A1, TGFB2, IGFBP4, FBN1, VCAN, LAMB1, COL1A1, ADAM9, WNT11, COL8A1, THBS1, SEMA3A, CYR61, SLIT2, LAMC1, VEGFA, LAMA5, CALR, EFNA1, SEMA3B, VEGFB, TNFSF13 |
| astrocyte | FN1, COL4A1, LAMB1, ADAM12, WNT5A, COL1A2, EDIL3, COL5A1, SERPINE1, COL6A2, FBN1, ADAM9, PDGFA, PLAU, VCAN, THBS1, GAS6, LAMC1, SEMA3A, CYR61, COL1A1, NRG1, CALR, TNFSF13, VEGFB, SEMA3B |
| brain microvascular endothelial cell | FN1, COL4A1, SERPINE1, COL3A1, WNT5A, PDGFA, COL1A1, PDGFC, COL6A1, COL1A2, COL7A1, COL5A1, LAMB1, PLAU, CTGF, IGFBP4, FBN1, VCAN, CYR61, ADAM9, THBS1, LAMA5, MDK, VEGFA, CALR, SEMA3B, LAMC1, VEGFB, C3, EFNA1, BMP4 |
| cardiac muscle cell | FN1, COL3A1, TFPI, FGF7, APOE, C3, COL1A2, SERPINE1, COL6A3, CXCL12, LAMB1, TGFB3, LAMC1, EFNA1, COL1A1, MDK, TGFB2, ICAM4, COL5A1, GDF5, THBS1, PDGFA, IGFBP4, VEGFA, SLIT2, ADAM9, VCAN, INHBA, WNT11, SEMA3B, BMP4, CALR, C1QTNF5, VEGFB, LAMA5, CLCF1, TNFSF13 |
| chloroid plexus epithelial cell | FN1, COL1A2, COL11A1, COL3A1, COL4A1, GDF5, COL1A1, LAMB1, IGFBP4, COL8A1, COL4A6, COL4A5, ADAM9, FBN1, WNT5A, PDGFA, COL7A1, CTGF, SLIT2, BMP4, GNAS, EFNA1, LAMC1, LAMA5, C3, SEMA3B, TNFSF13, CALR, VEGFB |
| cortex derived neurospheres | BMP7, NXPH1, PTN, TNC, MDK, NRG1, GNAS, COL11A1, BMP4, VEGFA, KITLG, EFNA1, WNT11, BDNF, WNT5A |
| endothelial cell of umbilical vein | BMP6, ADAM9, LAMB1, LAMA4, THBS1, CTGF, BMP4, PDGFB, FN1, CYR61, EFNA1, SLIT2, COL4A1, TGFB2, LAMA5, INHBA, VEGFB, SEMA3B, ADM |
| epithelial cell of esophagus | LAMB3, LAMA5, COL4A6, COL4A5, AMH, COL7A1, VEGFA, EFNA1, SEMA3F, HMGB1, CALR, SEMA3B |

TABLE 2-continued

| Cell identity/maintenance factors identified for various cells | |
| --- | --- |
| Cell or tissue type | Cell identity factors |
| epithelial cell of proximal tubule | SPP1, PDGFC, EFNA1, WNT7B, TNFSF10, PLAU, LAMB1, NRG1, COL4A1, LAMC1, LAMA5, PDGFA, TFPI, VEGFB, SEMA3B, GNAS, VEGFA, C3, CALR, TNFSF13, WNT5A |
| fibroblast of arm | COL1A2, FN1, COL3A1, COL1A1, THBS1, FGF7, COL6A3, SEMA3A, VEGFC, CYR61, FGF2, LAMA4, LAMC1, PDGFC, FBN1, COL6A2, SERPINE1, SEMA3C, COL5A2, SERPINE2, GNAS, GAS6, VCAN, COL5A1, ADAM9, VEGFA, CALR, SEMA3B, VEGFB, WNT5A, TNFSF13 |
| fibroblast of dermis | SEMA3A, COL3A1, COL6A3, FGF7, LAMC1, COL6A2, SLIT3, COL6A1, NRG2, SLIT2, FBN1, LAMA4, COL1A2, CYR61, SERPINE2, THBS1, FN1, FGF2, COL4A1, COL1A1, ADAM9, VCAN, VEGFA, COL8A1, VEGFB, CALR, GNAS, WNT5A, TNFSF13 |
| fibroblast of gingiva | SEMA3A, FGF7, PGF, THBS1, IGF2, COL1A1, COL1A2, COL3A1, GAS6, FGF2, CXCL12, NRG1, OL6A3, C3, WNT5A, SEMA3B, COL6A1, GNAS, COL5A1, PLAU, COL6A2, VEGFC, SLIT2, VEGFA, TIMP2, FBN1, VEGFB, VCAN, PDGFA, CYR61, TNFSF13, CALR, ADAM9, LAMC1, LAMA5, CLCF1 |
| fibroblast of mammary gland | COL3A1, FGF7, COL1A1, COL6A3, FN1, TGFB3, COL6A1, COL6A2, FBN1, CYR61, THBS1, GDF5, COL1A2, LAMC1, VEGFA, WNT5A, ADAM9, CALR, VEGFB, SEMA3B, TNFSF13 |
| fibroblast of pedal digit skin | COL1A1, THBS1, NRG1, COL3A1, COL1A2, COL6A1, COL6A3, GDF5, COL6A2, COL5A1, FGF2, WNT5A, FN1, SLIT2, FST, CYR61, VEGFC, COL8A1, COL5A2, FBN1, C3, BMP4, LAMC1, IGFBP4, VEGFA, PDGFA, SEMA3B, ADAM9, CALR, CLCF1, LAMA5, VEGFB, TNFSF13 |
| fibroblast of pulmonary artery | FN1, COL3A1, LAMB1, COL6A3, TFPI, COL1A2, SERPINE1, COL4A6, COL4A5, C3, LAMC1, GDF5, COL4A1, BMP6, SLIT2, FBN1, COL1A1, THBS1, EFNA1, VCAN, TGFB2, CTGF, ADAM9, INHBA, LAMA5, BMP4, CALR, TNFSF13, CLCF1, SEMA3B, VEGFB |
| fibroblast of skin of abdomen | THBS1, SEMA3A, FGF7, GAS6, COL1A1, COL1A2, COL3A1, SERPINE2, NRG1, COL6A2, COL6A1, CXCL12, COL6A3, FBN1, CYR61, GNAS, FGF2, FN1, COL5A1, TIMP2, SEMA3B, IL6, COL8A1, VEGFC, VEGFA, VEGFB, WNT5A, CALR, LAMC1, EFNA1, TNFSF13, SLIT2 |
| fibroblast of the aortic adventitia | NRG1, COL1A1, SERPINE2, FGF7, COL3A1, PLAT, C3, COL1A2, COL6A3, FBLN1, LAMC1, FN1, IGFBP4, FGF2, FBN1, COL5A1, VEGFA, SEMA3B, INHBA, VEGFC, GAS6, TGFB2, SLIT2, VEGFB, THBS1, VCAN, ADAM9, CYR61, CALR, GNAS, WNT5A, EFNA1, C1QTNF5, LAMA5, TNFSF13, HMGB1 |
| fibroblast of upper leg skin | NRG1, GAS6, WNT5A, COL1A1, COL1A2, THBS1, COL6A3, CXCL12, CYR61, VEGFA, COL6A1, FBN1, COL6A2, COL7A1, COL3A1, COL5A1, FGF2, VEGFC, COL4A1, FN1, SEMA3B, ADAM9, VEGFB, C3, LAMC1, CALR, COL8A1, EFNA1 |
| fibroblast of villous mesenchyme | IGF2, ANGPT1, COL3A1, COL1A1, COL4A1, PLAT, LAMB1, COL5A2, COL1A2, TFPI, FBLN1, COL5A1, FGF7, COL6A3, COL6A1, COL8A1, GAS6, COL6A2, FBN1, COL4A6, COL4A5, PDGFA, FN1, LAMC1, MDK, LAMA5, CYR61, WNT5A, THBS1, INHBA, VEGFB, CLCF1, CALR, DKK1, EFNA1, GNAS, SEMA3B |
| foreskin fibroblast | COL7A1, COL1A1, LAMA5, COL6A1, GAS6, NRG1, COL6A2, COL1A2, FBLN1, CLCF1, VEGFA, VEGFC, THBS1, FN1, C3, CALR |
| foreskin melanocyte | TNFSF13 |
| ganglionic eminence derived neurospheres | NXPH1, PTN, FGF9, MDK, SAP, PDGFC, NRG1, SLIT2, LAMC1, CALR, EFNA1, VEGFA, WNT5A, VEGFB, SEMA3B, BDNF |
| HFF.Myc | COL6A3, GAS6, COL3A1, COL1A1, COL6A1, SEMA3A, COL6A2, LAMB1, THBS1, WNT5A, PLAU, SLIT2, WNT11, NRG1, COL1A2, ADAM9, CALR, FGF2, C3, VEGFB, LAMA5, GNAS, CYR61, EFNA1, TNFSF13, SEMA3B |
| IMR.90 | COL6A3, COL3A1, VEGFC, COL1A2, BDNF, WNT5A COL5A2, GAS6, TFPI, COL6A2, FGF7, COL4A1, THBS1, PLAU, COL1A1, COL4A6, COL4A5, SEMA3A, COL7A1, CYR61, FN1, VCAN, ADAM9, IGFBP4, LAMC1, VEGFA, FST, BMP4, SEMA3B, GNAS, TNFSF13, CALR, VEGFB |
| mammary epithelial cell | LAMB3, NRG1, PLAU, LAMA5, EFNA1, THBS1, COL7A1, AMH, TGFB2, HMGB1, CYR61, CALR, SEMA3B |
| myoepithelial cell of mammary gland | LAMB3, COL18A1, LAMC2, HBEGF, COL4A1, NRG2, THBS1, NRG1, TNFSF13, VEGFA, PDGFA, ANXA1, C3, LAMC1, EFNA1, FGF9, FGF2, SEMA3C, CYR61, LTA, TNF, PDGFB, LAMA5, CALR, AMH, WNT5A |
| | Stem cells |
| ES.I3 | SPP1, VCAN, MP4, LAMC1, LAMA5, FGF2, EFNA1 EFEMP2, C3, SEMA3B, TNFSF13, CLCF1 |

TABLE 2-continued

| Cell identity/maintenance factors identified for various cells | |
|---|---|
| Cell or tissue type | Cell identity factors |
| H1.hESC | FGF2, LAMA5, MDK, C3, PDGFA, VEGFB, TDGF1, EFEMP2, EFNA1, LAMB1, TNFSF13, CALR |
| H7.hESC | TDGF1, CLCF1, EFEMP2, C3, BMP4, FST |
| H9 | FGF2, LAMA5, MDK, SEMA3B, PDGFA, VEGFB, VCAN, EFEMP2, COL1A, LAMB1, TNFSF13, CALR |
| HUES48 | FGF2, PDGFA, VCAN, MDK, TDGF1, BMP4, C3, LAMA5, EFEMP2 |
| HUES64 | VEGFB NRG1, EFNA1, COL4A6, COL4A5, TFPI, MDK, PDGFA, LAMA5, TDGF1, C3, SEMA3B, COL1A2, EFEMP2 |
| HUES6 | FGF8, COL4A6, COL4A5, MDK, FGF2, COL4A1, NRG1, SEMA3B, TDGF1, BMP4, SEMA3A, LAMA5, COL7A1, PDGFA, C3, EFNA1, EFEMP2, TNFSF13, CLCF1 |
| | Tissue |
| adrenal gland | LAMA2, VEGFA, C3, VEGFB, INHBE, CALR |
| amnion | IGF2, WNT5A, COL1A1, FN1, INHBA, SLIT2, CYR61, COL3A1, VEGFA, EFNA1, NTN3, LAMA5, BMP4, MGB1 |
| angular gyrus | GNAS, FGF9, NRG1, EFEMP2, EFNA1, SEMA3B, WNT5A, VEGFB, TNFSF13 |
| aorta | FN1, CTGF, CYR61, INHBA, COL3A1, VCAN, COL5A2, COL8A1, COL5A1, NTF3, LAMC1, CNTN4, COL4A1, ADAM9, FST, BMP4, GNAS, EFEMP2 |
| ascending aorta | CYR61, SERPINE1, MFGE8, FN1, PDGFC, PDGFA, COL8A1, FBN1, COL4A1, LTBP1, TGFB3, LAMA5, COL1A2, INHBA, LAMC1, THBS1, COL3A1, TIMP2, A2M, TGFB2, BDNF, BMP4, LTBP3, GNAS, EFNA1, CALR, EFEMP2, HMGB1, TNFSF13, IGFBP4, VEGFB, SEMA3B |
| caudate nucleus | SEMA3B, C3, VEGFB, COL4A5, NRG1, RELN, PDGFA, CALR, WNT5A, LAMA5, TNFSF13 |
| cingulate gyrus | FGF9, GNAS, GDNF, SEMA3B, EFEMP2 |
| colonic mucosa | MDK, TNFSF13, C3, THBS1, WNT5A, GNAS, CALR |
| coronary artery | LAMA2, LAMA5, COL18A1, COL4A1, GAS6, COL3A1, INHBE, COL1A2, FBLN1, PDGFA, LAMC1, PDGFC, COL8A1, FGF1, MFGE8, ANGPT1, COL1A1, SEMA3B, TFPI, FGF7, FBN1, INHBA, C1QA, FN1, COL4A2, BGN, C3, COL5A1, TIMP2, THBS1, ICAM4, A2M, TGFB3, NID1, GNAS, SEMA3F, BDNF, CYR61, TNFSF13, EFNA1 |
| duodenal mucosa | IL16, EFNA1, MDK, ICAM4, VEGFB, TNFSF13, SEMA3B, HMGB1 |
| esophagus muscularis mucosa | LAMA5, LAMA2, COL4A6, COL4A5, FGF7, LAMA4, LAMC1, THBS1, NID1, COL4A1, COL3A1, FBLN1, CYR61, C3, FN1, PDGFB, GNAS, COL1A2, SEMA3B, PDGFA, ICAM4, COL6A3, INHBA, SEMA3A, IL16, TIMP2, VWF, SEMA3G, A2M, WNT5A, TGFB2, TNFSF13, BMP4, CLCF1, FGF9, CALR, EFNA1, SLIT2 |
| esophagus | SEMA3F, LAMA5, EFNA1, VEGFA, SEMA3B |
| esophagus squamous epithelium | LAMA5, LAMA2, SPON2, C3, COL3A1, TFPI, A2M, VWF, NID1, IL16, BMP7, ICAM4, WNT5A, PDGFA, TNFSF13, CYR61, COL4A1, COL6A3, FBLN1, LAMC1, LAMA4, FGF7, THBS1, GNAS, CALR, EFNA1, INHBE, SEMA3F, SEMA3G, HMGB1, INHBA |
| gastrocnemius medialis | VWF, GNAS, VEGFA, LAMA2, LAMC1, LAMA5, TGFB2, COL3A1, WNT5A, CYR61, VEGFB, TNFSF13, EFEMP2, SEMA3B |
| gastroesophageal sphincter | LAMA2, COL4A6, COL4A5, LAMA5, LAMA4, COL18A1, NID1, FBN1, COL4A1, FGF7, TIMP2, FBLN1, CYR61, COL6A3, FN1, GNAS, THBS1, C3, SEMA3A, INHBA, PDGFA, ICAM4, FGF2, A2M, VWF, LAMC1, COL3A1, TGFB2, FGF9, SEMA3B, CLCF1, EFNA1, SLIT2, WNT5A, CALR, INHBE |
| germinal matrix | SLIT1, NXPH1, NRG1, VCAN, NRG3, SFRP1, AMH, WNT5A, FGF9, BMP7, INHBB, VEGFA, AGRN, EFEMP2, BDNF, EFNA1, SEMA3B |
| kidney | GPC3, CTGF, RSPO3, GDNF, SLIT2, LAMB1, COL1A2, SEMA3A, FST, COL3A1, THBS1, LAMC1, WNT5A, VCAN, COL4A1, EFNA1, VEGFA, BMP4, VEGFB |
| large intestine | LAMB3, TNFSF13, MDK, VEGFB, VEGFA, C3, SEMA3B |
| layer of hippocampus | BDNF, C3, GNAS, A2M, FGF9, EFEMP2, EFNA1, SEMA3B, WNT5A, TNFSF13, CALR, VEGFB |
| middle frontal area 46 | FGF9, GNAS, VEGFA, C3, SEMA3B, EFNA1, CALR, VEGFB |
| mucosa of rectum | LTA, EFNA1, THBS1, TNFSF13, GNAS |
| muscle layer of colon | COL4A1, COL6A3, NID1, FGF7, TNC, OL5A1, FGF2, COL3A1, LAMB1, TIMP2, THBS1, COL1A1, LAMA4, LAMC1, LAMA5, C3, IGFBP4, ANXA1, CYR61, A2M, EFNA1, TNFSF13, BMP4, CALR, SEMA3B, VEGFB |
| muscle layer of duodenum | COL3A1, TNFSF13, TIMP2, THBS1 |
| muscle of leg | COL1A1, BMP5, COL1A2, COL5A1, COL3A1, COL4A1, GNAS, COL4A2, LAMC1, EFNA1 |

TABLE 2-continued

| Cell or tissue type | Cell identity factors |
|---|---|
| muscle of trunk | EFNA1 |
| ovary | PDGFD, NRG2, NDP, COL4A6, INHBA, LAMA2, WNT5A, FGF7, COL6A3, FGF2, COL3A1, NTF3, FBN1, BDNF, CYR61, COL5A1, COL4A1, NTN3, THBS1, LAMC1, WNT11, PDGFA, MDK, SLIT2, TGFB2, BMP4, IGFBP4, TNFSF13, LAMA5, FST, TGFB3, EFEMP2 |
| Peyer's patch | EFNA1, PDGFA, MDK, APOB, NID1, TNFSF13, LAMA5, VEGFB, CYR61, HMGB1, SEMA3B, C3 |
| placenta | PGF, EBI3, PDGFB, INHBA, TGFB3, GNAS, VEGFB, LAMA5, FST, HMGB1, BMP4 |
| psoas muscle | TGFB3 |
| rectal smooth muscle tissue | TNC, IL16, FGF7, COL4A1, EFNA1, COL3A1, THBS1, WNT5A, TGFB3, GNAS, ADM2, FGF9, SEMA3B, CALR, CYR61, C3, TNFSF13, VEGFB |
| right atrium auricular region | LAMA2, COL1A2, NID1, COL4A6, COL4A5, FGF7, COL4A1, VWF, FN1, THBS1, COL3A1, CYR61, FBN1, COL6A3, PDGFA, LAMC1, VEGFA, COL8A1, LAMA5, WNT5A, TGFB3, TGFB2, BMP4, IGFBP4, EFNA1, CALR, VEGFB, SEMA3B, EFEMP2, TNFSF13 |
| sigmoid colon | FGF7, THBS1, COL6A3, COL3A1, SEMA3A, TGFB3, IGFBP4, FGF9, BMP4, C3, VEGFB, SEMA3B,, TNFSF13 |
| small intestine | MDK, TNFSF13, SERPINA1, EFNA1, VEGFA, C3, CALR |
| spleen | IL16, LTA, TNF, B2M, TGFB1, EFNA1, TNFSF10, GNAS, TNFSF13 |
| stomach | TNFSF13, COL1A1, THBS1, EFNA1, LAMC1, C3 |
| stomach smooth muscle | LAMA5, COL4A1, LAMA4, NID1, COL6A3, COL4A6, COL4A5, FGF10, FGF7, GNAS, COL7A1, COL6A2, COL1A1, THBS1, COL18A1, COL5A1, FBLN1, TIMP2, BMP4, IGFBP4, CALR, SEMA3B, A2M, EFNA1, FGF9, TNFSF13, WNT5A |
| subcutaneous abdominal adipose tissue | ICAM4, GNAS, TIMP2, LAMA4, ADAM9, TNFSF13, IL16, COL4A1, C3, LAMC1, SEMA3B, COL3A1, C1QA, FGF7, EFNA1, CALR, INHBE, COL4A2, SEMA3G, VEGFB |
| temporal lobe | FGF1, BDNF, EFNA1, GNAS, FGF9, NRG1, SEMA3B, EFEMP2, VEGFB, TNFSF13, C3 |
| thoracic aorta | PDGFC, SERPINE1, GNAS, FN1, LTBP1, LAMA5, ANGPT1, COL4A1, COL3A1, COL1A2, TIMP2, COL18A1, GAS6, EDIL3, ADAM9, COL8A1, LAMC1, BGN, LTBP3, A2M, PDGFA, FBN1, BDNF, CYR61, ICAM4, TGFB3, C3, CALR, TNFSF13, SEMA3B, EFNA1, EFEMP2 |
| thyroid gland | EFNA1, GNAS, VEGFA, PDGFB, CYR61, IGFBP4, CALR, BMP4, TGFB3, LAMA5, WNT5A, VEGFB, TNFSF13, SEMA3B, HMGB1 |
| tibial nerve | COL18A1, COL4A1, THBS1, LAMA2, LAMB1, IGFBP4, TGFB3, SEMA3B, LAMC1, EFNA1, C3, CALR, TNFSF13, HMGB1, VEGFB, GNAS |
| vagina | FBLN1, COL1A2, COL1A1, COL3A1, FBN1, COL6A3, GDF7, CYR61, PDGFA, TIMP2, FGF7, COL4A1, THBS1, LAMA5, SLIT2, TGFB2, TGFB3, EFNA1, C3, CALR, SEMA3B, BMP4, VEGFA, TNFSF13, HMGB1, VEGFB |

In particular embodiments, one, two, three, four, or five or more of the factors (ligands) listed in Table 2 are added, or used to contact the cell of interest in order to maintain the cell of interest in vitro. In other embodiments, six, seven, eight, nine, 10, 11, 12, 13, 14, 15 or more, 20 or more, 25 or more, 30 or more or 35 or more of the factors (ligands) listed in Table 2 are added to the cell of interest or used to contact the cell of interest.

The present invention also provides methods for conversion of a source cell to a target cell. Methods for identifying factors for use in such a conversion are further explained herein. Further to the embodiments outlined elsewhere in this document, in certain embodiments, the source cell is an embryonic stem cell and the factors for converting the embryonic stem cell to a target cell are as provided in the following table:

TABLE 3

Factors for differentiation/conversion of H9 embryonic stem cells to various target cell types

| Target cell or tissue type | Cell conversion factors |
|---|---|
| Primary cells: | |
| astrocyte of the cerebellum | WNT5A, WNT7B, GDF5, FN1, BMP4, SFRP1, EFNA1, COL1A2, VEGFA |
| astrocyte of the spinal cord | WNT5A, GDF5, FN1, TGFB3, COL4A1, WNT7B, COL6A3, BMP4, COL1A2, TGFB2, COL5A1, COL8A1, SEMA3A, VEGFA, LAMC1 |
| astrocyte | FN1, COL4A1, EDIL3, WNT5A, COL1A2, ADAM12, SERPINE1, |

TABLE 3-continued

| Target cell or tissue type | Cell conversion factors |
|---|---|
| | LAMB1, COL5A1, FBN1, ADAM9, COL6A2, PLAU, LAMC1, GAS6, THBS1, SEMA3A, CYR61 |
| brain microvascular endothelial cell | FN1, WNT5A, COL4A1, PLAU, COL6A1, COL1A2, COL5A1, ADAM9, VEGFA, LAMB1, THBS1, LAMC1, BMP4, COL1A1 |
| cardiac muscle cell | FGF7, COL1A2, TGFB3, COL6A3, EFNA1, TGFB2, GDF5, LAMC1, C3, LAMB1, COL5A1, VEGFA, BMP4 |
| chloroid plexus epithelial cell | COL1A2, GDF5, COL4A1, COL8A1, WNT5A, COL4A5, COL4A6, BMP4, LAMB1, LAMC1, C3 |
| cortex derived neurospheres | BMP7, NXPH1, PTN, TNC, COL11A1, BMP4, KITLG, EFNA1 |
| endothelial cell of umbilical vein | BMP6, CTGF, BMP4, ADAM9, FN1, EFNA1, PDGFB, SLIT2, LAMA4, THBS1, CYR61, LAMB1, TGFB2, COL4A1 |
| epithelial cell of esophagus | LAMB3, VEGFA, EFNA1, LAMA5 |
| epithelial cell of proximal tubule | TNFSF10, EFNA1, WNT7B, PLAU, SPP1, COL4A1, LAMC1, LAMB1, C3, VEGFA |
| fibroblast of arm | COL1A2, FGF7, FN1, SEMA3A, COL3A1, THBS1, COL6A3, CYR61, VEGFC, COL1A1, LAMA4, LAMC1, FBN1, SEMA3C, COL6A2, SERPINE1. COL5A2, GAS6, COL5A1. VEGFA, FGF2, ADAM9, SERPINE2, CALR |
| fibroblast of dermis | SEMA3A, COL3A, FGF7, SLIT3, SLIT2, COL6A3, LAMC1, COL6A2, COL6A1, CYR61, FN1, COL1A, , VEGFA, COL8A1, THBS1, COL4A1 |
| fibroblast of gingiva | SEMA3A, FGF7, PGF, COL3A1, COL1A1, COL1A2, GAS6, THBS1, COL6A3, SLIT2, C3, VEGFA, COL6A1, PLAU, COL5A1, COL6A2, FGF2, CLCF1, LAMC1 |
| fibroblast of mammary gland | COL3A1, FGF7, FN1, FBN1, GDF5, TGFB3, COL1A2, VEGFA, WNT5A |
| fibroblast of pedal digit skin | COL3A1, THBS1, COL1A2, GDF5, COL1A1, FN1, COL6A1, COL6A3, FST, COL8A1, SLIT2, COL6A2, COL5A1, WNT5A, CYR61, BMP4, COL5A2, VEGFA, LAMC1, CLCF1, C3 |
| fibroblast of pulmonary artery | COL3A1, , GDF5, BMP6, C3, COL6A3, LAMB1, COL1A2, TGFB2, EFNA1, COL4A5, COL4A6, LAMC1, COL4A1, BMP4, CLCF1 |
| fibroblast of skin of abdomen | SEMA3A, FGF7, GAS6, COL3A1, COL1A1, COL1A2, CXCL12, THBS1, FN1, COL8A1, COL6A2, IL6, COL6A1, COL6A3, SERPINE2, CYR61, VEGFA, WNT5A, COL5A1, LAMC1 |
| fibroblast of the aortic adventitia | COL3A1, COL1A1, FGF7, COL1A2, SERPINE2, PLAT, FN1, C3, VEGFA, GAS6, COL6A3, TGFB2, LAMC1, CYR61, WNT5A, INHBA, COL5A1, THBS1, HMGB1 |
| fibroblast of upper leg skin | GAS6, WNT5A, COL1A2, VEGFA, COL6A3, COL3A1, COL6A1, COL6A2, CYR61, COL5A1, FN1, COL4A1, COL8A1, COL1A1, LAMC1, C3 |
| fibroblast of villous mesenchyme | IGF2, COL4A1, COL5A2, TFPI, COL1A2, COL5A1, FGF7, COL8A1, COL6A3, COL6A1, GAS6, COL6A2, LAMB1, COL1A1, COL4A5, COL4A6, LAMC1, CLCF1, CYR61, FN1, DKK1 |
| foreskin fibroblast | GAS6, CLCF1, COL7A1, COL1A2, COL6A1, COL6A2, FN1, C3, FBLN1, THBS1, COL1A1, LAMA5, VEGFA, VEGFC, CALR |
| ganglionic eminence derived neurospheres | NXPH1, PTN, SLIT2, PSAP, EFNA1, LAMC1, VEGFA, CALR |
| HFF.Myc | GAS6, SEMA3A, COL6A3, THBS1, COL6A1, COL6A2, PLAU, COL1A2, C3, COL1A1, LAMB1, CALR |
| IMR.90 | BDNF, COL6A3, COL3A1, COL1A2, WNT5A, COL5A2, COL6A2, COL4A1, FGF7, THBS1, GAS6, COL4A5, COL4A6, TFPI, SEMA3A, FN1, FST, LAMC1, BMP4, CYR61, VEGFA |
| mammary epithelial cell | LAMB3, EFNA1, THBS1, PLAU, TGFB2, COL7A1 |
| myoepithelial cell of mammary gland | LAMB, HBEGF, LAMC2, COL18A1, COL4A1, VEGFA, THBS1, C3, ANXA1, EFNA1, NRG1, LAMC1, SEMA3C, CYR61, TNFSF13, CALR, CLCF1 |

Tissue

| | |
|---|---|
| adrenal gland | LAMA2, VEGFA, C3 |
| amnion | WNT5A, FN1, COL1A1, COL3A1 |
| angular gyrus | EFNA1, WNT5A |
| aorta | FN1, CTGF, CYR61, COL8A1, CNTN4, NTF3, INHBA, COL3A1, COL5A2, COL5A1, LAMC1 |
| ascending aorta | SERPINE1, FN1, MFGE8, CYR61, PDGFC, COL8A1, FBN1, LTBP1, TGFB3, COL4A1, COL1A2, TGFB2, LAMC1, PDGFA, THBS1, INHBA, TIMP2, BDNF, BMP4, COL3A1, HMGB1 |
| caudate nucleus | C3, NRG1 |
| cingulate gyrus | GDNF |
| colonic mucosa | C3 |
| coronary artery | GAS6, LAMA2, COL8A1, COL4A1, COL18A1, PDGFC, FGF1, MFGE8, FGF7, C1QA, COL1A2, COL4A2, COL3A1, LAMC1, INHBE, BGN, TFPI, FBLN1, ANGPT1, TGFB3, FBN1, COL5A1, |

TABLE 3-continued

Factors for differentiation/conversion of H9 embryonic stem cells to various target cell types

| Target cell or tissue type | Cell conversion factors |
| --- | --- |
|  | FN1, SEMA3F, BDNF, PDGFA, CYR61, TIMP2, C3, THBS1, EFNA1, INHBA, ICAM4, A2M, NID1, COL1A1, LAMA5 |
| duodenal mucosa | EFNA1, IL16, MDK |
| esophagus muscularis mucosa | LAMA2, PDGFB, COL4A5, COL4A6, COL4A1, FGF7, LAMC1, LAMA4, FN1, THBS1, NID1, COL3A1, FBLN1, COL1A2, SEMA3A, C3, CYR61, WNT5A, COL6A3, ICAM4, TGFB2, TIMP2, PDGFA, BMP4, CLCF1, INHBA, EFNA1, A2M, GDNF, LAMA5 |
| esophagus | EFNA1, VEGFA |
| esophagus squamous epithelium | C3, LAMA2, BMP7, NID1, WNT5A, TFPI, ICAM4, VWF, FGF7, A2M, EFNA1, LAMC1, LAMA4, THBS1, CYR61, COL4A1, SEMA3F, PDGFA, COL6A3, LAMA5, CALR, HMGB1, INHBA |
| gastrocnemius medialis | VWF, VEGFA, TGFB2, WNT5A, CYR61, LAMA2, LAMC1 |
| gastroesophageal sphincter | LAMA2, COL4A5, COL4A6, COL18A1, LAMA4, FGF7, FBN1, NID1, COL4A1, SEMA3A, FN1, TIMP2, FBLN1, COL6A3, THBS1, CYR61, ICAM4, TGFB2, C3, LAMC1, CLCF1, COL3A1, A2M, INHBA, WNT5A, EFNA1, LAMA5, BDNF |
| germinal matrix | NXPH1, NRG1, SLIT1, NRG3, SFRP1, WNT5A, VEGFA, BMP7, INHBB, BDNF |
| kidney | CTGF, GDNF, SLIT2, SEMA3A, FST, COL1A2, COL4A1, VEGFA, BMP4, LAMC1, LAMB1 |
| large intestine | LAMB3, VEGFA |
| layer of hippocampus | BDNF, C3, WNT5A |
| middle frontal area 46 | VEGFA, C3 |
| mucosa of rectum | LTA |
| muscle layer of colon | COL4A1, COL6A3, TNC, NID1, COL5A1, COL3A1, TIMP2, C3, THBS1, ANXA1, LAMA4, FGF7, CYR61, LAMC1, LAMB1, COL1A1, CALR, FGF2 |
| muscle of leg | BMP5, COL1A1, COL1A2, COL3A1, COL4A1, COL4A2, LAMC1 |
| ovary | PDGFD, NDP, WNT5A, FGF7, NTF3, BDNF, COL3A1, NTN3, TGFB2, BMP4, SLIT2, INHBA, FST |
| Peyer's patch | C3, HMGB1 |
| placenta | PGF, EBI3, INHBA, TGFB3, PDGFB, FST |
| rectal smooth muscle tissue | TNC, WNT5A, TGFB3, COL4A1, FGF7, C3 |
| right atrium auricular region | LAMA2, COL1A2, FGF7, THBS1, COL3A1, LAMC1, VEGFA, COL8A1, CYR61, COL4A, COL4A6, COL4A1, BMP4, TGFB3, COL6A3 |
| sigmoid colon | FGF7, COL6A3, SEMA3A |
| spleen | IL16, LTA, TNF, B2M, TGFB1, EFNA1, TNFSF10 |
| stomach | THBS1, COL1A1, LAMC1, TNFSF13, C3 |
| stomach smooth muscle | COL4A1, LAMA4, NID1, COL6A3, COL4A5, COL4A6, COL7A1, COL6A2, FGF7, THBS1, COL18A1, COL5A1, FBLN1, EFNA1, TIMP2, WNT5A, COL1A1, LAMA5, A2M, TGFB2, CALR, INHBA |
| subcutaneous abdominal adipose tissue | ICAM4, C1QA, TIMP2, LAMA4, ADAM9, EFNA1, FGF7, COL4A1, C3, LAMC1, COL4A2, COL3A1 |
| temporal lobe | BDNF, EFNA1, FGF1, FGF9, C3 |
| thoracic aorta | SERPINE1, PDGFC, LTBP1, FN1, GAS6, EDIL3, COL8A1, BGN, ADAM9, ANGPT1, COL4A1, COL3A1, BDNF, COL1A2, TIMP2, COL18A1, LAMC1, TGFB3, CYR61, PDGFA, FBN1, A2M, ICAM4, LAMA5, CALR, C3 |
| thyroid gland | EFNA1, VEGFA, BMP4, PDGFB |
| tibial nerve | COL4A1, COL18A1, TGFB3, EFNA1, C3 |
| vagina | COL1A2, GDF7, COL3A1, FBN1, FGF7, CYR61, COL1A1, TGFB2, EFNA1, TGFB3, BMP4, C3, VEGFA, HMGB1 |

In particular embodiments, one, two, three, four, or five or more of the factors listed in Table 3 are added, or used to contact the source cell in order to convert the source cell to a target cell in vitro. In alternative embodiments, the cells are contacted with an agent for increasing the expression of one or more of the above factors, for example as further described herein. In other embodiments, six, seven, eight, nine, 10, 11, 12, 13, 14, 15 or more, 20 or more, 25 or more, 30 or more or 35 or more of the factors (ligands) listed in Table 3 are added to the source cell or used to contact the source cell, for conversion to the target cell.

The skilled person will be familiar with each of the ligands/factors indicated in the Tables 2 and 3 above. Some particularly preferred examples are provided further below:

As used herein, FN1 refers to the protein Fibronectin, a high-molecular weight (~440 kDa) glycoprotein of the extracellular matrix that binds to membrane-spanning receptor proteins called integrins. FN1 is also known as CIG, ED-B, FINC, FN, FNZ, GFND, GFND2, LETS, MSF, fibronectin 1, SMDCF. An exemplary amino acid sequence of fibronectin is provided in Uniprot accession P02751, and is encoded by the nucleic acid sequence exemplified by accession ENSG00000115414.

As used herein, COL4A1 refers to: Collagen alpha-1(IV) chain (also known as HANAC, ICH, POREN1, arresten, BSVD, RATOR, collagen type IV alpha 1, collagen type IV alpha 1 chain, BSVD1). An exemplary amino acid sequence of COL4A1 is provided in Uniprot accession P02462 and is encoded by the nucleic acid sequence exemplified by accession ENSG00000187498.

As used herein, COL1A2 refers to Collagen alpha-2(1) chain (also known as OI4, collagen type I alpha 2, collagen type I alpha 2 chain, EDSCV, EDSARTH2). An exemplary amino acid sequence of COL1A2 is provided in Uniprot accession P08123 and is encoded by the nucleic acid sequence exemplified by accession ENSG00000164692.

As used herein EDIL3 refers to "EGF like repeats and discoidin domains 3", a protein that in humans is encoded by the EDIL3 gene. The protein encoded by this gene is an integrin ligand. It plays an important role in mediating angiogenesis and may be important in vessel wall remodeling and development. It also influences endothelial cell behavior. An exemplary amino acid sequence of EDIL3 is provided in Uniprot accession O43854 and is encoded by the nucleic acid sequence exemplified by accession ENSG00000164176.

As used herein, ADAM12 refers to Disintegrin and metalloproteinase domain-containing protein 12 (previously Meltrin) an enzyme that in humans is encoded by the ADAM12 gene. ADAM12 has two splice variants: ADAM12-L, the long form, has a transmembrane region and ADAM12-S, a shorter variant, is soluble and lacks the transmembrane and cytoplasmic domains. ADAM12 is also known as ADAM12-OT1, CAR10, MCMP, MCMPMltna, MLTN, MLTNA, ADAM metallopeptidase domain 12. An exemplary amino acid sequence of ADAM12 is provided in Uniprot accession O43184 and is encoded by the nucleic acid sequence exemplified by accession ENSG00000148848.

As used herein WNT5A (also known as hWnt family member 5A) is a protein that in humans is encoded by the WNT5A gene. An exemplary amino acid sequence of Wnt5a is provided in Uniprot accession P41221 and is encoded by the nucleic acid sequence exemplified by accession ENSG00000114251.

As used herein LAMB1 refers to the gene that encodes Laminin subunit beta-1. This protein is also known as CLM, LIS5, and Laminin, beta 1. Laminins, a family of extracellular matrix glycoproteins, are the major noncollagenous constituent of basement membranes. They have been implicated in a wide variety of biological processes including cell adhesion, differentiation, migration, signaling, neurite outgrowth and metastasis. Laminins are composed of 3 non identical chains: laminin alpha, beta and gamma (formerly A, B1, and B2, respectively) and they form a cruciform structure consisting of 3 short arms, each formed by a different chain, and a long arm composed of all 3 chains. An exemplary amino acid sequence of LAMB1 is provided in Uniprot accession P07942 and is encoded by the nucleic acid sequence exemplified by accession ENSG00000091136.

As used herein COL3A1 refers to Type III Collagen, which is a homotrimer, or a protein composed of three identical peptide chains (monomers), each called an alpha 1 chain of type III collagen. Formally, the monomers are called collagen type III, alpha-1 chain and in humans are encoded by the COL3A1 gene. Type III collagen is one of the fibrillar collagens whose proteins have a long, inflexible, triple-helical domain. COL3A1 is also referred to by the identifiers EDS4A, collagen type III alpha 1, collagen type III alpha 1 chain, EDSVASC, and PMGEDSV. An exemplary amino acid sequence of COL3A1 is provided in Uniprot accession P02461 and is encoded by the nucleic acid sequence exemplified by accession ENSG00000168542.

As used herein TFPI refers to tissue factor pathway inhibitor, a single-chain polypeptide which can reversibly inhibit Factor Xa (Xa). While Xa is inhibited, the Xa-TFPI complex can subsequently also inhibit the FVIIa-tissue factor complex. TFPI is also referred to by the identifiers EPI, LACI, TFI, TFPI1. An exemplary amino acid sequence of TFPI is provided in Uniprot accession P10646 and is encoded by the nucleic acid sequence exemplified by accession ENSG00000003436.

As used herein FGF7 (also known as HBGF-7 or KGF) refers to Keratinocyte growth factor, a protein that in humans is encoded by the FGF7 gene. FGF family members possess broad mitogenic and cell survival activities, and are involved in a variety of biological processes, including embryonic development, cell growth, morphogenesis, tissue repair, tumor growth and invasion. This protein is a potent epithelial cell-specific growth factor, whose mitogenic activity is predominantly exhibited in keratinocytes but not in fibroblasts and endothelial cells. An exemplary amino acid sequence of FGF7 is provided in Uniprot accession P21781 and is encoded by the nucleic acid sequence exemplified by accession ENSG00000140285.

As used herein FGF10 refers to Fibroblast Growth Factor 10, a protein that in humans is encoded by the FGF10 gene. FGF family members possess broad mitogenic and cell survival activities, and are involved in a variety of biological processes, including embryonic development, cell growth, morphogenesis, tissue repair, tumor growth and invasion. Fibroblast growth factor 10 is a paracrine signaling molecule seen first in the limb bud and organogenesis development. FGF10 signaling is required for epithelial branching. Therefore, all branching morphogen organs such as the lungs, skin, ear and salivary glands required the constant expression of FGF10. This protein exhibits mitogenic activity for keratinizing epidermal cells, but essentially no activity for fibroblasts, which is similar to the biological activity of FGF7 An exemplary amino acid sequence of FGF10 is provided in Uniprot accession O15520 and is encoded by the nucleic acid sequence exemplified by accession CCDS3950.1.

As used herein APOE refers to Apolipoprotein E (also known as AD2, APO-E, LDLCQS, LPG, ApoE4), a protein involved in the metabolism of fats in the body. An exemplary amino acid sequence of APOE is provided in Uniprot accession P02649 and is encoded by the nucleic acid sequence exemplified by accession ENSG00000130203.

As used herein C3 refers to Complement component 3, a protein which plays a central role in the complement system and contributes to innate immunity. The protein may also be refers to by the identifiers AHUS5, ARMD9, ASP, C3a, C3b, CPAMD1, HEL-S-62p, and complement component 3. An exemplary amino acid sequence of C3 is provided in Uniprot accession P01024 and is encoded by the nucleic acid sequence exemplified by accession ENSG00000125730.

As used herein SERPINE1 refers to Plasminogen activator inhibitor-1 (PAI-1) also known as endothelial plasminogen activator inhibitor or serpin E1, a protein that in humans is encoded by the SERPINE1 gene. PAI-1 is a serine protease inhibitor (serpin) that functions as the principal inhibitor of tissue plasminogen activator (tPA) and urokinase (uPA), the activators of plasminogen and hence fibrinolysis (the physiological breakdown of blood clots). It is a serine protease inhibitor (serpin) protein (SERPINE1). An exemplary amino acid sequence of SERPINE1 is provided in Uniprot accession P05121 and is encoded by the nucleic acid sequence exemplified by accession ENSG00000106366.

As used herein COL6A3 refers to Collagen alpha-3(VI) chain, a protein that in humans is encoded by the COL6A3 gene. This gene encodes the alpha 3 chain, one of the three alpha chains of type VI collagen, a beaded filament collagen found in most connective tissues. The alpha 3 chain of type VI collagen is much larger than the alpha 1 and 2 chains. This difference in size is largely due to an increase in the number of subdomains, similar to von Willebrand Factor type A domains, found in the amino terminal globular domain of all the alpha chains. In addition to the full length transcript, four transcript variants have been identified that encode proteins with N-terminal globular domains of varying size. An exemplary amino acid sequence of COL6A3 is provided in Uniprot accession P12111 and is encoded by the nucleic acid sequence exemplified by accession ENSG00000163359.

As used herein CXCL12 refers to the stromal cell-derived factor 1 (SDF1), also known as C-X-C motif chemokine 12, IRH, PBSF, SCYB12, SDF1, TLSF, TPAR1, and C-X-C motif chemokine ligand 12. The gene encoding CXCL12 produces 7 isoforms through alternative splicing. An exemplary amino acid sequence of CXCL12 is provided in Uniprot accession P48061 and is encoded by the nucleic acid sequence exemplified by accession ENSG00000107562.

As used herein TGFB2 and TGFB3 refer respectively to transforming growth factor beta 2 and transforming growth factor beta 3. Both proteins are cytokines involved in cell differentiation, embryogenesis and development. An exemplary accession number for TGFB2 is P61812. An exemplary accession number for TGFB3 is P10600.

As used herein GDF5 refers to growth/differentiation factor 5, and is encoded by the GDF5 gene. The protein encoded by this gene is closely related to the bone morphogenetic protein (BMP) family and is a member of the TGF-beta superfamily. An exemplary accession number for GDF5 is P43026.

As used herein NID1 refers to Nidogen-1 (NID-1), formerly known as entactin, is a protein that in humans is encoded by the NID1 gene. Both nidogen-1 and nidogen-2 are essential components of the basement membrane alongside other components such as type IV collagen, proteoglycans (heparan sulfate and glycosaminoglycans), laminin and fibronectin. An exemplary accession number for NID 1 is P14543.

As used herein THBS1 refers to Thrombospondin 1, abbreviated as THBS1, is a protein that in humans is encoded by the THBS1 gene. Thrombospondin 1 is a subunit of a disulfide-linked homotrimeric protein. This protein is an adhesive glycoprotein that mediates cell-to-cell and cell-to-matrix interactions. This protein can bind to fibrinogen, fibronectin, laminin, collagens types V and VII and integrins alpha-V/beta-1. An exemplary accession number for THBS1 is P07996.

As used herein BMP4 and BMP6 refer respectively to Bone morphogenetic protein 4 and Bone morphogenetic protein 6. The proteins encoded by these genes are members of the TGFβ superfamily. Bone morphogenetic proteins are known for their ability to induce the growth of bone and cartilage. BMP4 is highly conserved evolutionarily. BMP4 is found in early embryonic development in the ventral marginal zone and in the eye, heart blood and otic vesicle. BMP6 is able to induce all osteogenic markers in mesenchymal stem cells. An exemplary accession number for BMP6 is P12644. An exemplary accession number for BMP6 is P22004.

As used herein CTGF refers to also known as CCN2 or connective tissue growth factor, is a matricellular protein of the CCN family of extracellular matrix-associated heparin-binding proteins (see also CCN intercellular signaling protein). CTGF has important roles in many biological processes, including cell adhesion, migration, proliferation, angiogenesis, skeletal development, and tissue wound repair, and is critically involved in fibrotic disease and several forms of cancers. An exemplary accession number for CTGF is P29279.

As used herein PDGFB refers to Platelet-derived growth factor subunit B is a protein that in humans is encoded by the PDGFB gene. The protein encoded by this gene is a member of the platelet-derived growth factor family. The four members of this family are mitogenic factors for cells of mesenchymal origin and are characterized by a motif of eight cysteines. This gene product can exist either as a homodimer (PDGF-BB) or as a heterodimer with the platelet-derived growth factor alpha (PDGFA) polypeptide (PDGF-AB), where the dimers are connected by disulfide bonds. An exemplary accession number for PDGFB is P01127.

It will be understood that in preferred examples, the relevant factors (ligands) for maintaining the cells of interest may be provided to the cells directly in order for the cells to be "contacted" with the relevant factors. Moreover, as used herein, the terms "contact", "contacted", "contacting", "treat", "treating", or "introducing" may be used interchangeably to mean subjecting a cell to any kind of process or condition such as transfection of exogenous DNA or introducing agents to the cells.

For example, the culture media can be directly supplemented with the relevant factors. In alternative embodiments, the cells may be transfected with a nucleic acid molecule encoding the relevant factor (or a vector encoding one or more of the relevant factors), such that the factor is then expressed by the cell.

Furthermore, the cells may be treated in such a way so as to increase the amount of the relevant factors in the cell. Again, this can be through direct supplementation of the cell culture media, or by recombinant methods for either increasing expression of an endogenous gene in the cell, or by providing an exogenous source of nucleic acid encoding the relevant factor, expressing the nucleic acid and thereby increasing the amount of the factor in the cell.

Similarly, for methods of converting a cell (including for transdifferentiation and directed differentiation methods), the factors for conversion may be provided directly in culture, or alternatively, expressed in the source cell to promote conversion to the target cell.

It will be understood that factors that are proteins (including transcription factors and other regulatory factors) may be provided to the cells in accordance with the methods described herein. Alternatively a variant of the factor(s) may be provided so as to achieve the same outcome.

The term a "variant" in referring to a polypeptide that is at least 70%, 80%, 85%, 90%, 95%, 98%, or 99% identical to the full length polypeptide. The present invention contemplates the use of variants of the factors described herein. The variant could be a fragment of full-length polypeptide or a naturally occurring splice variant. The variant could be a polypeptide at least 70%, 80%, 85%, 90%, 95%, 98%, or 99% identical to a fragment of the polypeptide, wherein the fragment is at least 50%, 60%, 70%, 80%, 85%, 90%, 95%, 98%, or 99% as long the full length wild type polypeptide or a domain thereof has a functional activity of interest such as the ability to promote conversion of a source cell type to a target cell type. In some embodiments the domain is at least 100, 200, 300, or 400 amino acids in length, beginning at any amino acid position in the sequence and extending toward the C-terminus. Variations known in the art to eliminate or substantially reduce the activity of the protein are preferably avoided. In some embodiments, the variant lacks an N- and/or C-terminal portion of the full length polypeptide, e.g., up to 10, 20, or 50 amino acids from either terminus is lacking. In some embodiments the polypeptide has the sequence of a mature (full-length) polypeptide, by which is meant a polypeptide that has had one or more portions such as a signal peptide removed during normal intracellular proteolytic processing (e.g., during co-translational or post-translational processing). In some embodiments wherein the protein is produced other than by purifying it from cells that naturally express it, the protein is a chimeric polypeptide, by which is meant that it contains portions from two or more different species. In some embodiments wherein a protein is produced other than by purifying it from cells that naturally express it, the protein is a derivative, by which is meant that the protein comprises additional sequences not related to the protein so long as those sequences do not substantially reduce the biological activity of the protein. One of skill in the art will be aware of, or will readily be able to ascertain, whether a particular polypeptide variant, fragment, or derivative is functional using assays known in the art. For example, the ability of a variant of a transcription factor to convert a source cell to a target cell type can be assessed using the assays as disclose herein in the Examples. Other convenient assays include measuring the ability to activate transcription of a reporter construct containing a transcription factor binding site operably linked to a nucleic acid sequence encoding a detectable marker such as luciferase. In certain embodiments of the invention a functional variant or fragment has at least 50%, 60%, 70%, 80%, 90%, 95% or more of the activity of the full length wild type polypeptide.

The term "increasing the amount of" with respect to increasing an amount of a factor, refers to increasing the quantity of the factor in a cell of interest (e.g., such as an astrocyte, cardiomyocyte smooth muscle cell, endothelial cell or a source cell for conversion to a target cell). In some embodiments, the amount of factor is "increased" in a cell of interest (e.g., a cell into which an expression cassette directing expression of a polynucleotide encoding one or more transcription factors has been introduced) when the quantity of factor is at least 10%, 20%, 30%, 40%, 50%, 60%, 70%, 80%, 90%, or more relative to a control (e.g., a cell into which none of said expression cassettes have been introduced). However, any method of increasing an amount of a transcription factor is contemplated including any method that increases the amount, rate or efficiency of transcription, translation, stability or activity of a transcription factor (or the pre-mRNA or mRNA encoding it). In addition, down-regulation or interference of a negative regulator of transcription expression, increasing efficiency of existing transcription (e.g. SINEUP) are also considered.

The term "exogenous," when used in relation to a protein, gene, nucleic acid, or polynucleotide in a cell or organism refers to a protein, gene, nucleic acid, or polynucleotide that has been introduced into the cell or organism by artificial or natural means; or in relation to a cell, refers to a cell that was isolated and subsequently introduced to other cells or to an organism by artificial or natural means. An exogenous nucleic acid may be from a different organism or cell, or it may be one or more additional copies of a nucleic acid that occurs naturally within the organism or cell. An exogenous cell may be from a different organism, or it may be from the same organism. By way of a non-limiting example, an exogenous nucleic acid is one that is in a chromosomal location different from that of natural cells, or is otherwise flanked by a different nucleic acid sequence than that found in nature. An exogenous nucleic acid may also be extra-chromosomal, such as an episomal vector.

The method of the disclosure may be "miniaturized" in an assay system through any acceptable method of miniaturization, including but not limited to multi-well plates, such as 24, 48, 96 or 384-wells per plate, microchips or slides. The assay may be reduced in size to be conducted on a micro-chip support, advantageously involving smaller amounts of reagent and other materials. Any miniaturization of the process which is conducive to high-throughput screening is within the scope of the invention.

In any method of the invention the target cells can be transferred into the same mammal from which the source cells were obtained. In other words, the source cells used in a method of the invention can be an autologous cell, i.e., can be obtained from the same individual in which the target cells are to be administered. Alternatively, the target cell can be allogenically transferred into another individual. Preferably, the cell is autologous to the subject in a method of treating or preventing a medical condition in the individual.

The term "cell culture medium" (also referred to herein as a "culture medium" or "medium") as referred to herein is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art. Exemplary cell culture medium for use in methods of the invention are shown in Table 4.

The term "expression" refers to the cellular processes involved in producing RNA and proteins and as appropriate, secreting proteins, including where applicable, but not limited to, for example, transcription, translation, folding, modification and processing.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated".

The term "vector" refers to a carrier DNA molecule into which a DNA sequence can be inserted for introduction into a host or source cell. Preferred vectors are those capable of autonomous replication and/or expression of nucleic acids to which they are linked. Vectors capable of directing the expression of genes to which they are operatively linked are referred to herein as "expression vectors". Thus, an "expression vector" is a specialized vector that contains the necessary regulatory regions needed for expression of a gene of interest in a host cell. In some embodiments the gene of interest is operably linked to another sequence in the vector. Vectors can be viral vectors or non-viral vectors. Should viral vectors be used, it is preferred the viral vectors are replication defective, which can be achieved for example by removing all viral nucleic acids that encode for replication. A replication defective viral vector will still retain its infective properties and enters the cells in a similar manner as a replicating adenoviral vector, however once admitted to the cell a replication defective viral vector does not reproduce or multiply. Vectors also encompass liposomes and nanoparticles and other means to deliver DNA molecule to a cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. The term "operatively linked" includes having an appropriate start signal (e.g. ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

The term "viral vectors" refers to the use of viruses, or virus-associated vectors as carriers of a nucleic acid construct into a cell. Constructs may be integrated and packaged into non-replicating, defective viral genomes like Adenovirus, Adeno-associated virus (AAV), or Herpes simplex virus (HSV) or others, including retroviral and lentiviral vectors, for infection or transduction into cells. The vector may or may not be incorporated into the cell's genome. The constructs may include viral sequences for transfection, if desired. Alternatively, the construct may be incorporated into vectors capable of episomal replication, e.g EPV and EBV vectors.

As used herein, the term "adenovirus" refers to a virus of the family Adenovirida. Adenoviruses are medium-sized (90-100 nm), nonenveloped (naked) icosahedral viruses composed of a nucleocapsid and a double-stranded linear DNA genome.

As used herein, the term "non-integrating viral vector" refers to a viral vector that does not integrate into the host genome; the expression of the gene delivered by the viral vector is temporary. Since there is little to no integration into the host genome, non-integrating viral vectors have the advantage of not producing DNA mutations by inserting at a random point in the genome. For example, a non-integrating viral vector remains extra-chromosomal and does not insert its genes into the host genome, potentially disrupting the expression of endogenous genes. Non-integrating viral vectors can include, but are not limited to, the following: adenovirus, alphavirus, picornavirus, and vaccinia virus. These viral vectors are "non-integrating" viral vectors as the term is used herein, despite the possibility that any of them may, in some rare circumstances, integrate viral nucleic acid into a host cell's genome. What is critical is that the viral vectors used in the methods described herein do not, as a rule or as a primary part of their life cycle under the conditions employed, integrate their nucleic acid into a host cell's genome.

The vectors described herein can be constructed and engineered using methods generally known in the scientific literature to increase their safety for use in therapy, to include selection and enrichment markers, if desired, and to optimize expression of nucleotide sequences contained thereon. The vectors should include structural components that permit the vector to self-replicate in the source cell type. For example, the known Epstein Barr oriP/Nuclear Antigen-1 (EBNA-I) combination (see, e.g., Lindner, S. E. and B. Sugden, The plasmid replicon of Epstein-Barr virus: mechanistic insights into efficient, licensed, extrachromosomal replication in human cells, Plasmid 58:1 (2007), incorporated by reference as if set forth herein in its entirety) is sufficient to support vector self-replication and other combinations known to function in mammalian, particularly primate, cells can also be employed. Standard techniques for the construction of expression vectors suitable for use in the present invention are well-known to one of ordinary skill in the art and can be found in publications such as Sambrook J, et al., "Molecular cloning: a laboratory manual," (3rd ed. Cold Spring harbor Press, Cold Spring Harbor, N.Y. 2001), incorporated herein by reference as if set forth in its entirety.

In the methods of the invention, genetic material encoding the relevant factors required for a conversion is delivered into the source cells via one or more cell conversion vectors. Each factor can be introduced into the source cells as a polynucleotide transgene that encodes the factor operably linked to a heterologous promoter that can drive expression of the polynucleotide in the source cell.

Suitable cell conversion vectors are any described herein, including episomal vectors, such as plasmids, that do not encode all or part of a viral genome sufficient to give rise to an infectious or replication-competent virus, although the vectors can contain structural elements obtained from one or more virus. One or a plurality of cell conversion vectors can be introduced into a single source cell. One or more transgenes can be provided on a single cell conversion vector. One strong, constitutive transcriptional promoter can provide transcriptional control for a plurality of transgenes, which can be provided as an expression cassette. Separate expression cassettes on a vector can be under the transcriptional control of separate strong, constitutive promoters, which can be copies of the same promoter or can be distinct promoters. Various heterologous promoters are known in the art and can be used depending on factors such as the desired expression level of the transcription factor. It can be advantageous, as exemplified below, to control transcription of separate expression cassettes using distinct promoters having distinct strengths in the source cells. Another consideration in selection of the transcriptional promoters is the rate at which the promoter(s) is silenced. The skilled artisan will appreciate that it can be advantageous to reduce expression of one or more transgenes or transgene expression cassettes after the product of the gene(s) has completed or substantially completed its role in the cell conversion method. Exemplary promoters are the human EF1α elongation factor promoter, CMV cytomegalovirus immediate early promoter and CAG chicken albumin promoter, and corresponding homologous promoters from other species. In human somatic cells, both EF1α and CMV are strong promoters, but the CMV promoter is silenced more efficiently than the EF1α promoter such that expression of transgenes under control of the former is turned off sooner than that of transgenes under control of the latter. The transcription factors can be expressed in the source cells in a relative ratio that can be varied to modulate cell conversion efficiency. Preferably, where a plurality of transgenes is encoded on a single transcript, an internal ribosome entry site is provided upstream of transgene(s) distal from the transcriptional promoter. Although the relative ratio of factors can vary depending upon the factors delivered, one of ordinary skill in possession of this disclosure can determine an optimal ratio of factors.

The skilled artisan will appreciate the advantageous efficiency of introducing all factors via a single vector rather than via a plurality of vectors. Thus, the present invention contemplates the use of a single vector (or a reduced number of vectors) wherein the single or reduced number of vectors encode a plurality of factors required for conversion, or cell maintenance, as the case may be.

After introduction of the conversion vector(s) and while the source cells are being converted, the vectors can persist in target cells while the introduced transgenes are transcribed and translated. Transgene expression can be advantageously downregulated or turned off in cells that have been converted to a target cell type. The cell conversion vector(s) can remain extra-chromosomal. At extremely low efficiency, the vector(s) can integrate into the cells' genome. The examples that follow are intended to illustrate but in no way limit the present invention.

Suitable methods for nucleic acid delivery for transformation of a cell, a tissue or an organism for use with the current invention are believed to include virtually any method by which a nucleic acid (e.g., DNA) can be introduced into a cell, a tissue or an organism, as described herein or as would be known to one of ordinary skill in the art (e.g., Stadtfeld and Hochedlinger, Nature Methods 6(5):329-330 (2009); Yusa et al., Nat. Methods 6:363-369 (2009); Woltjen, et al., Nature 458, 766-770 (9 Apr. 2009)). Such methods include, but are not limited to, direct delivery of DNA such as by ex vivo transfection (Wilson et al., Science, 244:1344-1346, 1989, Nabel and Baltimore, Nature 326: 711-713, 1987), optionally with a lipid-based transfection reagent such as Fugene6 (Roche) or Lipofectamine (Invitrogen), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, J. Cell Biol., 101:1094-1099, 1985; U.S. Pat. No. 5,789,215, incorporated herein by reference); by electroporation (U.S. Pat. No. 5,384,253, incorporated herein by reference; Tur-Kaspa et al., Mol. Cell Biol., 6:716-718, 1986; Potter et al., Proc. Nat'l Acad. Sci. USA, 81:7161-7165, 1984); by calcium phosphate precipitation (Graham and Van Der Eb, Virology, 52:456-467, 1973; Chen and Okayama, Mol. Cell Biol., 7(8):2745-2752, 1987; Rippe et al., Mol. Cell Biol., 10:689-695, 1990); by using DEAE-dextran followed by polyethylene glycol (Gopal, Mol. Cell Biol., 5:1188-1190, 1985); by direct sonic loading (Fechheimer et al., Proc. Nat'l Acad. Sci. USA, 84:8463-8467, 1987); by liposome mediated transfection (Nicolau and Sene, Biochim. Biophys. Acta, 721:185-190, 1982; Fraley et al., Proc. Nat'l Acad. Sci. USA, 76:3348-3352, 1979; Nicolau et al., Methods Enzymol., 149:157-176, 1987; Wong et al., Gene, 10:87-94, 1980; Kaneda et al., Science, 243:375-378, 1989; Kato et al., J Biol. Chem., 266:3361-3364, 1991) and receptor-mediated transfection (Wu and Wu, Biochemistry, 27:887-892, 1988; Wu and Wu, J. Biol. Chem., 262:4429-4432, 1987); and any combination of such methods, each of which is incorporated herein by reference.

A number of polypeptides capable of mediating introduction of associated molecules into a cell have been described previously and can be adapted to the present invention. See, e.g., Langel (2002) Cell Penetrating Peptides: Processes and Applications, CRC Press, Pharmacology and Toxicology Series. Examples of polypeptide sequences that enhance transport across membranes include, but are not limited to, the Drosophila homeoprotein antennapedia transcription protein (AntHD) (Joliot et al., New Biol. 3: 1121-34, 1991; Joliot et al., Proc. Natl. Acad. Sci. USA, 88: 1864-8, 1991; Le Roux et al., Proc. Natl. Acad. Sci. USA, 90: 9120-4, 1993), the herpes simplex virus structural protein VP22 (Elliott and O'Hare, Cell 88: 223-33, 1997); the HIV-1 transcriptional activator TAT protein (Green and Loewenstein, Cell 55: 1179-1188, 1988; Frankel and Pabo, Cell 55: 1 289-1193, 1988); Kaposi FGF signal sequence (kFGF); protein transduction domain-4 (PTD4); Penetratin, M918, Transportan-10; a nuclear localization sequence, a PEP-I peptide; an amphipathic peptide (e.g., an MPG peptide); delivery enhancing transporters such as described in U.S. Pat. No. 6,730,293 (including but not limited to an peptide sequence comprising at least 5-25 or more contiguous arginines or 5-25 or more arginines in a contiguous set of 30, 40, or 50 amino acids; including but not limited to an peptide having sufficient, e.g., at least 5, guanidino or amidino moieties); and commercially available Penetratin™ 1 peptide, and the Diatos Peptide Vectors ("DPVs") of the Vectocell® platform available from Daitos S.A. of Paris, France. See also, WO/2005/084158 and WO/2007/123667 and additional transporters described therein. Not only can these proteins pass through the plasma membrane but the attachment of other proteins, such as the transcription factors described herein, is sufficient to stimulate the cellular uptake of these complexes

TABLE 4

| Cell culture media that can be used to culture various cell types. | | | |
| --- | --- | --- | --- |
| Cell | Media | Cat#: | Company |
| Astrocytes | Astrocyte Medium | A1261301 | Life Technologies |
| Dermal fibroblasts | Medium 106 | M-106-500 | ThermoFisher |
| Endothelial cells | Medium 131, Endothelial Cell Growth Medium MV 2 | M131500, C-22022 | PromoCell |
| Epidermal Keratinocytes | EpiLife | M-EPICF-500 | ThermoFisher |
| H9 ESC line | KSR | 10828-028 | ThermoFisher |
| | Essential 8 | A1517001 | Life Technologies |
| | mTeSR1 | | Stemcell technologies |
| Monocytes | Macrophage-SFM | 12065-074 | ThermoFisher |
| Chondrocytes | Eagle's Minimum Essential Medium | 10-009-CV | Corning |
| Hair Follicles | Medium 199/Ham's F12 | 11150-059/ 11765-047 | ThermoFisher |
| CD4+ T-cell | CTS ™ OpTmizer ™ T Cell Expansion SFM | A10485-01 | ThermoFisher |
| CD8+ T-cell | CTS ™ OpTmizer ™ T Cell Expansion SFM | A10485-01 | ThermoFisher |
| NK-cell | alpha MEM | M 8042 | Sigma Aldrich |
| PSCs | Essential 8 Medium | A1517001 | Life Technologies |

TABLE 4-continued

Cell culture media that can be used to culture various cell types.

| Cell | Media | Cat#: | Company |
|------|-------|-------|---------|
| HSCs | StemPro ® CD34+ Cell Kit | A14059 | ThermoFisher |
| MSCs of adipose | StemPro ® Human Adipose-Derived Stem Cell Kit | R7788-110 | ThermoFisher |
| MSCs of bone marrow | StemPro ® BM Mesenchymal Stem Cells kit Alpha-MEM with 15% FBS, glutamine, penicillin ands treptomycin | A15652 | ThermoFisher Life Technologies |
| Oligodendrocytes precursors | Neurobasal medium | 21103-049 | ThermoFisher |
| Skeletal muscle cells | DMEM | 11965-092 | ThermoFisher |
| Smooth muscle cells | Medium 231 | M-231-500 | ThermoFisher, Life Technologies |
| Cardiomyocytes | Myocyte growth medium | C-22011 | PromoCell |

For differentiation methods, the above, relevant cell type media may be used to facilitate differentiation. For cell maintenance, it is possible to culture the cells using only the factors identified herein for cell maintenance. For example:

Normal human astrocytes (NHA) (Lonza Bioscience) are thawed and maintained in Matrigel for 1 passage. (Matrigel is the trade name for a gelatinous protein mixture secreted by Engelbreth-Holm-Swarm (EHS) mouse sarcoma cells produced and marketed by Corning Life Sciences and BD Biosciences. Trevigen, Inc. markets their own version under the trade name Cultrex BME. Matrigel resembles the complex extracellular environment found in many tissues and is used by cell biologists as a substrate (basement membrane matrix) for culturing cells). Cells are subsequently passaged using Accutase and seeded onto respective conditions: no substrate, Matrigel, FN1 (Fibronectin), COL4A1 (Collagen 4), LAMB1 (LN221), ADAM12, COL1A2 (Collagen I), EDIL3 and all factors (combination of aforementioned substrates and growth factors without Matrigel).

Primary human cardiomyocyte cell culture thawing and maintenance media can be purchased from PromoCell (Heidelberg, Germany). Cells are cultured in myocyte growth medium (PromoCell, C-22011) supplemented with 2% fetal calf serum, EGF (5 ng/ml), FGF2 (2 ng/ml), EGF (0.5 ng/ml) and insulin (0.5 µg/ml). Cells are subsequently passaged using 0.04% Trypsin/0.03% EDTA (Promocell) and seeded onto respective conditions: no substrate, Geltrex (Life technologies), FN1 (Fibronectin) (Sigma Aldrich), COL1A2 (Collagen I) (Sigma Aldrich), TFPI (Tissue factor pathway inhibitor) (Prospec-Tany TechnoGene Ltd), ApoE (Apolipoprotein E) (Novus Biologicals), FGF7 (Fibroblast Growth Factor-7) (Stemcell Technologies) and all ligands (combination of aforementioned substrates and ligands without Geltrex). ReN VM Cells (Millipore) were maintained in DMEM/F12 (Gibco) with B27 supplement (Gibco), 1% Heparin (Stem Cell Technologies), 1% penicillin and streptomycin (Gibco), 20 ng/ml EGF (Peprotech) and 20 ng/ml FGF2 (Miltenyi Biotec). Cells were passaged using Accutase (Stem Cell Technologies) and seeded onto flasks coated with Matrigel (Corning). For the differentiation into astrocytes, cultures are transitioned into Astrocyte Medium (DMEM High Glucosse, N2, 10% FBS; Gibco) for 2 weeks. Cells are isolated using surface markers CD44 (103028, Biolegend) and reseeded onto respective conditions: no substrate, Matrigel, FN1 (Fibronectin) (Sigma Aldrich), COL4A1 (Collagen IV) (Sigma Aldrich), LAMB1 (Laminin221) (Biolamina), ADAM12 (Sigma Aldrich), COL1A2 (Collagen I) (Sigma Aldrich), EDIL3 (R&D Systems) and all ligands (combination of aforementioned substrates and secreted ligands without Matrigel). Cells are analyzed at passage 2 (3 and 6 days into passage).

Primary pulmonary artery smooth muscle cells (HPASMC) and human aortic endothelial cells (HA-oEC) culture thawing and maintenance media can be purchased from Gibco (C0095C, Life technologies, USA) and PromoCell (C-12271, Heidelberg, Germany) respectively. The smooth muscle cells are cultured in Medium 231 (Life Technologies, USA) supplemented with fetal bovine serum: 4.9% v/v, human basic fibroblast growth factor (2 ng/ml), human epidermal growth factor (0.5 ng/ml), heparin (5 ng/ml), recombinant human insulin-like growth factor-I (0.01 µg/ml) and BSA (0.2 µg/ml). Cells are subsequently passaged using TrypLE Express (Life Technologies) and seeded onto respective conditions: no substrate, Geltrex (Life Technologies), NID1 (Nidogen-1) (Merck), COL1A1 (Collagen I) (Southern Biotech), COL4A1 (Collagen 4) (Merck), COL6A1 (Collagen 6) (Rockland), THBS1 (Thrombospondin 1) (Merck), FGF10 (Fibroblast Growth Factor-10) (Stemcell Technologies), FGF7 (Fibroblast Growth Factor-7) (Stemcell Technologies) and all ligands (a combination of aforementioned substrates and ligands without Geltrex).

Endothelial cells are cultured in Endothelial Cell Growth Medium MV 2 (PromoCell, C-22022) supplemented with supplement mix containing fetal calf serum (0.05 ml/ml), epidermal growth factor (recombinant human) (5 ng/ml), basic fibroblast growth factor (recombinant human) (10 ng/ml), insulin-like growth factor (Long R3 IGF) (20 ng/ml), vascular endothelial growth factor (recombinant human) (0.5 ng/ml), ascorbic acid (1 µg/ml) and hydrocortisone (0.2 µg/ml). Cells are subsequently passaged using TrypLE Express (Life Technologies) and seeded onto respective conditions: no substrate, Geltrex (Life Technologies), FN1 (Fibronectin) (Merck), THBS1 (Thrombospondin 1) (Merck), CTGF (Connective tissue growth factor) (Life Technologies), PDGFB (Platelet-Derived Growth Factor Subunit B) (Stemcell Technologies), CYR61 (Cysteine-rich angiogenic inducer 61) (Novus), BMP4 (Bone Morphogenetic Protein 4) (Life Technologies), BMP6 (Bone Morphogenetic Protein 6) (Merck) and all ligands (a combination of aforementioned substrates and ligands without Geltrex).

H9 embryonic stem cells are maintained in flasks coated with vitronectin (Gibco) and cultured in Essential 8 medium (Gibco).

For astrocyte differentiation, from H9 stem cells via neural progenitor cells, cells are seeded onto flasks coated with Matrigel at a density of $5 \times 10^4$ cells/cm$^2$ in neural induction medium containing DMEM/F12, B27 without vitamin A supplement (Gibco), N2 supplement (Gibco), 0.1% 2-mercaptoethanol (Gibco), 0.66% Bovine Serum Albumin (Gibco), 1% Sodium Pyruvate (Gibco), 1% Non-essential Amino Acids (Gibco), 1% Penicillin and Streptomycin, 100 ng/ml LDN193189 (Tocris Bioscience) for 14 days. Cells are subsequently sorted for NCAM+ cells (with anti-pSA-NCAM antibody, 130-115-809, Miltenyi Biotec) and re-expanded onto Matrigel-coated flasks for another 7 days. After a week of expansion, cells are passaged and reseeded onto respective conditions in Astrocyte Medium (Gibco): Matrigel, FN1 (Fibronectin) (Sigma Aldrich), COL4A1 (Collagen 4) (Sigma Aldrich), LAMB1 (LN221) (Biolamina), Matrigel+ADAM12 (Sigma Aldrich), COL1A2 (Collagen I) (Sigma Aldrich), Matrigel+EDIL3 (R&D Systems) and all factors (combination of aforementioned substrates and growth factors without Matrigel). Cells are then analyzed at day 14 and day 21.

For cardiac differentiation, cells are seeded at day −3 at a density of $5 \times 10^4$ cells/cm$_2$ in Essential 8 medium (Gibco) onto Matrigel- or COL1A2-coated plates depending on condition. At day 0, medium is replaced with RPMI1640 (Gibco) supplemented with B27 supplement without insulin (Gibco), 1% penicillin and streptomycin (Gibco), 213 g/ml Ascorbic Acid (Sigma-Aldrich), 0.66% Bovine Serum Albumin (Gibco) for 5 days with daily medium change. On days 0-2, culture is also supplemented with 3 μM CHIR. On day 3, CHIR is withdrawn. On days 4 and 5, cultures are supplemented with 5 μM IWR. After day 5, the culture medium is subsequently changed to RPMI1640 (Gibco) supplemented with B27 supplement (Gibco), 1% penicillin and streptomycin (Gibco), 213 g/ml Ascorbic Acid (Sigma-Aldrich), 0.66% Bovine Serum Albumin (Gibco) with daily medium change every 2 days. During differentiation, cells are subjected to their respective conditions with differentiation medium: Matrigel (control), FGF7 (Peprotech, 10 ng/ml) (Miyashita et al., 2013), TGFB3 (Stemcell Technologies, 10 ng/ml) (Dahlin et al., 2014), TGFB2 (Stemcell Technologies, 10 ng/ml) GDFS (Stemcell Technologies, 50 ng/ml) COL1A2 (Collagen I) (Sigma Aldrich) and all ligands (combination of aforementioned substrates and secreted ligands with COL1A2-coated plates). Substrates and ligands are applied based on manufacturer's recommendation unless otherwise referenced.

Computer Implemented Methods

Embodiments of the methods described herein can be implemented in a computer processing system. Accordingly in a further aspect, the present invention provides a computer processing system adapted to perform an embodiment of any one of the methods disclosed herein.

Figure 10:
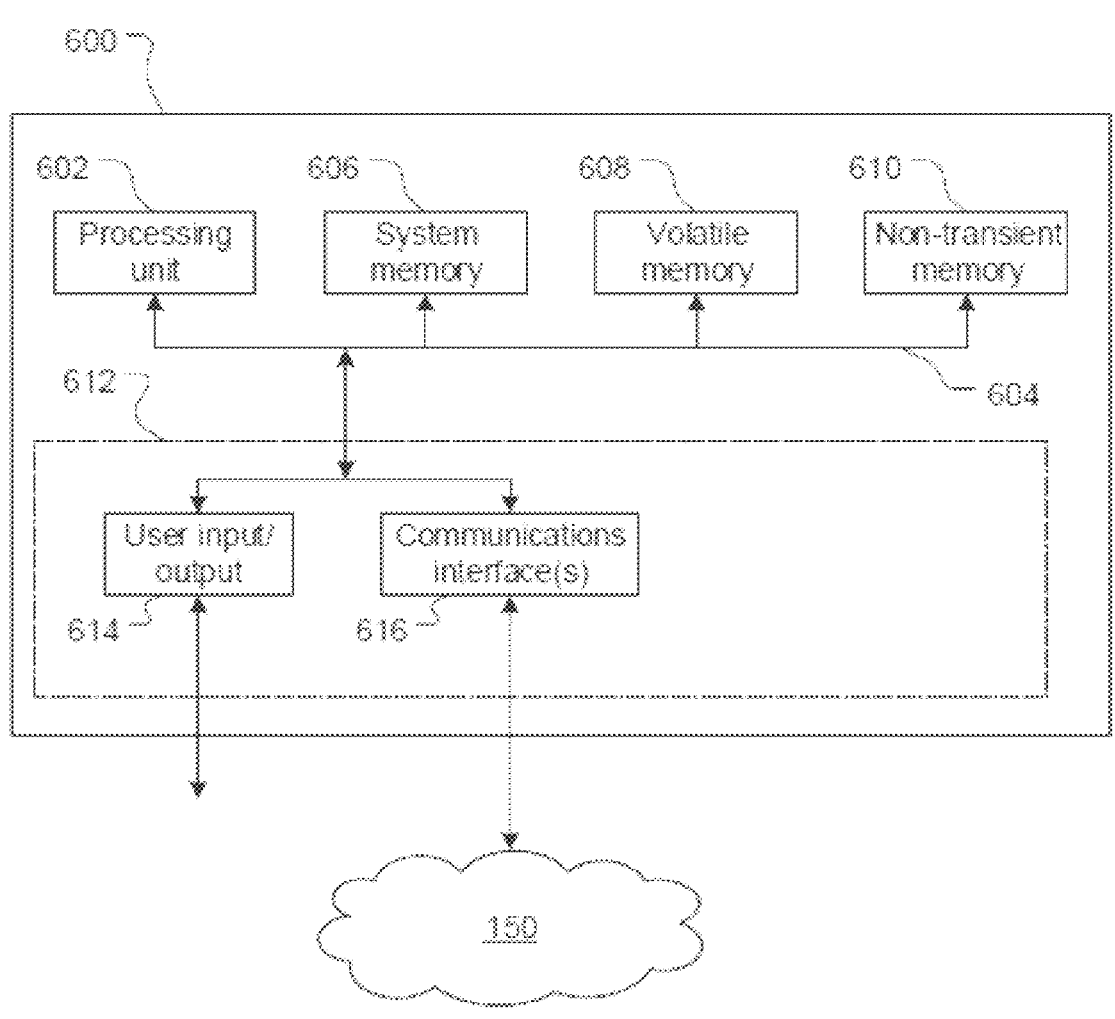
FIG. 10: Block diagram one type of computer processing system 600 for implementing embodiments and/or features of the methods described herein.

FIG. 10 provides a block diagram of one type of computer processing system 600 for implementing embodiments and/or features of the methods described herein. System 600 is a general purpose computer processing system. It will be appreciated that FIG. 10 does not illustrate all functional or physical components of a computer processing system. For example, no power supply or power supply interface has been depicted. However, system 600 will either carry a power supply or be configured for connection to a power supply (or both). It will also be appreciated that the particular type of computer processing system will determine the appropriate hardware and architecture, and alternative computer processing systems suitable for implementing aspects of the invention may have additional, alternative, or fewer components than those depicted.

The computer processing system 600 includes at least one processing unit 602. The processing unit 602 may be a single computer processing device (e.g. a central processing unit, graphics processing unit, or other computational device), or may include a plurality of computer processing devices. In some instances all processing will be performed by processing unit 602; however, in other instances processing may also be performed by remote processing devices accessible and useable (either in a shared or dedicated manner) by the system 600.

Through a communications bus 604 the processing unit 602 is in data communication with a one or more machine readable storage (memory) devices which store instructions and/or data for controlling operation of the processing system 600. In this instance system 600 includes a system memory 606 (e.g. a BIOS), volatile memory 608 (e.g. random access memory such as one or more DRAM modules), and non-volatile memory 610 (e.g. one or more hard disk or solid state drives). In some embodiments any one or more of the data sources used in a method described herein can be stored in the non-volatile memory (e.g. a database storing ChIP-seq information, protein-protein interaction network data, gene sequence database).

System 600 also includes one or more interfaces, indicated generally by 612, via which system 600 interfaces with various devices and/or networks. Generally speaking, other devices may be integral with system 600, or may be separate. Where a device is separate from system 600, connection between the device and system 600 may be via wired or wireless hardware and communication protocols, and may be a direct or an indirect (e.g. networked) connection.

Wired connection with other devices/networks may be by any appropriate standard or proprietary hardware and connectivity protocols. For example, system 600 may be configured for wired connection with other devices/communications networks by one or more of: USB; FireWire; eSATA; Thunderbolt; Ethernet; OS/2; Parallel; Serial; HDMI; DVI; VGA; SCSI; AudioPort. Other wired connections are, of course, possible.

Wireless connection with other devices/networks may similarly be by any appropriate standard or proprietary hardware and communications protocols. For example, system 600 may be configured for wireless connection with other devices/communications networks using one or more of: infrared; BlueTooth; WiFi; near field communications (NFC); Global System for Mobile Communications (GSM), Enhanced Data GSM Environment (EDGE), long term evolution (LTE), wideband code division multiple access (W-CDMA), code division multiple access (CDMA). Other wireless connections are, of course, possible.

Generally speaking, the devices to which system 600 connects—whether by wired or wireless means—include one or more input devices to allow data to be input into/ received by system 600 for processing by the processing unit 602, and one or more output device to allow data to be output by system 600. Example devices are described below, however it will be appreciated that not all computer processing systems will include all mentioned devices, and that additional and alternative devices to those mentioned may well be used.

For example, system 600 may include or connect to one or more input devices by which information/data is input into (received by) system 600. Such input devices may include keyboards, mice, trackpads, microphones, accelerometers, proximity sensors, GPS devices and the like. System 600 may also include or connect to one or more output devices controlled by system 600 to output information. Such output devices may include devices such as a CRT displays, LCD displays, LED displays, plasma displays, touch screen displays, speakers, vibration modules, LEDs/ other lights, and such like. System 600 may also include or connect to devices which may act as both input and output devices, for example memory devices (hard drives, solid state drives, disk drives, compact flash cards, SD cards and the like) which system 600 can read data from and/or write data to, and touch screen displays which can both display (output) data and receive touch signals (input).

System 600 may also connect to one or more communications networks (e.g. the Internet, a local area network, a wide area network, a personal hotspot etc.) to communicate data to and receive data from networked devices, which may themselves be other computer processing systems.

System 600 may be any suitable computer processing system such as, by way of non-limiting example, a server computer system, a desktop computer, a laptop computer, a netbook computer, a tablet computing device, a mobile/ smart phone, a personal digital assistant, a personal media player, a set-top box, a games console.

Typically, system 600 will include at least user input and output devices 614 (such as a touch screen display) and a communications interface 616 for communication with a network 150.

System 600 stores or has access to computer programs/ software (e.g. instructions and data) which, when executed by the processing unit 602, configure system 600 to receive, process, and output data. Such programs typically include an operating system such as Microsoft Windows®, Apple OSX, Apple IOS, Android, Unix, or Linux.

System 600 also stores or has access to instructions and data (i.e. software applications) which, when executed by the processing unit 602, configure system 600 to perform various computer-implemented processes/methods in accordance with the various embodiments described above. It will be appreciated that in some cases part or all of a given computer-implemented method will be performed by system 600 itself, while in other cases processing may be performed by other devices in data communication with system 600.

Instructions and data are stored on a non-transient machine readable medium accessible to system 600. For example, instructions and data may be stored on non-transient memory 610. Instructions may be transmitted to/received by system 600 via a data signal in a transmission channel enabled (for example) by a wired or wireless network connection. In some embodiments any one or more of the data sources used in a method described herein, can be stored in a remote data storage or server system. In such cases the data can be provided to the system 600 via a data signal in a transmission channel enabled by a wired or wireless network connection. For example, a database storing ChIP-seq information, protein-protein interaction network data, gene sequence database may be located remotely to the system 600 and accessed via a computer network e.g. the internet to enable performance of methods as described herein.

The present invention includes the following non-limiting Examples.

EXAMPLES

Example 1: Data Pre-Processing: Histone Modification ChIP-seq and RNA-seq Data Histone modification data of all available human cell types consisting of primary cells, stem cells and tissues was obtained from ENCODE repository. H3K4me3 ChIP-seq data of 316 samples representing 116 cell types on 20 Apr. 2017 and H3K27me3 ChIP-seq data of 208 samples representing 91 cell types were downloaded on 20 Jan. 2018. The processed ChIP-seq data deposited in ENCODE were obtained by using different processing pipeline parameters or mapped to different human genome versions (hg19 or hg38). Hence, to ensure consistent and cohesive ChIP-seq data processing, histone ChIP-seq and corresponding control/input ChIP-seq sequencing files were downloaded in bam format and realigned the sequencing reads to the hg38 human genome and annotation version V25 using BWA. For datasets made available by Roadmap project, tagAlign FASTA formatted files were provided instead of bam files and tagAlign FASTA files were aligned to the hg38 human genome. The quality of the samples and fragment size were determined using phantompeakqualtools. The ChIP-seq peaks were detected based on the relative enrichment of sequencing reads in the sample (treatment with H3K4me3 or H3K27me3 antibody) to the input (control without antibody). For both H3K4me3 and H3K27me3 ChIP-seq data, broad peaks were called using MACS2 with a q-value threshold of 0.1 for the enrichment of reads in the sample with histone antibody compared to the input sample. For H3K4me3 ChIP-seq data, a systematic peak-quality filtering threshold was identified based on the rate of discarded peaks with an increase in q-value stringency, and it was found that at q-value of $10^{-5}$, the rate of peaks discarded dropped below 10% across all samples. Thus, q-value of $10^{-5}$ was used to filter out low-quality peaks in H3K4me3 ChIP-seq data. For H3K27me3 ChIP-seq data, as many samples were discarded when the q-value stringency was increased to 0.01, the default q-value threshold of 0.1 was used. Additionally, low-quality samples with less than 10,000 peaks were also removed to ensure good quality samples were used to model the cell types. There were 111 and 81 cell types with H3K4me3 and H3K27me3 ChIP-seq data, respectively (FIG. 1A).

Example 2: The EpiMogrify Algorithm

A computational method called "EpiMogrify" has been developed. The method models the epigenetic state of the cell to predict factors important for cell identity, cell maintenance and cell conversion. The major sections of the algorithm are as follows:

(i) Defining histone modification reference peak loci (ii) Identification of cell identity and cell maintenance factors (iii) Identification of cell conversion factors for directed differentiation and transdifferentiation (i) Defining Histone Modification Reference Peak Loci For each cell type, samples were pooled together to obtain cell type representative ChIP-seq profile. The cell type representative ChIP-seq peak breadth was calculated by merging peak regions across the samples and peak height was calculated by the maximum peak height across all samples. To compare the ChIP-seq peaks across various cell types, defined reference peak loci (RPL) was defined, which is a set of regions obtained by combining the representative peaks across all cell types (FIG. 1C). Let n be the number of cell types. For each cell type ranging from x1, x2, . . . xn, let b be the cell type ChIP-seq peak breadth and h be the ChIP-seq peak height. The genomic locations of reference peak loci (RPL) are obtained by merging the peak regions across all cell types. For each locus R1, R2 . . . Rn in RPL, the peak breadth (b) is calculated by merging overlapping peaks across cell types and peak height (h) is given by the maximum peak height of the overlapping peaks.

$$RPL_b = U_{i=1}^{n} b_{xi}$$

$$RPL_h = \max_{i=1}^{n} h_{xi}$$

Protein-coding genes can be assigned to RPL based on the peak's genomic location and the gene's transcription start site (TSS). As H3K4me3 histone modification is a well-known promoter mark, the genes are typically assigned to a peak locus if the peaks overlapped with the gene's promoter region (500 bp from the TSS). However it will be understood that the RPL can be located in another region of the gene relative to its TSS (including expanding the region beyond 500 bp from the TSS, including 1000 bp, 2000 bp or further from the TSS).

Preferably, in each cell type (x), the peak peak breadth value (B) of a gene (g) is calculated as the sum of peak breadth of n peaks annotated to the gene. Whereas the peak height value of a gene is calculated as the maximum height of n peaks annotated to the gene.

$$RPL_b^x$$

is the peak breadth profile of a given cell type x at the RPL (reference peak loci).

$$B_g^x = \sum_{b=1}^{n} (RPL_b^x)$$

(ii) Identification of Cell Identity Genes and Cell Maintenance Factors

Figure 2:
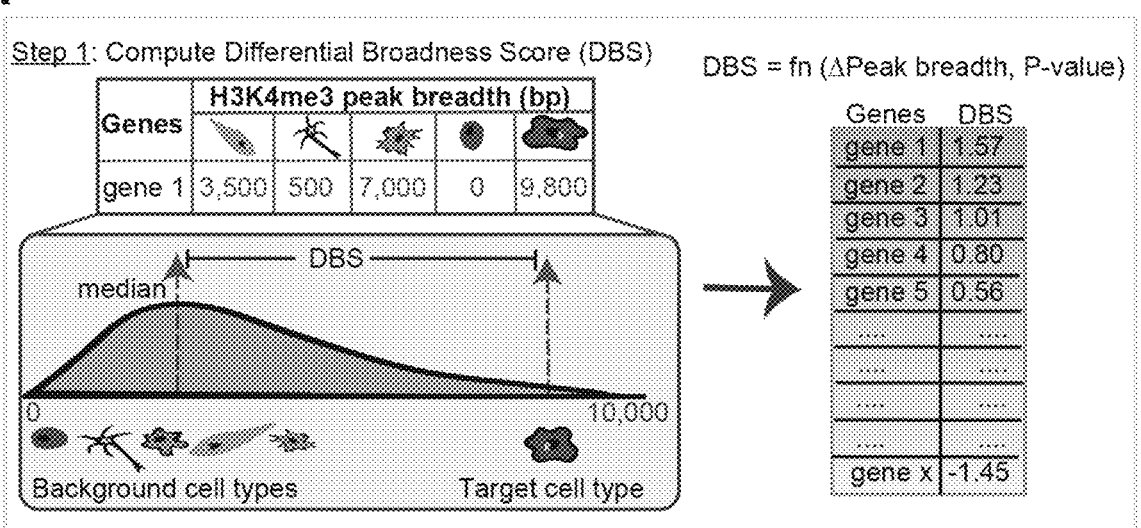
FIG. 2: Identification of cell identity genes and prediction
of signalling molecules for cell maintenance. (A) Schematic
illustration of the data-driven method developed to model
cell identity genes using associated broad H3K4me3 peaks.
For each gene, the Differential Broadness Score (DBS) is
computed by comparing the broad H3K4me3 breadth values
between the target cell type of interest and background cell
types. DBS is a composite score calculated as the difference
in associated breadth value (ΔPeak breadth) and the signifi-
cance of this difference (P-value). The protein-coding genes
are ranked by DBS. (B) To prioritize genes with regulatory
influence, for each gene the Regulatory Differential Broad-
ness Score (RegDBS) is computed as the weighted sum of
the gene's DBS and connected gene's DBS in the protein-
protein interactions (PPI) network. The cell-specific
RegDBS is used to predict (i) cell identity genes and (ii)
signalling molecules for cell maintenance. (C) The enrich-
ment for cell identity geneset by different scoring metrics
such as genes ranked by peak breadth value (Peak breadth),
DBS and RegDBS are computed by GSEA (gene set enrich-
ment analysis). For each scoring metric, the sum of GSEA
enrichment scores (NES*−log 10 p-value) across all cell
types is given. (D) Illustration of EpiMogrify's prediction of
signalling molecules like receptors and ligands for cell
maintenance in vitro. The receptors are produced by the cell
type of interest whereas the ligands can be produced by the
cell type itself or support cell types. The receptor and ligand
pairs are ranked based on the receptor's RegDBS and
corresponding ligand's DBS values. The top predicted
ligands from the ranked receptor-ligand pairs are added to
the culture condition for in vitro cell maintenance.
Figure 2:
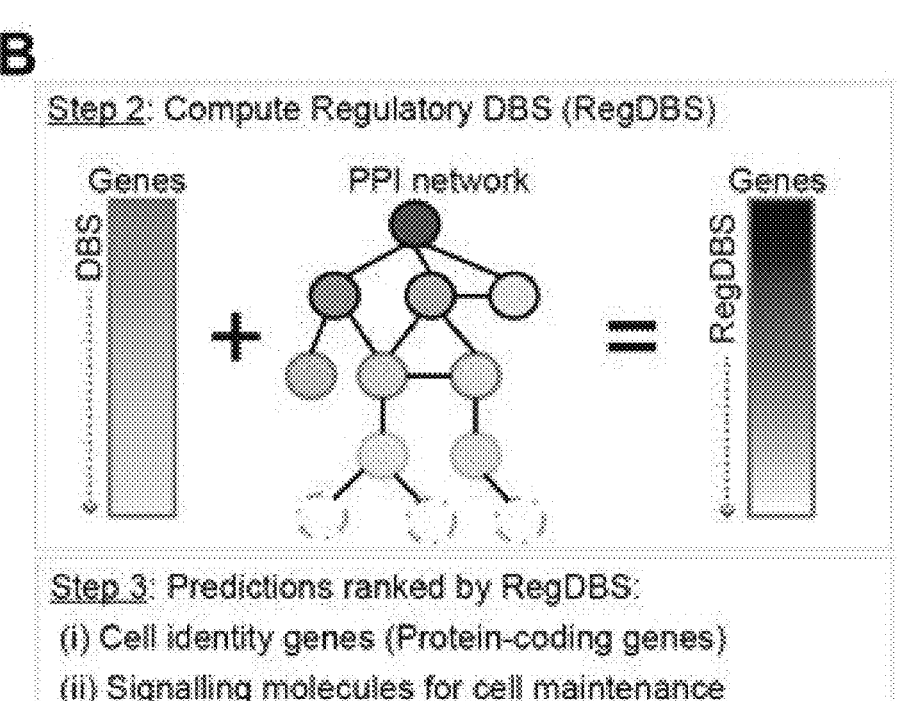
Figure 2:
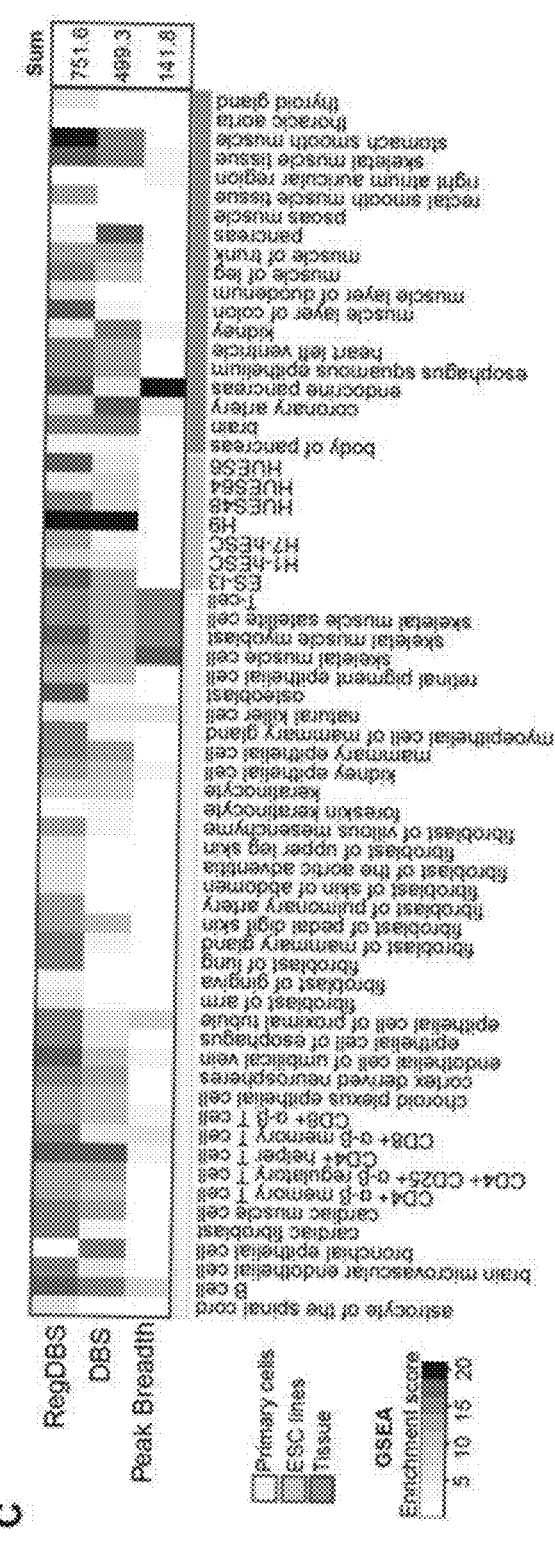

Genes associated with broad H3K4me3 ChIP-seq breadth were observed to be enriched for cell identity genes, hence EpiMogrify employs H3K4me3 ChIP-seq peak breadth to model cell state. Poised genes with the presence of both H3K4me3 and H3K27me3 ChIP-seq peaks at the gene's TSS are removed from this model. EpiMogrify uses a three-step approach to identify factors that are specific to the cell type (FIG. 2). Firstly, the differential broadness score is computed at each RPL based on H3K4me3 ChIP-seq peak breadth. Secondly, the regulatory influence of the gene is determined based on the value of connected genes on the protein-protein interaction network. Finally, cell identity genes are predicted based on the ranked protein-coding genes and EpiMogrify predicts signalling molecules for cell state maintenance.

Step 1: Calculate Differential Broadness Score

The primary cells and stem cells are homogenous cell population, whereas tissue is made of a heterogeneous cell population. Hence primary cells and stem cells were treated as one group and tissue cell types as another group for comparison. To obtain target cell type-specific ChIP-seq profile, the target cell type was compared with a set of background cell types within the group. For example, if the target cell is a primary cell type then the cell types in the background would be the remaining primary and stem cell types. As the cell types in the background set should not be similar to the target cell type, the background cell types were only selected if the Spearman correlation of the ChIP-seq profiles with the target cell type was less than 0.9.

In the target cell type of interest (x), if more than one reference peak locus (RPL) is assigned to the gene (g), then the gene peak breadth score (B) is given by the sum of assigned RPL's peak breadth (b) values. $BG_g^x$ is a set of gene peak breadth scores of background cell types at gene g and the background cell types are selected based on the distinctiveness from the target cell type (x). $\Delta peakbreadth_g^x$ is the normalised difference in gene peak breadth score between target cell type and median gene peak breadth score of background cell types. The significance (p.value) of this difference is estimated by one sample Wilcoxon test. The differential broadness score (DBS) of cell type (x) and gene (g) is measured as the sum of normalised $\Delta peakbreadth$ and Pval.

$$B_g^x = \sum_{b=1}^{n} (RPL_b^x)$$

$$\Delta peakbreadth_g^x = \left[ B_g^x - \text{median}(BG_g^x) \right] / \max_{i=1}^{n} [B - \text{median}(BG_i^x)]$$

$$p.val = \text{one sample Wilcoxon test}(C_g^x, BG_g^x)$$

$$Pval_g^x = -\log 10 \, p.value(B_g^x, BG_g^x) / \max_{i=1}^{n} [-\log 10] p.value(B_i^x, BG_i^x)$$

$$DBS_g^x = \Delta peakbreadth_g^x + Pval_g^x$$

Step 2: Calculate Regulatory Differential Broadness Score

Next, to compute a gene's regulatory influence on cell identity genes of the cell type, STRING V10, a protein-protein interaction network, information was included. The interactions between the gene nodes were selected if the experimental score was greater than zero and the combined score was greater the 500. This ensures that a high-quality network with experimental evidence is used to determine the regulatory influence of the gene. A similar network score (Net) calculation was used, as used in the Mogrify. For all genes in the STRING network (V), network score was computed based on the sum of DBS of connected genes (r) in the gene's sub-network ($V_g$) and corrected for the number of outdegree nodes (O) of the gene and the level (L) of connection. To obtain a cell-specific network, genes with no associated broad H3K4me3 peak from the STRING network were removed. The weighted sum of DBS scores of the connected genes was calculated up to the third level of connection.

$$N_g^x = \sum_{r \in V_g} DBS_r^x / (L_r * O_r)$$

Normalised Network Score (Net) Across all Protein-Coding Genes G in the Cell Types x $$Net_g^x = N_g^x / \max_{i \in G} N_i^x$$

To construct a cell-type-specific network, genes with peak breadth less than the breadth threshold (87%) were removed (FIG. 1E). Different combinations of DBS and Net scores were tested for the enrichment of cell identity genes, and it was determined that a 2:1 ratio of DBS to Network score (Net) showed the highest enrichment for cell identity genes.

$$RegDBS_g^x = DBS_g^x + (0.5 * Net_g^x)$$

Step 3: Predict Cell Identity Genes and Cell Maintenance Factors

EpiMogrify predicts protein-coding genes that mark the cell's identity by ranking the genes based on RegDBS. For cell maintenance, EpiMogrify predicts signalling molecules such as receptor and ligands essential for cell growth and survival. The receptor-ligand interaction pairs were obtained from a study and these pairs were identified based on the gene expression across different cell types. It was noticed that about two-thirds of the ligands are produced by the cell in an autocrine manner and the rest of the ligands are produced by supporting cell types to mimic the microenvironment. Therefore, to incorporate this into the present model, the receptors based on cell-specific RegDBS were prioritised, as they should be both cell-specific and have a regulatory influence on the cell type of interest. Ligands from the cell type of interest and the supporting cell types based on DBS were then prioritized. Finally, the receptor-ligand pairs were prioritized by the combined ranks of receptors and ligands. The ligands in the predicted receptor-ligand pairs can be supplemented to the cell culture conditions.

(iii) Identification of Cell Conversion Factors for Directed Differentiation and Transdifferentiation EpiMogrify employs a three-step approach to identify cell conversion factors. Firstly, for cell conversion from source cell type to target cell type the change in differential broadness score is computed. Then the regulatory influence of the genes exerted on the change in cell state is determined. Finally, transcription factors are predicted for transdifferentiation and signalling molecules are predicted for directed differentiation.

Step 1: Calculate Cell Conversion Differential Broadness Score

For cell conversion, let S be the source cell type and T be the target cell type. First, the differential broadness score (DBS) is computed for both the source and target cell types. Then, to obtain cell conversion ΔDBS, the difference between the source and target DBS scores are computed.

$$DBS_g^S = \Delta peakbreadth_g^S + Pval_g^S$$

$$DBS_g^T = \Delta peakbreadth_g^T + Pval_g^T$$

$$\Delta DBS_g^{T-S} = DBS_g^T - DBS_g^S$$

Step 2: Calculate Cell Conversion Regulatory Differential Broadness Score

Next, the regulatory network score (N) for cell conversion from source cell type to target cell type is computed as the weighted sum of the cell conversion ΔDBS scores of the connected nodes. Similar to the cell-specific RegDBS calculation, the cell conversion RegΔDBS is calculated as the composite score of cell conversion ΔDBS and normalized network score in the ratio of 2:1.

$$N_g^{T-S} = \sum_{r \in V_g} \Delta DBS_r^{T-S} / (L_r * O_r)$$

$$Net_g^{T-S} = N_g^{T-S} / \max_{i \in G} N_i^{T-S}$$

$$Reg\Delta DBS_g^{T-S} = \Delta DBS_g^{T-S} + (0.5 * Net_g^{T-S})$$

Step 3: Predict Cell Conversion Factors for Directed Differentiation and Transdifferentiation For each cell conversion, the protein-coding genes are ranked by RegΔDBS value. For transdifferentiation, EpiMogrify predicts transcription factors (TFs) which are a subset of protein-coding genes defined based on TFClass classification. For directed differentiation, EpiMogrify predicts signalling molecules such as receptors and ligands pairs. The receptors are prioritized by cell conversion RegΔDBS and the corresponding ligands are prioritized by cell conversion ΔDBS. Finally, the receptor-ligand pairs are prioritized by the combined ranks of receptors and ligands. The ligands in the predicted receptor-ligand pairs can be supplemented to the differentiation protocol.

In summary, EpiMogrify models the broad H3K4me3 histone modification feature and predicts cell identity protein-coding genes, signalling molecules for cell maintenance, signalling molecules for directed differentiation and TFs for transdifferentiation.

Example 3: Characteristics of H3K4me3 and H3K27me3 Histone Modifications

The cell state can be modelled by leveraging on epigenetic histone modifications, namely H3K4me3 and H3K27me3 modifications, which are well-known transcriptional activator and repressor marks, respectively. ChIP-seq data were obtained for H3K4me3 and H3K27me3 histone modification profiles of various human cell types from ENCODE and Roadmap consortia data repositories. To ensure consistent downstream processing of ChIP-seq datasets across different samples and experiments, an analysis pipeline was implemented and, when needed, data-driven thresholds were used to call significant peaks in the H3K4me3 and H3K27me3 profiles. After filtering low-quality peaks, samples representing 111 distinct cell types (51 primary cells, 53 tissue, 7 stem cells) with H3K4me3 profiles and 81 cell types (28 primary cells, 45 tissue, 8 stem cells) with H3K27me3 profiles (FIG. 1A) were retained. To investigate the effect of histone modifications on the transcriptional state, gene expression profiles from ENCODE consisting of 137 cell types (64 primary cells, 68 tissue, 5 stem cells) were used. There are 40 common cell types with epigenetic (by H3K4me3 and H3K27me3 ChIP-seq) and transcriptional (by RNA-seq) data available. The breadth of a ChIP-seq peak was defined as the length of the genomic region with histone modification deposition in base pairs (bp), and the height of a ChIP-seq peak as the average enrichment of histone modification or signal value (FIG. 1B). The ChIP-seq peak breadth ranges from narrow to broad peaks and ChIP-seq peak height ranges from short to tall peaks and the distributions across all cell types. Furthermore, compared to H3K4me3, H3K27me3 had a higher number of narrow and broad ChIP-seq peaks, and H3K27me3 is known to be present in intergenic regions and silent genes.

Next, the genomic location preference of H3K4me3 and H3K27me3 ChIP-seq profiles was determined across all cell types. The frequency of ChIP-seq peaks within a window of 2000 bp around the protein-coding genes' transcription start site (TSS) was assessed. It was noticed that H3K4me3 had a higher frequency of peaks within 500 bp from the TSS in contrast to H3K27me3 mark.

Next, H3K4me3 and H3K27me3 ChIP-seq profiles were annotated to protein-coding genes, and to this aim, a gene value was assigned based on associated ChIP-seq peak breadth or height. FIG. 1C shows a detailed schematic of the annotation of protein-coding genes and assigned gene values. For each cell type, cell type representative H3K4me3 and H3K27me3 ChIP-seq peak profiles were obtained by merging multiple samples or replicates (see Methods for details). Next, reference ChIP-seq peak regions were defined, called reference peak loci (RPL), which are obtained by merging overlapping peaks across cell types. For each RPL, protein-coding genes to the locus were annotated when the gene's promoter region overlaps with the locus. For H3K4me3 mark, the promoter region was defined as 500 bp from the gene's TSS as it was found the presence of higher frequency of H3K4me3 ChIP-seq peaks in this region. For H3K27me3 mark, the promoter region was defined as −500 bp from gene's TSS in order to exclude accounting for H3K27me3 mark at gene introns. The table in FIG. 1C gives an example of gene annotation to RPL and the respective gene values based on ChIP-seq peak breadth and height for each cell type.

Example 4: A Data-Driven Approach to Model H3K4me3 Profiles to Identify Cell Identity Genes To determine the best feature to model a cell's identity, histone modification features like ChIP-seq peak breadth and height, and transcriptional feature like gene expression level were tested. Firstly, protein-coding genes were grouped in five percentile bins based on the distributions of H3K4me3 and H3K27me3 ChIP-seq peak breadth and height, and gene expression. Next, it was estimated whether any of histone modification or gene expression features are enriched for cell identity genes exclusively. Cell identity genes were defined by text-mining of cell type related GO biological processes, and the significance of enrichment was calculated by Fisher Exact Test (FET). It was observed that across all cell types, bins with high gene expression showed a higher significance of enrichment for both cell identity genes and housekeeping genes It was found that tall H3K4me3 ChIP-seq peaks enrich for housekeeping genes, while broad H3K4me3 ChIP-seq peaks significantly enriched for cell identity genes as shown in previous studies. As expected the H3K27me3 repressor mark did not enrich for cell identity or housekeeping genes across all cell types. As genes with either high gene expression or broad H3K4me3 ChIP-seq peaks significantly enrich for cell identity genes, these features were further examined to identify the best metric (H3K4me3, RNA-seq expression or both) to model cell identity genes. For 40 common cell types, genes based on their gene expression or H3K4me3 ChIP-seq peak breadth were ordered in descending order and genes are grouped in a cumulative window increasing by one percentile (FIG. 1D). For each cumulative window, the significance of enrichment was computed for cell identity and housekeeping genes across common cell types. It was found that high gene expression is associated with both cell identity and housekeeping genes, whereas genes marked by broad H3K4me3 ChIP-seq peaks were exclusively enriched for cell identity genes (FIG. 1D). Next, to determine a threshold of H3K4me3 ChIP-seq peak breadth that can efficiently identify cell identity genes, the significance of enrichment for cell identity genes was examined. It was found that H3K4me3 ChIP-seq peak breadth above 87th percentile of the distribution of peak breadths had the highest significance of enrichment across 111 cell types (FIG. 1E). For each cell type, this threshold (87th percentile) corresponds to a ChIP-seq peak breadth ranging from 3,611 to 15,035 base pairs. Taken together, these analyses suggest that broad H3K43 ChIP-seq peak breadth is a feature that is associated with cellular identity.

Next, a data-driven method and a "gene score" were developed to model cell state and identify cell-specific genes by systematically analysing the broad H3K4me3 ChIP-seq peak feature. To identify cell-specific genes, the target cell type of interest was compared to background cell types. The background cell types were selected based on the distinctiveness from the target cell type calculated by Spearman correlation. FIG. 2A shows a schematic of the approach used to prioritize cell-specific genes. For each cell type and protein-coding genes, the differential broadness score (DBS) was computed, which is a composite score calculated by the difference in ChIP-seq peak breadth between the target cell type and background, and the significance of this difference. Protein-coding genes ranked by DBS are cell-specific genes and to prioritize cell-specific genes which possess a regulatory influence on the cell, the regulatory differential broadness score (RegDBS) was computed (FIG. 2B). RegDBS is a composite score calculated by the gene's DBS and protein-protein interaction network score. Using this approach, it was possible to systematically prioritize cell-specific protein-coding genes for 111 cell types and ranked each gene by RegDBS score.

It was asked whether this method improves the accuracy of detecting cell identity genes compared to a previous study. Different scoring metrics that models the H3K4me3 ChIP-seq peak breadth were compared by measuring the enrichment for cell identity genes using GSEA (Gene Set Enrichment Analysis) (FIG. 2C). It was found that, compared to ranking protein-coding genes by H3K4me3 ChIP-seq peak breadth alone, DBS showed 2.5, 3.5 and 3.5 fold more enrichment for cell identity genes, respectively. RegDBS had the highest enrichment for cell identity genes across all cell types and about 5.3 fold increase in enrichment compared to genes ordered by peak breadth and 1.5 fold increase compared to DBS. This confirms that the present method has higher accuracy in identifying genes with a ontology associated with cellular identity. In particular, the RegDBS score, which makes use of regulatory network information, can be used to prioritize cell-specific genes.

Example 5: EpiMogrify Predicts Factors for Cell Maintenance, e.g., Astrocytes As the present method can efficiently prioritize cell identity genes, it was hypothesized that the prioritized signalling molecules like receptors and ligands would be essential for cell survival and maintenance of cell state. EpiMogrify's approach to predicting signalling molecules for cell maintenance is shown in FIG. 2D. It was hypothesized that by prioritizing the receptors based on RegDBS metric, it would be possible to identify receptors that could trigger the activation of the cell identity genes as these receptors are weighted by their regulatory influence. Whereas, the ligands required to activate with these receptors can either be produced by the target cell type in an autocrine manner or by support cell types in a paracrine manner. Hence, the corresponding ligands were prioritised by DBS and ranked receptor-ligand pairs important for the target cell type were obtained (FIG. 2D). When cells are transferred from an in vivo system to an in vitro condition, they would be expressing the required receptors. However, the ligands needed to activate these receptors might be lost. Therefore, for cell maintenance in vitro, it was hypothesised that EpiMogrify could predict ligands that could be added to the cell maintenance culture media. To assess the accuracy of EpiMogrify's predictions, the predicted ligands for growth and maintenance were tested on astrocytes in vitro. Astrocytes are a multifunctional cell type that provides metabolic and structural support for neurons, regulates neurogenesis and brain wiring, and any dysfunction of astrocytes can lead to major neurological diseases. Therefore, to study neurological diseases, it is vital to improve the ability to expand and maintain astrocytes.

For astrocyte cell maintenance, the top seven signalling molecules predicted by EpiMogrify are components in the extracellular matrix (ECM) like FN1, COL4A1, LAMB1 and COL1A2, and secreted ligands like ADAM12 and EDIL3. As LAMB1 is a part of laminin trimer, the astrocyte-specific laminin 211 complex which consists of LAMA2, was used and predicted LAMB1 and predicted LAMC1. The predicted factors were tested in astrocytes obtained from two different sources: astrocytes differentiated from neural stem cells and primary astrocytes. Astrocytes were cultured in culture conditions by supplementing the predicted signalling molecules individually and together. Culture media which did not include additional ligands was used as a negative control and also compared with Matrigel as a positive control.

Figure 3:
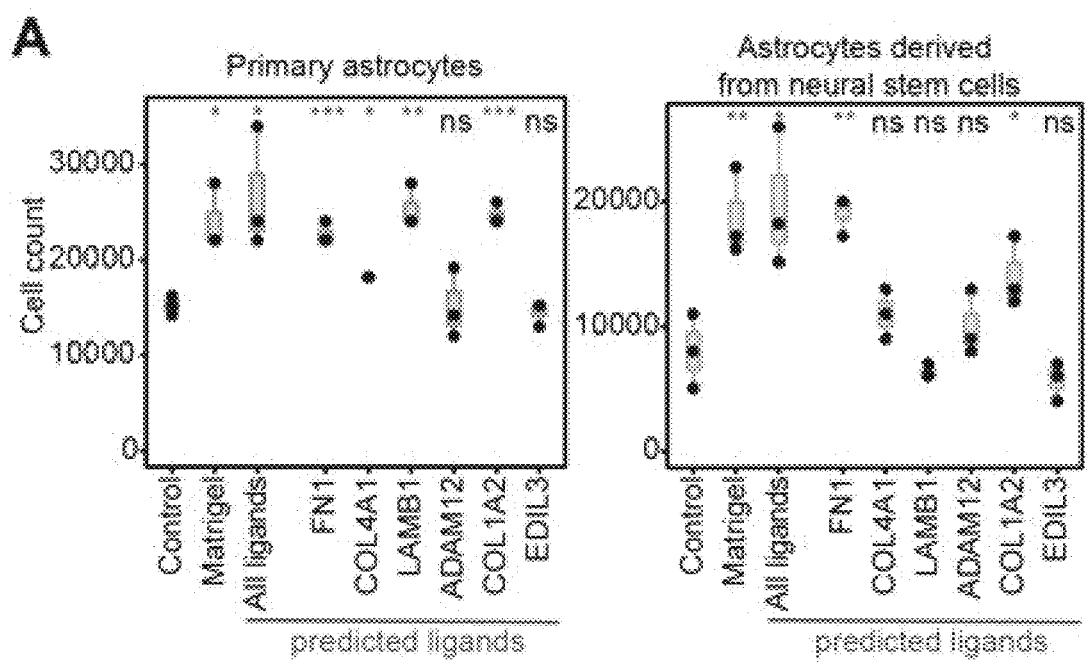
FIG. 3: Cell maintenance of astrocytes in vitro. A) The
cell count at day 3 after supplementing with the predicted
ligands in astrocyte primary cell culture and astrocytes
derived from neural stem cells. The control is without any
supplements and matrigel is used as the golden standard. B)
Cell proliferation rate of primary astrocytes and astrocytes
derived from neural stem cells, detected by cell proliferation
assay (BrdU) at day 3 after supplementing with predicted
factors. C) Immunofluorescence (IF) images for astrocyte-
specific markers such as GFAP (Red) and S100b (Green) on
primary astrocytes under the specified culture conditions.
(D) Similarly, IF images for astrocyte-specific markers on
astrocytes derived from neural stem cells under the specified
culture conditions. Cells were counterstained with DAPI.
Scale=25 μm. Unpaired one-tailed t-test was used to com-
pare the predicted conditions with control. *P<0.05,
P<0.01, *P<0.001, ****P<0.0001 and ns not signifi-
cant.
Figure 3:
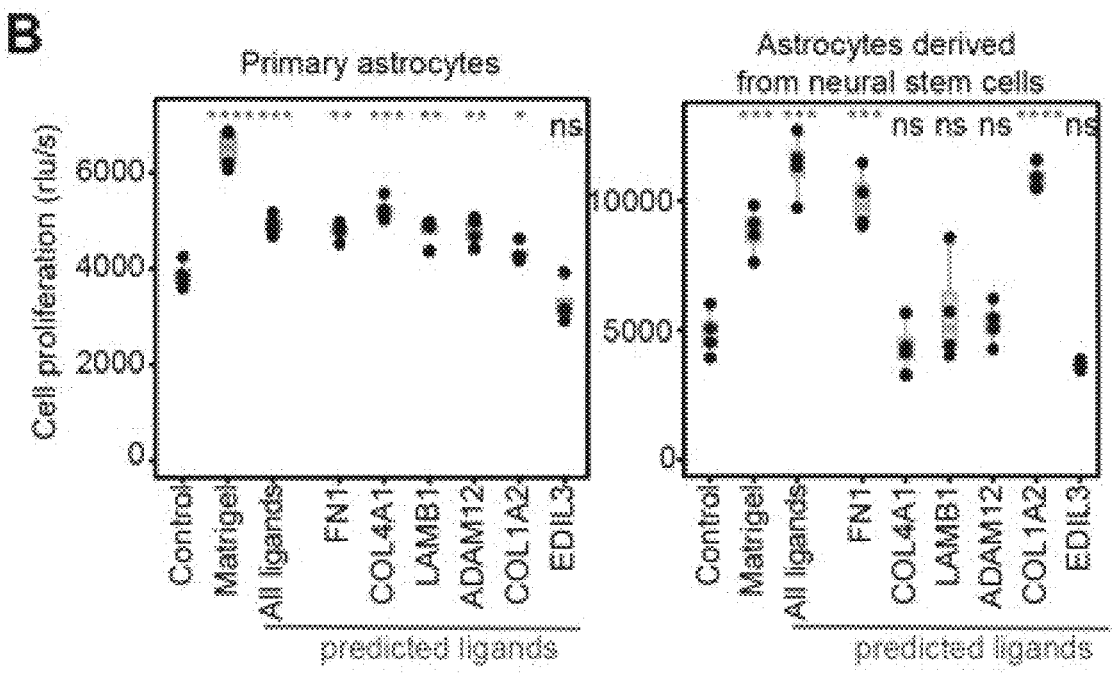
Figure 3:
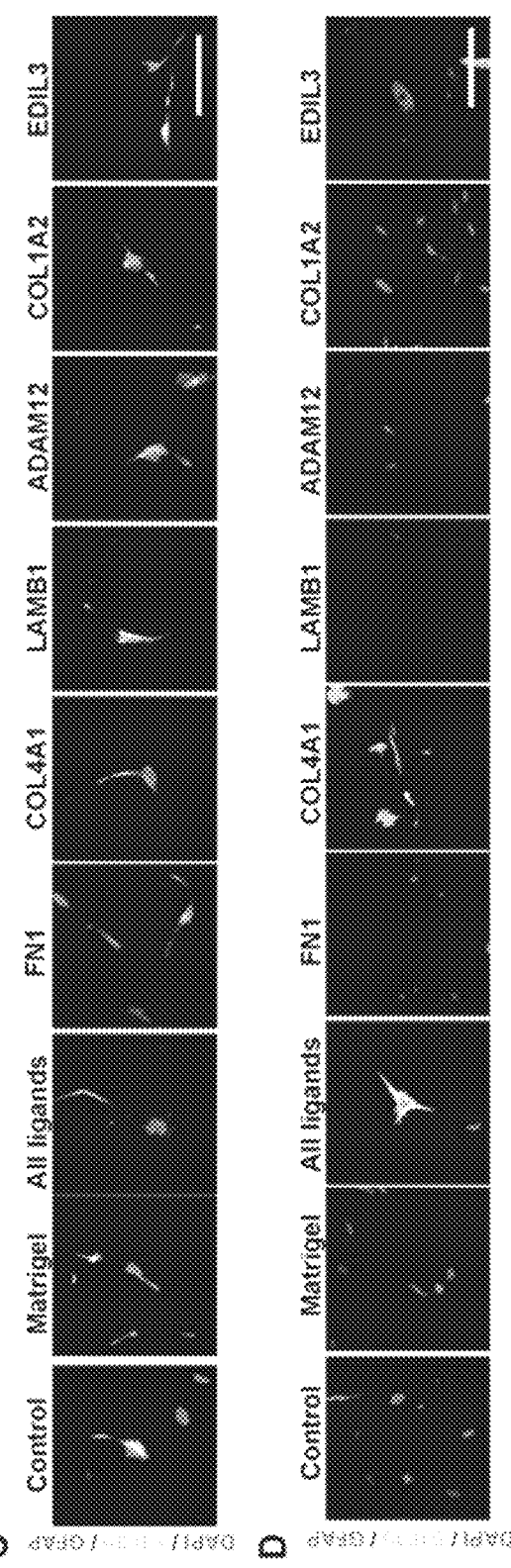

It was found that a significant increase in cell growth in culture conditions with EpiMogrify predicted factors as compared with Matrigel. (FIGS. 3A and 3B) Next, immunofluorescence for astrocyte markers such as S100b and GFAP was performed, and it was confirmed that the increase in growth rate did not affect the cellular identity with cells expressing both markers in astrocytes differentiated from neural stem cells and primary astrocytes (FIGS. 3C and 3D). It was shown that using only few signalling molecules (such as FN1, COL1A2 or LAMB1) cell maintenance was achieved and, in some cases, the growth efficiency was equivalent to using Matrigel which is a chemically undefined complex.

Example 6: EpiMogrify Predicts Factors for Cell Maintenance, e.g., Cardiomyocytes For cardiomyocyte (cardiac cell) maintenance, the top seven signalling molecules predicted by EpiMogrify were FN1, COL3A1, TFPI, FGF7 and APOE. Cardiomyocytes were cultured in culture conditions by supplementing the predicted signalling molecules individually and together. Culture media which did not include additional ligands was used as a negative control and also compared with Geltrex as a positive control.

Figure 4:
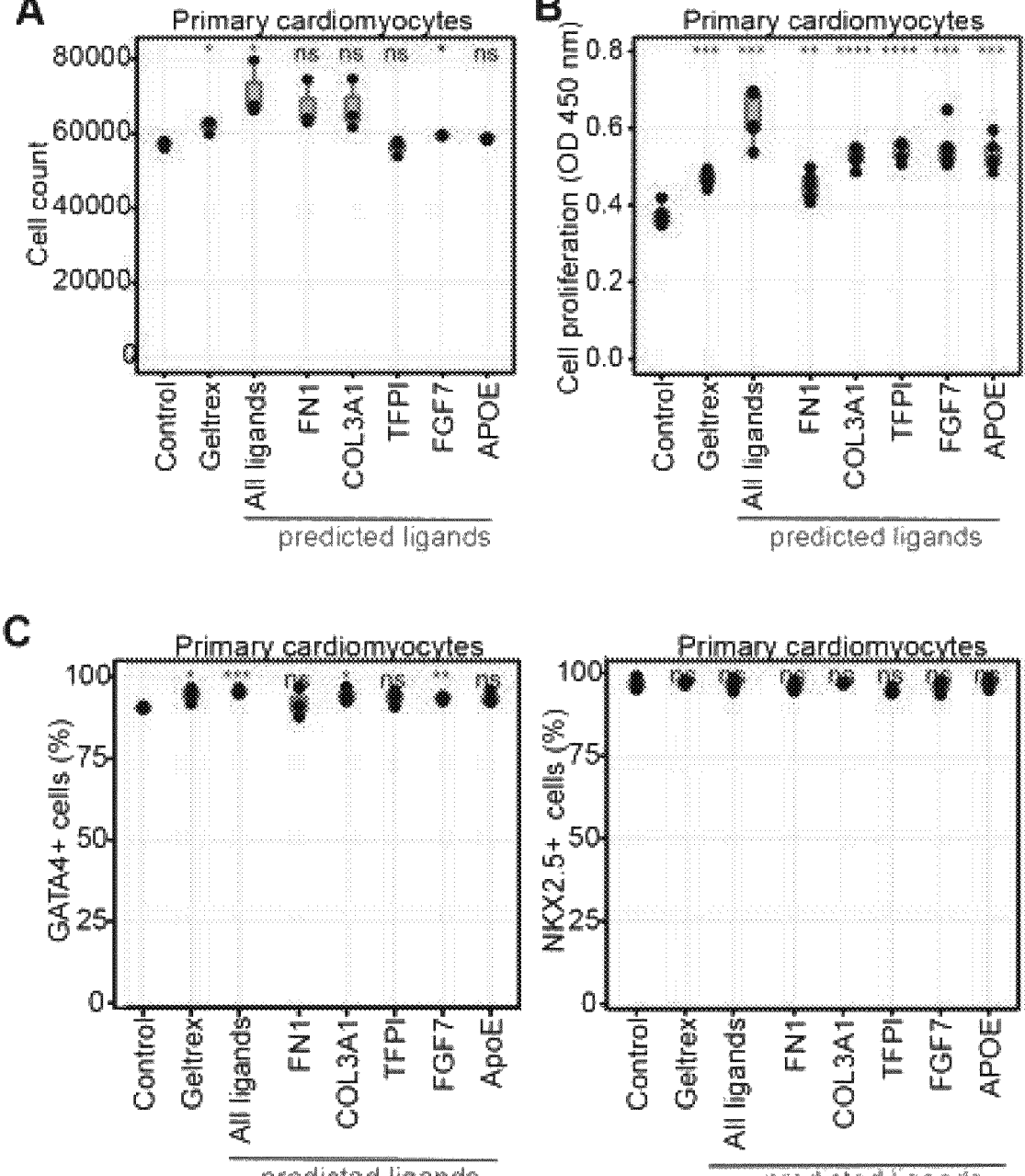
FIG. 4: Cell maintenance of astrocytes in vitro. A) The
cell count at day 3 after supplementing with the predicted
ligands in cardiomyocytes. The negative control is a condi-
tion without additional ligands and positive control in the condition with Geltrex only. B) Cell proliferation rate of cardiomyocytes detected by cell proliferation assay (BrdU) at day 3 after supplementing with the predicted ligands. C) Fluorescence-activated cell sorting (FACS) for cardiomyocyte marker GATA4+ and NKX2.5+ cells for all conditions. Unpaired one-tailed t-test was used to compare the predicted conditions with control. *P<0.05, P<0.01, *P<0.001, ****P<0.0001 and ns not significant.

It was found that a significant increase in cell growth in culture conditions with EpiMogrify predicted factors as compared with Geltrex. (FIGS. 4A and 4B) Next, immunofluorescence for cardiomyocyte markers such as GATA4 and NKX2.5 was performed, and it was confirmed that the increase in growth rate did not affect the cellular identity with cells expressing both markers (FIG. 4C).

Example 7: EpiMogrify Predicts Factors for Cell Maintenance, e.g., Smooth Muscle Cells Next, EpiMogrify predicted conditions were tested to determine if these can facilitate smooth muscle cell maintenance in vitro. To test the predictions in smooth muscle cells, human pulmonary artery smooth muscle cells (HPASMC) were cultured in vitro.

As the H3K4me3 ChIP-seq data for HPASMC was unavailable, the H3K4me3 profile of closest available cell-type "tissue: stomach smooth muscle" was used to predict ligands for smooth muscle cell maintenance. The top 13 ligands predicted by EpiMogrify for smooth muscle cell maintenance are LAMA5, COL4A1, LAMA4, NID1, COL6A3, COL4A6, COL4A5, FGF10, FGF7, GNAS, COL7A1, COL1A1 and THBS1. Some of these predictions are subunits of a complex protein like Collagen 4, which comprises predicted subunits COL4A1, COL4A6 and COL4A5, Collagen 6 is made of COL6A3, and Collagen 1 is made of COL1A1. Hence, Collagen 4, NID1, Collagen 6, FGF10, FGF7, Collagen 1 and THBS1 were tested for the maintenance of smooth muscle cells. Smooth muscle cells were cultured by supplementing the predicted ligands individually or all together in the culture condition, a culture condition with no additional ligands as a negative control and a culture condition with the chemically undefined complex mixture (Geltrex) as a positive control.

Figure 5:
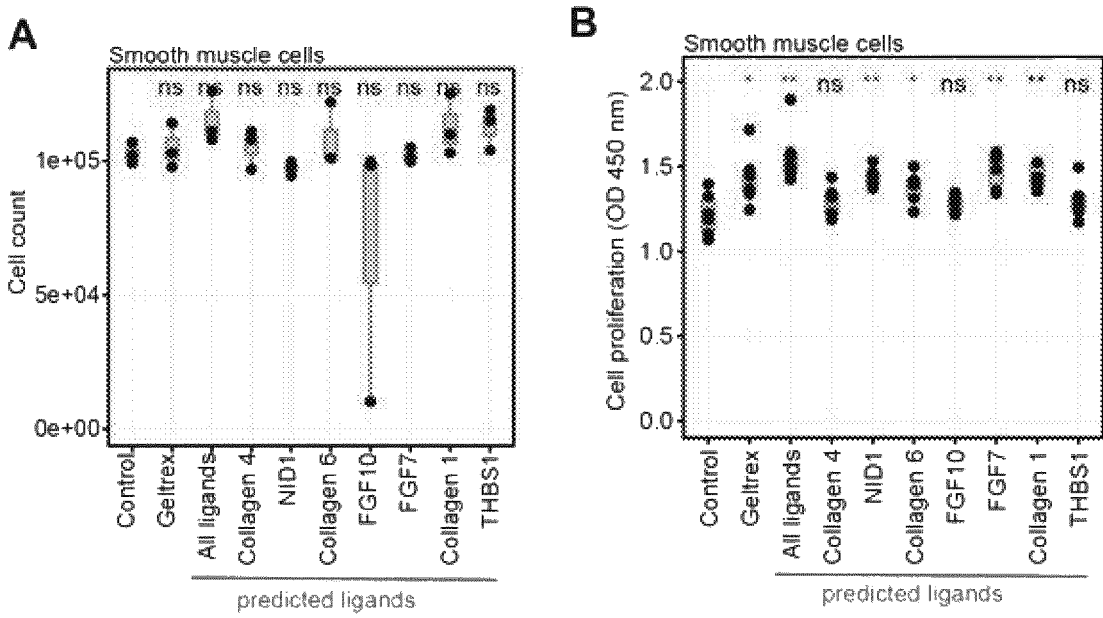
FIG. 5: Cell maintenance of HPASMC smooth muscle cells in vitro. (A) The cell count at day 3 and day 6 after supplementing with the predicted ligands in HPASMC smooth muscle cells. The negative control is a condition without additional ligands and positive control is the condition with Geltrex only. (B) The cell proliferation rate of smooth muscle cells detected by cell proliferation assay (BrdU) at day 3 after supplementing with predicted ligands. (C) Fluorescence-activated cell sorting (FACS) for smooth muscle cell-specific marker α-SMA+ cells for all the conditions. (D) Immunofluorescence images for smooth muscle cell-specific markers such as SM22 (Green) on smooth muscle cells under the specified culture conditions. Cells were counterstained with Hoechst. Scale=50 µm. Unpaired one-tailed t-test was used to compare the predicted conditions with control. *P<0.05, P<0.01; *P<0.001; ****P<0.0001 and ns not significant.
Figure 5:
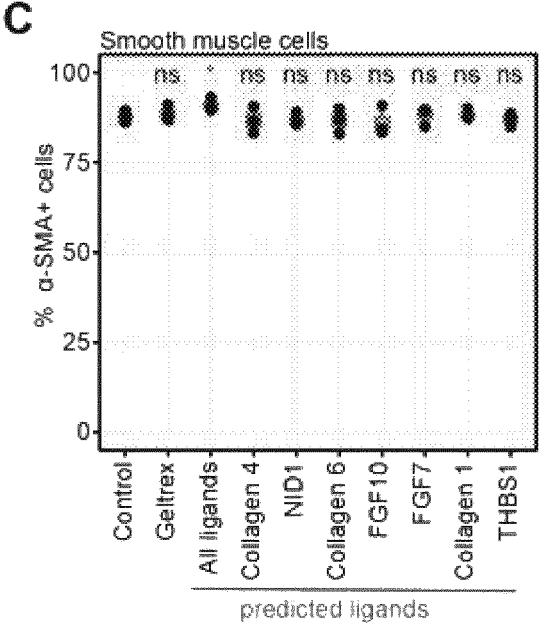
Figure 5:
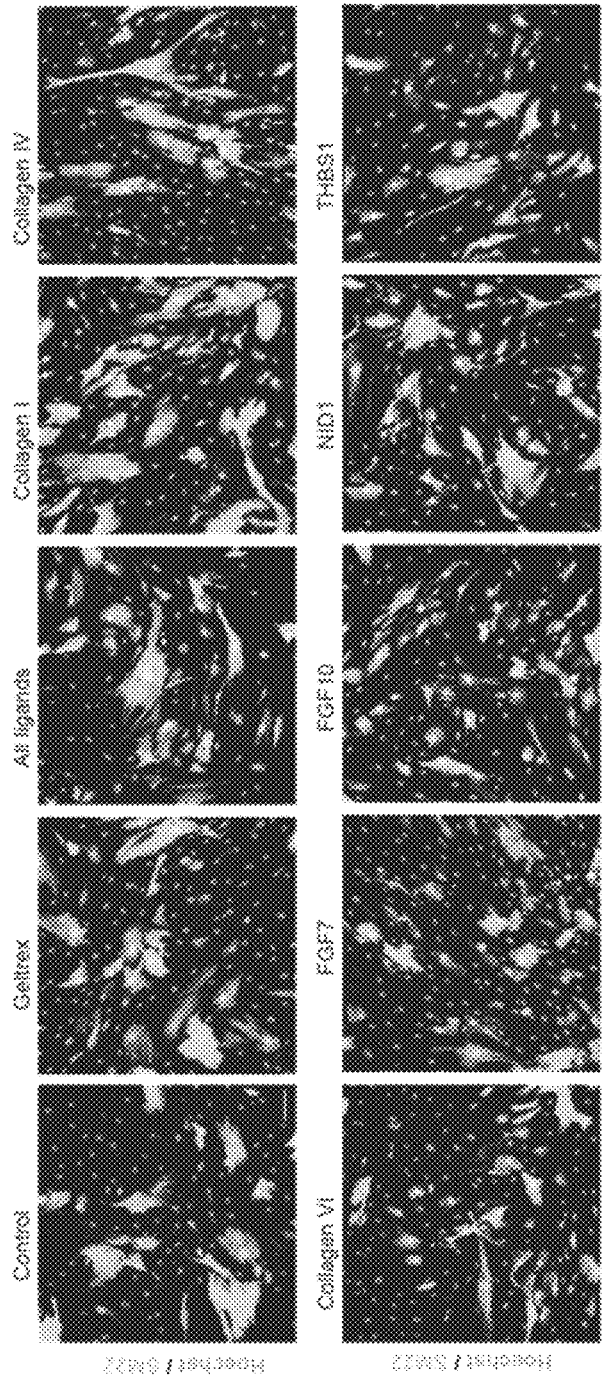

In order to assess the efficacy of the predictions, the number of cells were counted together with an assessment of the proliferation rate as a proxy for cell growth in each condition. A significant increase in proliferation rate amongst culture conditions with EpiMogrify predicted ligands (such as All ligands together, Collagen 6, Collagen 1, NID1 and FGF7) was observed, compared to the negative control (FIGS. 5A and 5B). In addition, smooth muscle cells in maintenance conditions containing all EpiMogrify predictions expressed significantly higher percentage of smooth muscle marker α-SMA compared to negative control (FIG. 5C). Next, immunofluorescence for smooth muscle marker SM22 was performed to show that EpiMogrify predicted conditions retained the cell's identity (FIG. 5D).

Example 8: Epimogrify Predicts Factors for Cell Maintenance, e.g., Endothelial Cells To test the predictions in endothelial cells, we cultured primary human aortic endothelial cells (HAoEC) in vitro. As the H3K4me3 ChIP-seq data for HAoEC was unavailable, the H3K4me3 profile of closest available cell-type "primary cell: endothelial cells of umbilical vein" was used to predict ligands for endothelial cell maintenance. The top ten ligands predicted by EpiMogrify for endothelial cell maintenance are BMP6, ADAM9, LAMB1, LAMA4, THBS1, CTGF, BMP4, PDGFB, FN1 and CYR61. Of these, BMP6, THBS1, CTGF, BMP4, PDGFB, FN1 and CYR61 were tested in HAoEC endothelial cell maintenance.

Figure 6:
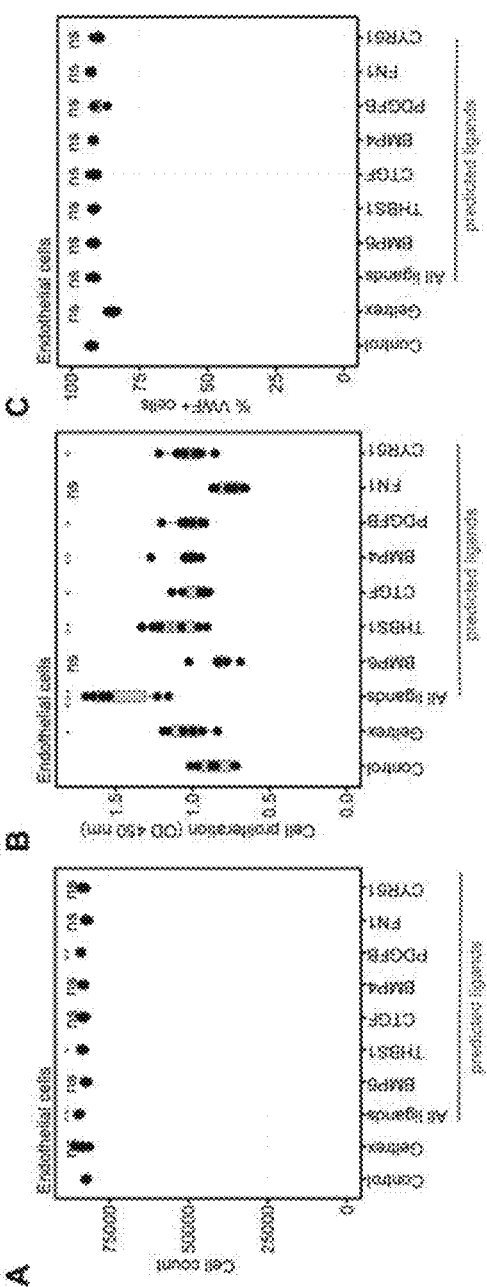
FIG. 6: Cell maintenance of HAoEC endothelial cells in vitro. (A) The cell count at day 3 and day 6 after supplementing with the predicted ligands in HAoEC endothelial cells. The negative control is a condition without additional ligands and positive control is the condition with Geltrex only. (B) The cell proliferation rate of endothelial cells detected by cell proliferation assay (BrdU) at day 3 after supplementing with predicted ligands. (C) FACS for endothelial cell-specific marker VWF+ cells for all the conditions. (D) IF for endothelial cell-specific marker CD31 (green) for all the conditions. Cells were counterstained with Hoechst. Scale=50 µm. Unpaired one-tailed t-test was used to compare the predicted conditions with control. *P<0.05, P<0.01; *P<0.001; ****P<0.0001 and ns not significant.
Figure 6:
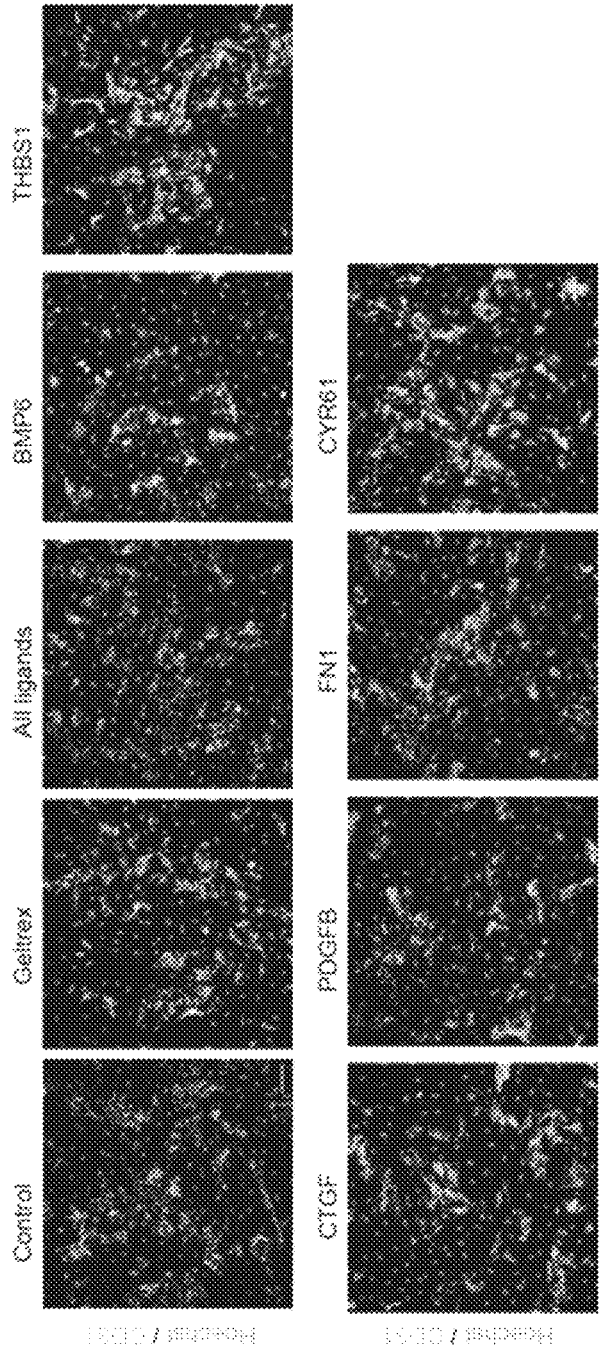

A similar experimental design to that used for smooth muscle cells was employed to maintaining endothelial cells in EpiMogrify-predicted conditions (combined and individual) and compared against both negative and positive controls (Geltrex). The EpiMogrify-predicted conditions (all ligands together and individual factors such as PDGFB, THBS1, CTGF, BMP4, PDGFB and CYR61) were able to maintain significantly higher cell number and proliferation rate compared to the negative control (FIGS. 6A and B). Furthermore, the EpiMogrify-predicted conditions expressed endothelial-markers CD31 and VWF (FIGS. 6C and D). Though there was no significant increase in cells that expressed VWF marker compared to negative control, there was a significant increase in cells expressing the marker compared to a chemical un-defined complex (Geltrex) in EpiMogrify defined conditions (condition with individual ligands and all ligands together).

Example 9: EpiMogrify Predicts Factors for Cell Conversion, e.g., Astrocytes

Figure 7:
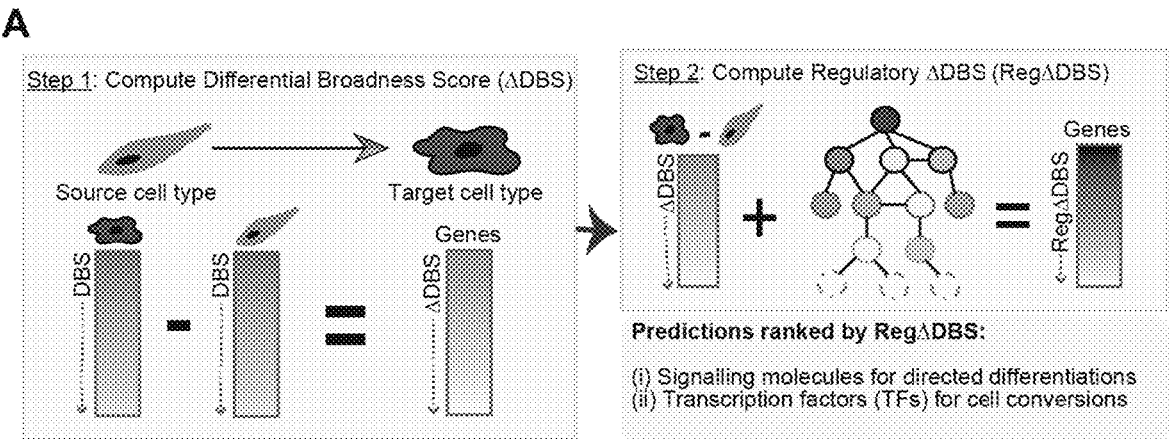
FIG. 7: EpiMogrify: prediction of cell conversion factors. (A) For cell conversion from source to target cell type, the change in cell identity is computed as the difference in DBS value between the source and target cell types. Then a cell conversion RegΔDBS is calculated as the sum of the gene's ΔDBS and protein-protein interaction network score. The genes are ranked by cell conversion RegΔDBS to predict (i) signalling molecules for directed differentiation or cell conversion and (ii) transcription factors for transdifferentiation. (B) For x number of cell conversions, the enrichment of EpiMogrify's predicted list of TFs against (i) top 100 TFs predicted by JSD, (ii) redundant TF set by Mogrify and (iii) common TFs predicted by both JSD and Mogrify is calculated using GSEA. The graph shows the percentage of cell conversions with significant enrichment in each case. (C) For transdifferentiation from fibroblasts (source cell type) to selected 10 target cell types, the table summarizes the overlap between EpiMogrify's predicted TFs with previously published TFs for the same in vitro transdifferentiation. For each transdifferentiation, the percentage of recall of published TFs and their respective ranks are given.
Figure 7:
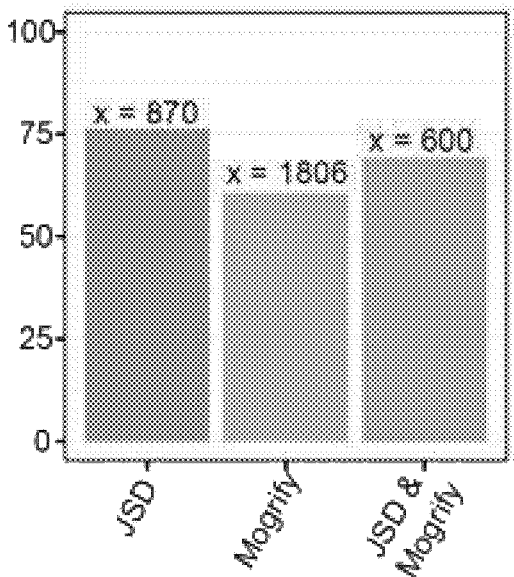
Figure 7:
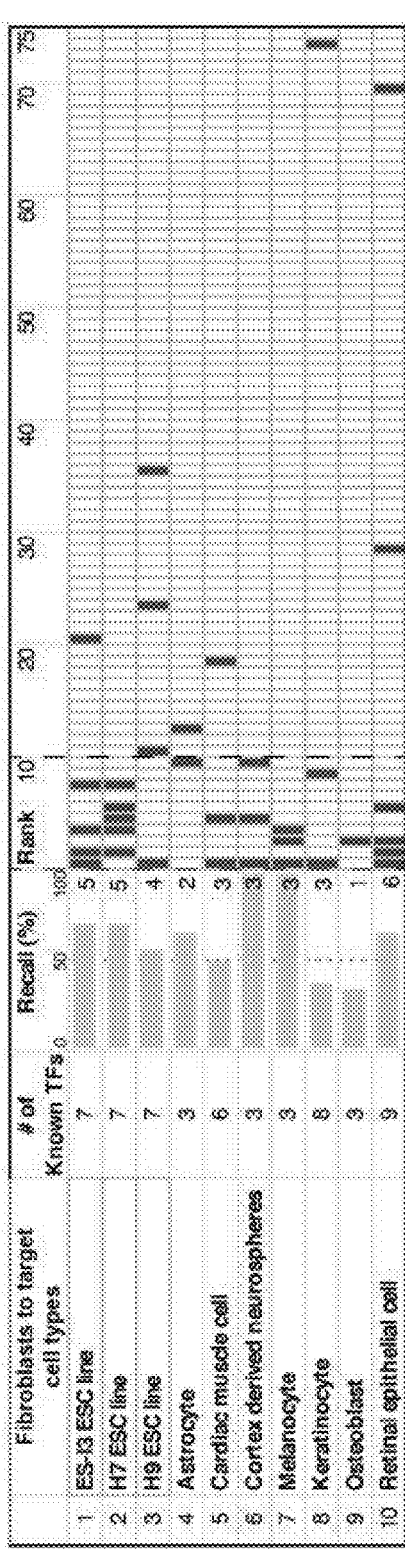

Since EpiMogrify predicts factors that can maintain cell state, it was hypothesised that by modelling the change in cell state factors required for cell conversion could be identified. FIG. 7A shows a detailed schematic of cell conversion score calculation for change in cell state from source cell type to target cell type. The genes specific for the change in cell state can be prioritised based on the difference in the gene's DBS between target and source cell types. Next, each gene is weighted based on the regulatory influence it exerts on the change of cell state to derive the RegΔDBS score for each gene. For each cell conversion, EpiMogrify prioritizes protein-coding genes (including TFs and signalling molecules) which are ranked by RegΔDBS. A few experimentally validated methods exists to model the transcriptional state of the cell (or change in transcriptional state) and identify TFs for cell conversion, including Cell-Net, D'Alessio A C et al (referred to as "JSD" here as it uses Jensen-Shannon divergence statistics) and Mogrify. The epigenetic-based EpiMogrify's predictions were compared with transcription-based computational methods' predictions. There were 29 common cell types between EpiMogrify and JSD, 43 between EpiMogrify and Mogrify, and 25 between all three methods. Using GSEA it was found that for common cell conversions, the TFs predicted by EpiMogrify had significant enrichment for TFs predicted by JSD (76.4% of all conversions), Mogrify (60.7%) or by both JSD and Mogrify (69.3%) (FIG. 7B). Significant overlap between EpiMogrify predicted TFs and other methods was found. A high occurrence of published TFs among the top 10 predicted by EpiMogrify (FIG. 7C), indicates EpiMogrify's high accuracy in identifying TFs for cell conversion.

Next, EpiMogrify was applied to prioritize signalling molecules for directed differentiation from embryonic stem cells to astrocytes. Predicted signalling molecules were tested in the differentiation protocol.

Figure 8:
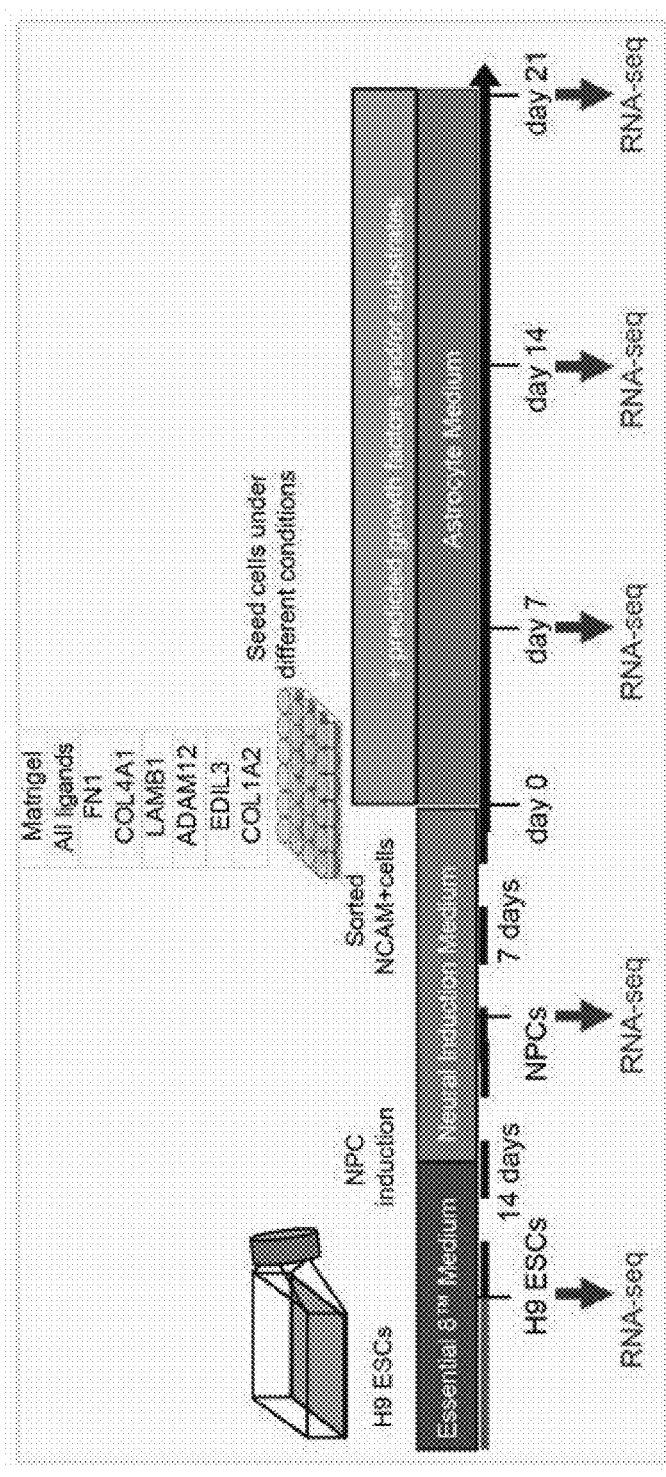
FIG. 8: Directed differentiation of astrocytes in vitro. (A) Schematic diagram of astrocyte in vitro differentiation from H9 embryonic stem cells (H9 ESCs). After 14 days, Neural cell adhesion molecule (NCAM)+ neural progenitor cells were selected and the cells were seeded under different predicted conditions. Immunofluorescence (IF), Fluorescence-activated cell sorting (FACS) and RNA-seq analyses were performed. (B) FACS for astrocytic marker CD44+ cells for all the conditions. (C) IF of GFAP (Red) and S100b (Green) at day 21 in Matrigel only and in all ligands conditions. (D) IF was performed to obtain the percentage of DAPI+ cells with GFAP and S100b astrocytic markers in all conditions. € For a group of genes that indicates astrocyte specificity (astrocytic transcriptional signatures), the mean z-score of the gene expression profile in TPM is calculated across three samples which were sequenced at each timepoint and condition. The astrocytic transcriptional signatures are (i) significantly upregulated genes between H9 ESCs and primary astrocytes obtained from our RNA-seq data, (ii) significantly upregulated genes between H9 ESCs and astrocytes from cerebral cortex obtained from FANTOMS (F5) database, (iii) significantly upregulated genes between H9 ESCs and astrocytes from cerebellum obtained from F5 database, (iv) EpiMogrify GRN (gene regulatory network) is a geneset containing primary astrocyte cell identity genes with a positive RegDBS score and the connected genes on the STRING network upto first neighbours that are regulated and (v) HumanBase GRN is an astrocyte-specific network obtained from HumanBase database. Cells were counterstained with DAPI. Scale=25 µm. Unpaired one-tailed t-test was used to compare the predicted conditions with control. *P<0.05, P<0.01; *P<0.001 and ns not significant.
Figure 8:
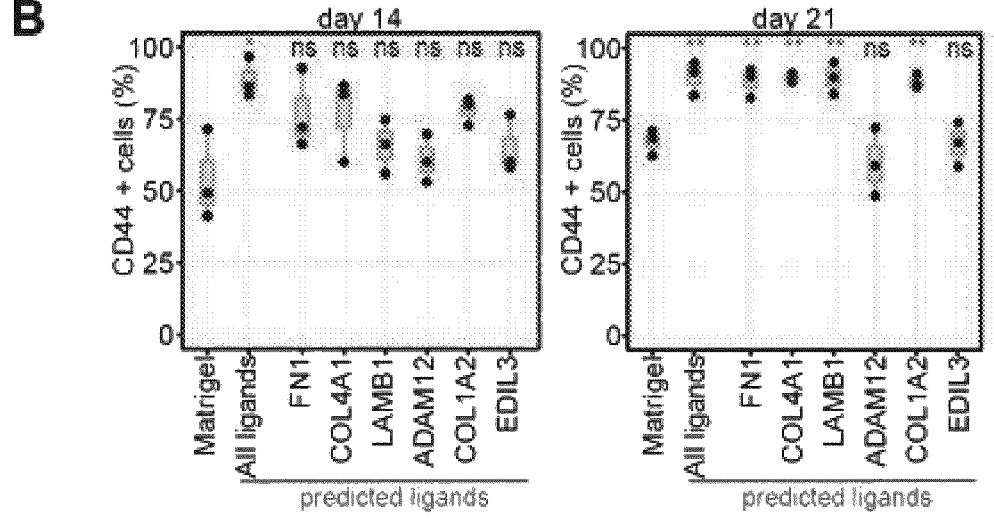
Figure 8:
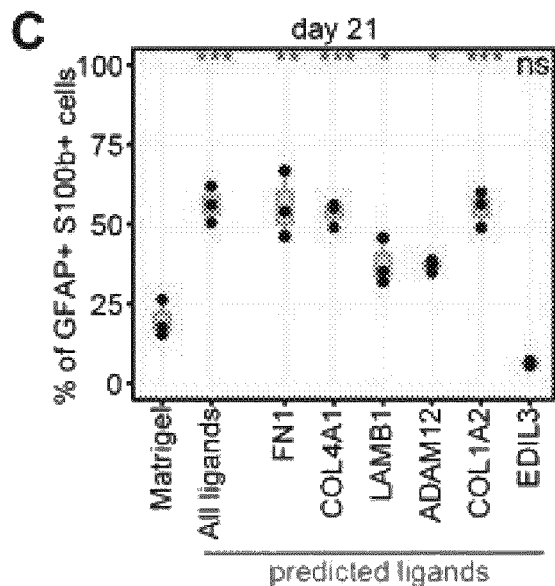
Figure 8:
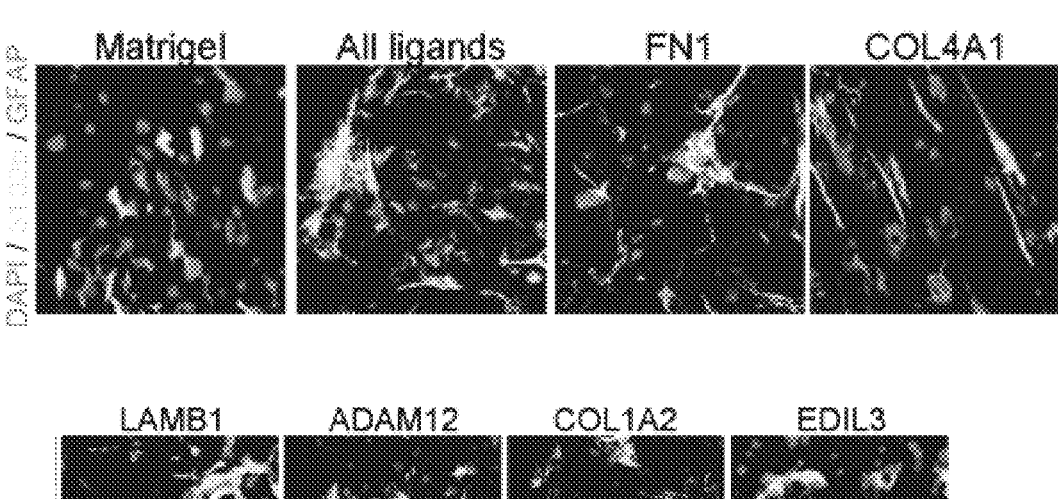
Figure 8:
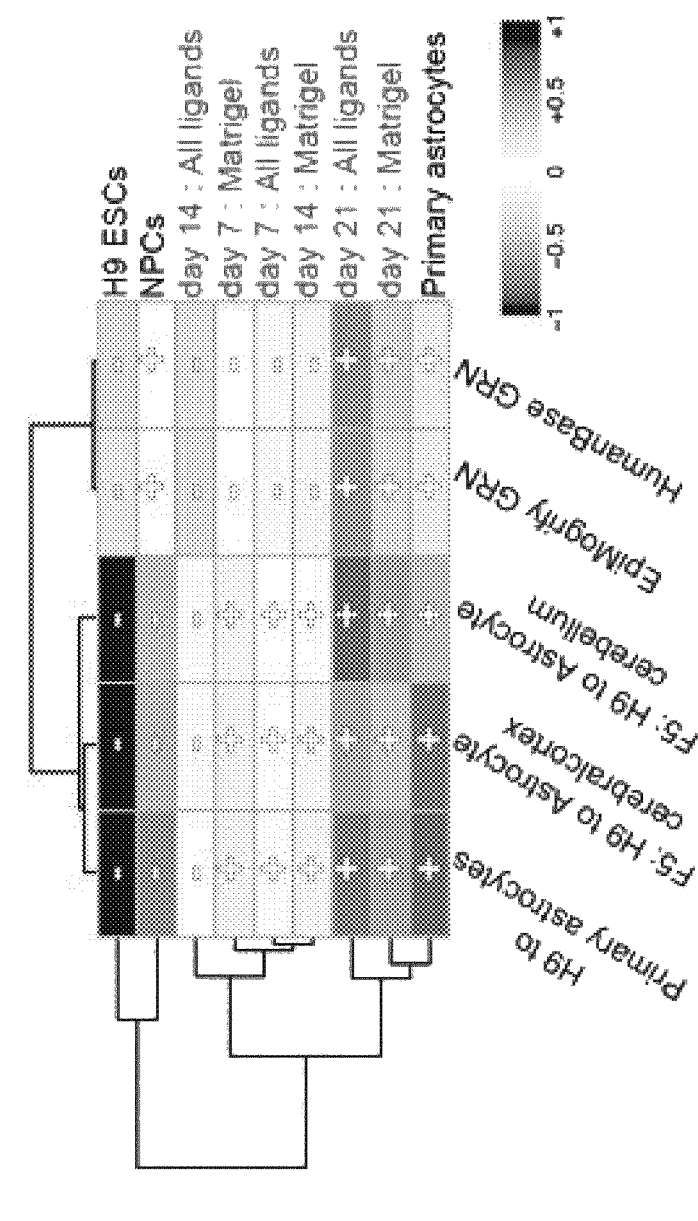

EpiMogrify predictions were assessed for astrocytic differentiation and identified factors such as FN1, COL4A1, LAMB1, COL1A2, EDIL3, ADAM12 and WNT5A. An astrocyte differentiation protocol was applied to H9 embryonic stem cells (FIG. 8A) and at day 35 of differentiation, a significant increase in cells positive for the astrocytic marker CD44 was observed in the "All ligand" condition (combination of all predicted factors). Subsequently at day 42, a significant increase in cells expressing CD44 was observed in H9 cells treated with FN1, COL4A1, LAMB1, COL1A2 and "All ligands" compared to the Matrigel control (FIG. 8B). Immunofluorescence was performed to obtain the percentage of DAPI+ cells with GFAP and S100b astrocytic markers in all conditions (FIG. 8D). Under predicted conditions, cultures also expressed the astrocytic markers S100b and GFAP at day 42 (FIG. 8C) suggesting that the predicted factors increase the efficiency of astrocyte differentiation.

For a group of genes that indicates astrocyte specificity (astrocytic transcriptional signatures), the mean z-score of the gene expression profile in TPM is calculated across three samples which were sequenced at each time-point and condition. The astrocytic transcriptional signatures are (i) significantly upregulated genes between H9 ESCs and primary astrocytes obtained from our RNA-seq data, (ii) significantly upregulated genes between H9 ESCs and astrocytes from cerebral cortex obtained from FANTOM5 (F5) database, (iii) significantly upregulated genes between H9 ESCs and astrocytes from cerebellum obtained from F5 database, (iv) EpiMogrify GRN (gene regulatory network) is a geneset containing primary astrocyte cell identity genes with a positive RegDBS score and the connected genes on the STRING network upto first neighbours that are regulated and (v) HumanBase GRN is an astrocyte-specific network obtained from HumanBase database (FIG. 8D).

Figure 9:
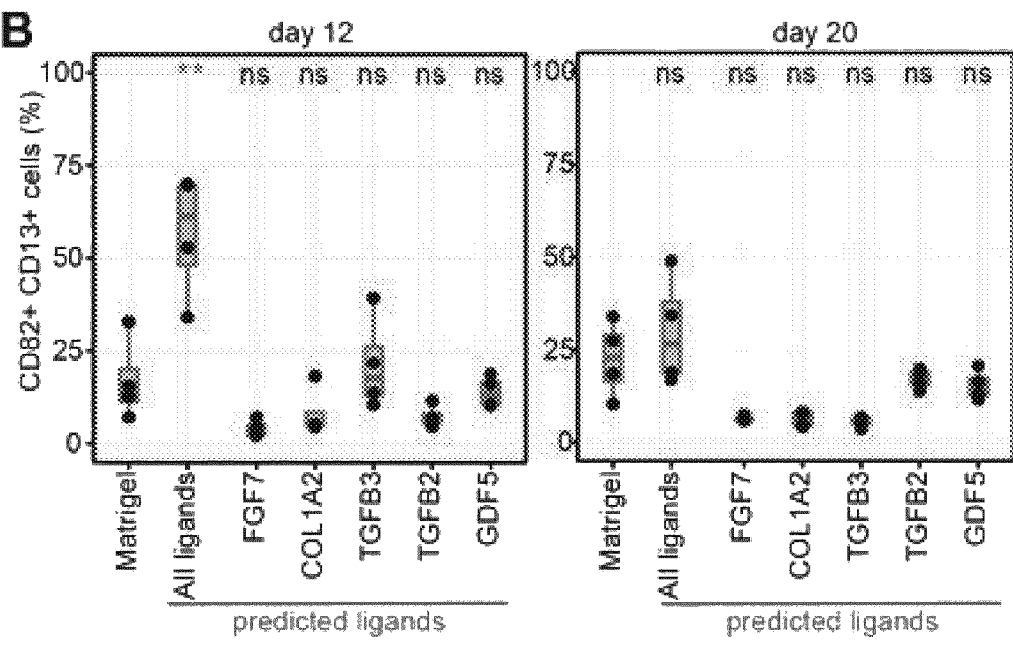
FIG. 9: Directed differentiation of cardiomyocytes in vitro. (A) Schematic diagram of cardiomyocytes in vitro differentiation from H9 embryonic stem cells (H9 ESCs). After 3 days, the H9 ESCs were seeded under different predicted conditions and positive control Matrigel only. Immunofluorescence (IF) and Fluorescence-activated cell sorting (FACS) were performed on day 12 and 20. (B) FACS for cardiac marker CD82+ and CD13+ cells for all the conditions. (C) IF was performed to obtain the percentage of DAPI+ area with cTnT cardiac markers. (D) IF of cTnT (Green) at day 21 in all conditions. Cells were counterstained with DAPI. Scale=25 µm. Unpaired one-tailed t-test was used to compare the predicted conditions with control. *P<0.05, **P<0.01 and ns not significant.
Figure 9:
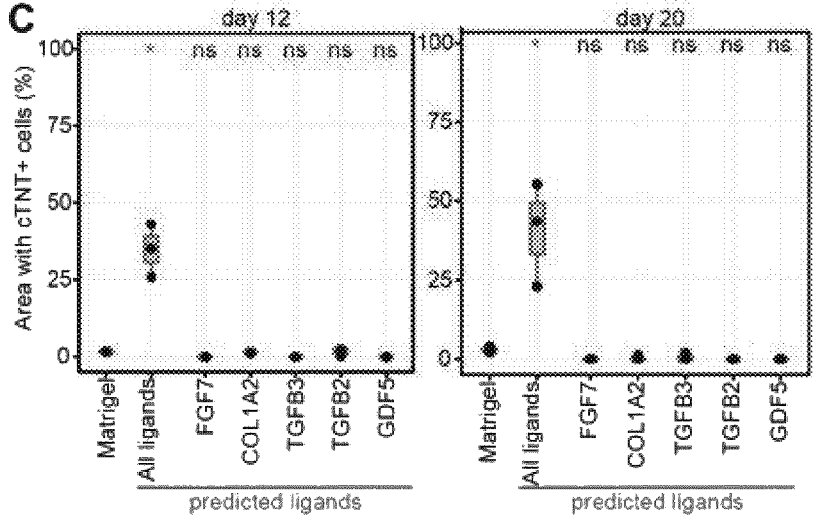
Figure 9:
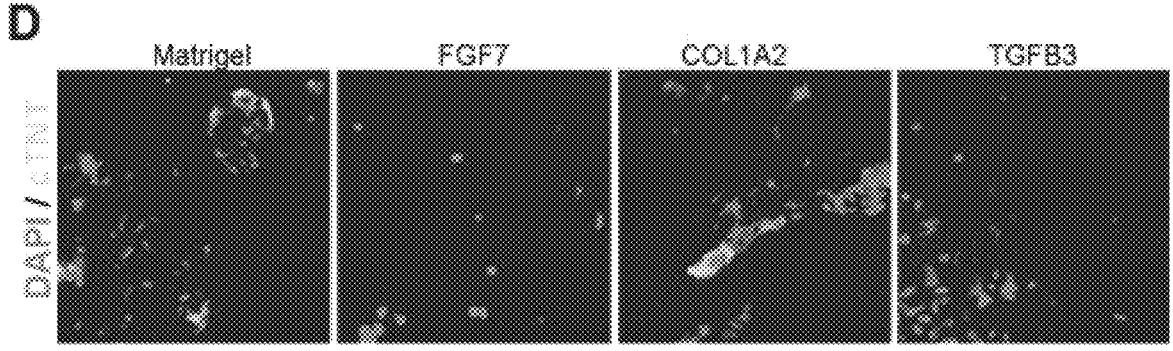
Figure 9:
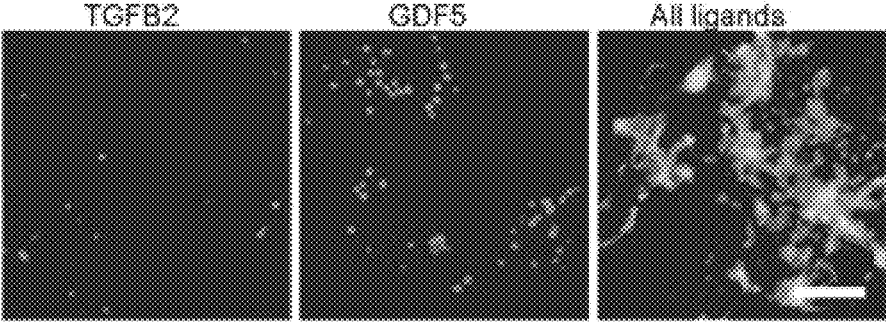

Example 10: EpiMogrify Predicts Factors for Cell Conversion, e.g., Cardiomyoctes Next EpiMogrify-predicted conversion conditions were tested for cardiomyocyte differentiation (FGF7 (Fibroblast Growth Factor 7), COL1A2 (Collagen I), TGFB3 (Transforming Growth Factor Beta 3), COL6A3 (Collagen VI), EFNA1 (Ephrin A1), TGFB2 (Transforming Growth Factor Beta 2) and GDFS (Growth Differentiation Factor 5)). To do this, the ligands were supplemented into culture media individually and together on H9 ESCs during differentiation (FIG. 9A), using Matrigel as a control. At day 12 of the differentiation, a significant increase in cells expressing early cardiac-lineage markers CD82 and CD13 in predicted conditions (FIG. 9B) was observed. By day 20, the remaining conditions also had resulted in cells expressing early cardiac-lineage marker expression, however the predicted conditions showed a significantly higher expression of the late cardiac marker, cTNT, at both day 12 and 20 compared to Matrigel control (FIGS. 9C, D). Moreover, the phenotype of differentiated cardiomyocytes was determined based on the potential for differentiated cells to beat, showing that there was a larger proportion of the plate with beating cells when using EpiMogrify-predicted conditions (all predicted factors combined) as compared with Matrigel. Taken together, these data show that there is an increase in cardiac differentiation efficiency, yielding a higher percentage of functional cardiomyocytes.

Example 11: Experimental Methods

Cell Count Assay $5 \times 10^3$ cells of ReN astrocytes and primary astrocytes were seeded onto 48-well plates in the respective conditions: no substrate, Matrigel, FN1 (Fibronectin) (Sigma Aldrich), COL4A1 (Collagen IV) (Sigma Aldrich), LAMB1 (Laminin221) (Biolamina), ADAM12 (Sigma Aldrich), COL1A2 (Collagen I) (Sigma Aldrich), EDIL3 (R&D Systems) and all ligands (combination of aforementioned substrates and growth factors without Matrigel). After 3 days, cells were dissociated using Trypsin/EDTA Solution (TE) (Gibco) and counted using an EVE automatic cell counter (NanoEnTek Inc.).

For primary cardiomyocytes, $5 \times 10^4$ cells/well were seeded onto 12-well plate in the respective conditions: no substrate, Geltrex, FN1 (Fibronectin), COL1A2 (Collagen I), TFPI (Tissue factor pathway inhibitor), ApoE (Apolipoprotein E), FGF7 (Fibroblast Growth Factor-7) and all ligands (combination of aforementioned substrates and ligands without Geltrex. After 72 hours, cells were dissociated using 0.04% Trypsin/0.03% EDTA (Promocell) and counted using LUNA-II™ Automated Cell Counter (Logos Biosystem, Inc.)

$5 \times 10^4$ cells/well were seeded onto 12-well plate in the respective conditions, for smooth muscle cells: no substrate, Geltrex, NID1 (Nidogen-1), COL1A1 (Collagen I), COL4A1 (Collagen 4), COL6A1 (Collagen 6), THBS1 (Thrombospondin 1), FGF10 (Fibroblast Growth Factor-10), FGF7 (Fibroblast Growth Factor-7) and all ligands (a combination of aforementioned substrates and ligands without Geltrex. For endothelial cells: no substrate, Geltrex, FN1 (Fibronectin), THBS1 (Thrombospondin 1), CTGF (Connective tissue growth factor) PDGFB (Platelet-Derived Growth Factor Subunit B), CYR61 (Cysteine-rich angiogenic inducer 61), BMP4 (Bone Morphogenetic Protein 4), BMP6 (Bone Morphogenetic Protein 6) and all ligands (a combination of aforementioned substrates and ligands without Geltrex. After 72 hours, cells were dissociated using TrypLE Express (Life Technologies) and counted using LUNA-II™ Automated Cell Counter (Logos Biosystem, Inc.)

BrdU Proliferation Assay $5 \times 10^3$ cells of ReN astrocytes and primary astrocytes were seeded onto a 96-well black plate with clear bottom (Corning). After 12 hours, BrdU-label was added onto wells according to manufacturer's recommendations (Cell Proliferation ELISA, BrdU (chemiluminescent), Roche). After 72 hours, cells were fixed and labelled with anti-BrdU antibody, followed by a substrate reaction and analyzed using a PHERAstar FSX microplate reader (BMG Labtech). For primary cardiomyocytes, BrdU Cell Proliferation Assay Kit (BioVision Inc.) was used according to the manufacturer's instruction. Briefly, indicated cells were seeded into a 96-well tissue culture treated plate (Costar) at $5 \times 10^3$ cells/well. After 72 hours, BrdU solution was added into each assay well and incubated at 37° C. for 3 hours. BrdU incorporated by proliferating cells was detected by an enzyme-linked immunosorbent assay.

For both smooth muscle and endothelial cells, BrdU Cell Proliferation Assay Kit (BioVision Inc.) was used according to the manufacturer's instruction. Briefly, indicated cells were seeded into a 96-well tissue culture treated plate (Costar) at $5 \times 10^3$ cells/well. After 72 hours, BrdU solution was added into each assay well and incubated at 37° C. for 4 hours. BrdU incorporated by proliferating cells was detected by an enzyme-linked immunosorbent assay.

Flow Cytometry

For differentiation experiments, cultures were dissociated using Accutase (Stem Cell Technologies) and pelleted at 400×g for 5 minutes. Cells were then resuspended in APC-Cy7 CD44 antibody (103028, Biolegend); or PE-Cy7 CD13 (56159, BD Biosciences) and PE CD82 (342104, Biolegend) in 2% Fetal Bovine Serum (FBS) (Gibco) and Phosphate Buffered Saline (PBS) (Gibco) and incubated for 15 minutes at 4° C. Cell suspension was washed with PBS and pelleted at 400×g for 5 minutes for analysis. Viability of cells was determined using 4',6-diamidino-2-phenylindole (DAPI) (Life Technologies). Samples were analyzed using an LSR IIa analyzer (BD Biosciences) using BD FACSDiva software (BD Bioscience).

For primary cardiomyocytes, smooth muscle cells and endothelial cells, cells were dissociated using 0.04% Trypsin/0.03% EDTA (Promocell) and pelleted at 300×g for 5 minutes. Cells were then fixed in suspension in 4% paraformaldehyde (PFA) at room temperature, washed twice in FACS buffer (1×PBS, 0.2% BSA), and permeabilized with 0.1% Triton X-100. The primary antibodies for cardiomyocytes were rabbit anti-human Nkx2.5 (Cell Signaling) and rabbit anti-human GATA-4 (Novus Biologicals). The primary antibodies used for smooth muscle cells and endothelial cells were mouse monoclonal to alpha smooth muscle Actin (Abcam) and rabbit polyclonal to Von Willebrand Factor (Abcam), respectively. Secondary antibodies used include Alexa Fluor 488 goat anti-rabbit (Life Technologies) and Alexa Fluor 647 goat anti-rabbit (Life technologies). Cells were stained with the primary antibodies for 30 min at room temperature. After washing twice, cells were incubated with the secondary antibody, washed twice and resuspended in the FACS buffer for flow cytometry analysis using a BD FACS-Fortessa instrument (BD Biosciences).

Immunofluorescence

Cultured cells were fixed in 4% PFA (Sigma Aldrich) in PBS for 10 minutes and then permeabilized in PBS containing 0.3% Triton X-100 (Sigma Aldrich). Cultures were then incubated with primary antibodies followed by secondary antibodies (see dilutions below). 4',6-diamidino-2-phenylindole (DAPI) (1:1000) (Life Technologies) was added to visualize cell nuclei. Images were taken with an inverted fluorescence microscope and attached camera (Nikon Eclipse Ti). Primary antibodies used in the study were: anti-S100b (6673, Sigma Aldrich, 1:200) anti-GFAP (ab7260, Abcam, 1:500), cTNT (MS-295-P1, Thermo Fisher, 1:100). Secondary antibodies used in the study (all 1:400) were Alexa Fluor488 donkey anti-mouse IgG (A21202, Life Technologies), Alexa Fluor 555 donkey anti-rabbit IgG (A31572, Life Technologies), Alexa Fluor 488 goat anti-mouse IgG (A28175, Life Technologies).

For endothelial cells and smooth muscle cells, the cultured cells were fixed in 4% PFA (Sigma Aldrich) in PBS for 10 minutes and then permeabilized in PBS containing 0.1% Triton X-100 (Sigma Aldrich). Cultures were then incubated with primary antibodies followed by secondary antibodies (see dilutions below). Hoechst 33342 (1:1000) (Life Technologies) was added to visualize cell nuclei. Images were taken with an inverted fluorescence microscope. Primary antibodies used for endothelial and smooth muscle cells were: anti-CD31 (Abcam, 1:200) and anti-Anti-TAGLN/Transgelin (Abcam, 1:200), respectively. Secondary antibodies used in the study (all 1:400) were Alexa Fluor 488 goat anti-mouse (Life Technologies) and Alexa Fluor 488 donkey anti-goat (Life technologies).

RNA-seq Library Preparation and Analysis

Total RNAs were isolated from 27 samples (H9 ESC, primary astrocytes and cells from day 7, 14 and 21 during astrocyte differentiation) using TRIzol™ Reagent (Thermo Fisher Scientific). 100-200 ng total RNAs with RIN of 8.5-10 were directed for RNA-seq library preparation using NEBNext Ultra II directional RNA library prep kit combined with poly A mRNA enrichment and NEBNext®

Multiplex Oligos for Illumina® (96 Unique Dual Index Primer Pairs) following the manufacturer's protocol. To remove excess primers and adaptor dimers, PCR products were purified twice using SPRI beads (Beckman Coulter). The quality of the libraries was assessed using Agilent Bioanalyzer DNA 1000 chip (Duke-NUS Genome Facility) and the molar concentration of each library was determined using KAPA library quantification kit (Roche). Three pooled libraries (each containing 9 samples with the pooled concentration of 8 nM in 30 uL) was sent for sequencing on Illumina HiSeq4000 (NovogeneAIT Genomics Singapore).

Gene expression analysis on the above RNA-seq data from H9 ESC, primary astrocyte and at different time-points (day 7, 14 and 21) during astrocyte differentiation and at conditions with control Matrigel and all ligands predicted by EpiMogrify. The sequencing reads were trimmed using Trimmomatic v0.39 and the reads were aligned using STAR v2.7.3 to the GRCh38 human genome. The gene expression profiles for the samples were generated using featureCounts v1.6.0 and the differential gene expression profile was computed using DESeq2 v1.26.0. To compare the gene expression profile of our RNA-seq data with astrocyte transcriptional signatures, the data was normalised using Transcripts Per Million (TPM) normalization. Next, 5,475 genes that were expressed (TPM>1) in primary astrocytes were selected and for these genes we calculated gene z-score across all samples (H9 ESC, primary astrocytes and differentiated astrocytes at different time-points and conditions). To obtain astrocytic transcriptional signatures, the differential gene expression profiles between H9 ESCs and astrocytes in cerebellum, and H9 and astrocytes in cerebral cortex was obtained from FANTOM5 gene expression atlas. The EpiMogrify GRN consists of astrocyte cell identity genes, which are genes with a positive RegDBS score and the genes that are directly connected to these cell identity genes on the STRING network. The HumanBase astrocyte-specific GRN was obtained from the database.

It will be understood that the invention disclosed and defined in this specification extends to all alternative combinations of two or more of the individual features mentioned or evident from the text or drawings. All of these different combinations constitute various alternative aspects of the invention.

Statements and Embodiments of the Invention i. A method of determining the cell identity genes for a cell of interest, the method comprising the steps of:

determining the differential breadth of H3K4me3 modified regions for each protein-coding gene in a cell of interest;

determining a network score for each protein-coding gene in the cell of interest based on the differential breadth of H3K4me3 modified regions and the interactions between the protein products of each protein-coding gene over at least one network, wherein the network contains information of the interactions between the products of the protein-coding gene;

determining a cell identity score for each protein-coding gene in the cell of interest based on a combination of the differential breadth and network score;

prioritising each protein-coding gene according to its cell identity score;

thereby identifying the cell identity genes for the cell of interest.

ii. The method of statement i wherein determining the differential breadth of H3K4me3 modified regions comprises determining a differential broadness score (DBS) for each protein-coding gene in a cell of interest, wherein the DBS is based on the difference in breadth of H3K4me3 modified regions for all protein-coding genes compared to the median breadth of the H3K4me3 modified regions for the same genes in a population of different cell types.

iii. The method of statement ii wherein determining the network score is based on the DBS and the interactions between the products of each protein-coding gene over the at least one network.

iv. A method of determining the factors required for maintaining a cell type in vitro, the method comprising the steps of:

determining a differential broadness score (DBS) for each protein-coding gene in a cell of interest wherein the DBS is based on the difference in breadth of H3K4me3 modified regions for all protein-coding genes compared to the median breadth of the H3K4me3 modified regions for the same protein-coding genes in a population of different cell types;

determining a network score for each protein-coding gene in the cell of interest based on the DBS and the interactions between the protein products of each protein-coding gene over at least one network, wherein the network contains information of the interactions between the product of each protein-coding gene and other protein-coding gene products in the cell;

determining a cell identity score (RegDBS) for each protein-coding gene in the cell of interest based on a combination of the DBS and network scores;

prioritising each protein-coding gene according to its RegDBS thereby identifying the cell identity genes for the cell of interest, wherein each cell identity gene encodes a factor associated with the cell identity of the cell of interest;

thereby identifying the factors required for maintaining the cell of interest in vitro.

v. The method of any one of statements i to iv wherein the differential breadth of the H3K4me3 modified regions is determined by:

obtaining information on the breadth of the H3K4me3 modified region for each protein-coding gene in the cell of interest to obtain a gene peak breadth score (B) for each protein-coding gene in the cell; and calculating the difference between the gene breadth score of each gene in the cell and the median gene breadth score for the same gene across a population of cells of different types, thereby determining a differential peak broadness score (DBS) for each protein-coding gene in the cell of interest.

vi. The method of any one of statements i to v wherein the breadth of the H3K4me3 modified region is determined based on ChIP-seq information, preferably wherein the information is obtained from the ENCODE database.

vii. The method of statement v or vi, wherein determining the gene peak breadth score (B) comprises firstly defining regions of the genome for which there is significant H3K4me3 modification and defining those regions as histone modification reference peak loci (RPL).

viii. The method of statement vii wherein the RPL are obtained by merging ChIP-seq peak regions obtained, across all cell types, preferably wherein the peak regions that are merged are overlapping peak regions.

ix. The method of any one of statements v to viii wherein the gene peak breadth score (B) for each protein-coding gene comprises excluding genes for which H3K4me3 and H3K27me3 modified regions are identified, wherein the genes are identified as poised genes.

x. The method of any one of statements i to ix wherein the H3K4me3 modification comprises H3K4me3 modification.

xi. The method of any one of statements ii to ix wherein determining the differential breadth of H3K4me3 modified regions (DBS) comprises combining information on the difference in breadth of the H3K4me3 modified region for each protein-coding gene with the significance of that difference in breadth.

xii. The method of statement xi wherein the DBS is determined by summing the difference in peak breadth with the significance of the difference, preferably, wherein the DBS is determined by summing difference in H3K4me3 peak breadth and the –log 10 P-value of the significance.

xiii. The method of any one of statements i to xii wherein determining the network score for each protein-coding gene in the cell of interest comprises combining information on the differential breadth of H3K4me3 modified regions (DBS) for each protein-coding gene, the number of outdegree nodes of the gene and the level of connection of the gene in the network.

xiv. The method of statement xiii wherein the network score is determined by summing the DBS of connected genes, weighted for the number of outdegree nodes of the gene and the level of connection to obtain a weighted sum of DBS for the connected protein-coding genes in the network.

xv. The method of any one of statements i to xiv wherein the protein-protein interaction network is the STRING database.

xvi. The method of any one of statements i to xv wherein the cell identity score (RegDBS) is an indicator of the regulatory influence of each protein-coding gene on the identity of the cell.

xvii. The method of any one of statements i to xvi wherein determining the cell identity score (RegDBS) comprises preferentially weighting protein-coding genes which encode regulatory factors.

xviii. The method of any one of statements i to xvii wherein determining the cell identity score (RegDBS) for each protein-coding gene comprises summing the differential breadth of H3K4me3 modified regions (DBS) score with the normalised network score across all genes in the cell of interest.

xix. The method of statement xviii wherein summing of the DBS and network score comprises weighting the DBS relative to the network score by a factor of 2:1.

xx. The method of any one of statements i to xix wherein the step of prioritising each protein-coding gene according to its cell identity score (RegDBS) comprises ordering the genes based on the RegDBS value.

xxi. The method of any one of statements i to xx wherein the factors for maintaining the cell of interest in vitro are selected from the group consisting of: receptor-ligand pairs involved in cell signalling, preferably the ligands of the receptor-ligand pairs, transcription factors, and epigenetic remodelling factors.

xxii. The method of any one of statements i to xxi wherein the method comprises selecting the cell identity genes which encode receptor-ligand pairs involved in cell signalling, thereby identifying signalling molecules required for maintaining the cell of interest in vitro.

xxiii. The method of statement xxii wherein each protein-coding gene that encodes a cell surface receptor is ranked according to its RegDBS score and each ligands associated with the receptors is ranked according to its DBS score to obtain a combined ranking of receptors and ligands and wherein the combined ranking identifies the ligands for use in supplementing culture media for maintaining the cell of interest in vitro.

xxiv. The method of any one of statements i to xxi wherein the method further comprises selecting the cell identity genes which encode transcription factors thereby identifying the transcription factors required for maintaining the cell of interest in vitro.

xxv. A method of determining the cell identity genes for a cell of interest, the method comprising the steps of:

determining a H3K4me3 gene peak breadth score (B) for each protein-coding gene (g) in a cell of interest (x), wherein the gene peak breadth score is the sum of the length of the regions in the promoter of each protein-coding gene comprising H3K4me3 modifications;

determining the normalised difference in gene peak breadth score ($\Delta peakbreadth^x_g$) between the cell of interest and the median gene peak breadth score of a population of cells representative of background gene peak breadth scores, and the significance of that difference (Pval);

determining a differential broadness score ($DBS^x_g$) for each protein-coding gene in the cell by summing the $\Delta peakbreadth$ and P val values;

determining a network score (Netxg) for each protein-coding gene in the cell of interest by combining information on the differential broadness score ($DBS^x_g$) of connected genes (r) in a network, wherein the network contains information of the interactions between the product of each protein-coding gene and other protein-coding gene products in the cell; wherein the differential broadness score is corrected for the number of outdegree nodes of the gene (O) and the level of connection of the gene (L); wherein preferably the weighted sum of the differential broadness scores ($DBS^x_g$) is calculated up to the third level of connection;

normalising the network score $Net^x_g$ across all protein-coding genes (G) in the cell of interest (x);

determining a regulatory differential broadness score ($RegDBS^x_g$) for each protein-coding gene in the cell of interest by scoring each protein-coding gene in the cell of interest based on a combination of the differential broadness score ($DBS^x_g$) and network scores ($Net^x_g$), wherein the $RegDBS^x_g$ is an indicator of the regulatory influence of each protein-coding gene on the identity of the cell;

prioritising each gene according to its $RegDBS^x_g$ thereby identifying the cell identity genes for the cell of interest.

xxvi. The method of any one of statements i to xxv wherein interactions between nodes of the protein-encoding gene products are selected for inclusion in the calculation of the network score if the experimental score in the protein-protein network is greater than zero and the combined score is greater than 500.

xxvii. The method of any one of statements i to xxvi wherein determining the network score comprises removing protein-coding genes with no associated peak H3K4me3 breadth from the protein-protein interaction network.

xxviii. A method of determining the factors required for conversion of a source cell to a cell exhibiting at least one characteristic of a target cell type, the method comprising the steps of:

determining the differential breadth of H3K4me3 modified regions for each protein-coding gene in a source cell and a target cell type to obtain a score of the H3K4me3 modification for each protein-coding gene (DBS) in the source and target cell type;

calculating the difference between the DBS of the source cell and the DBS of the target cell to obtain a measure of the difference in H3K4me3 modification (cell conversion ΔDBS) between the source and target cell for each protein-coding gene;

determining a network score for conversion from the source cell type to the target cell type based on the cell conversion ΔDBS and the interactions between the protein products of each protein-coding gene over at least one network, wherein the network contains information of the interactions between each protein-coding gene product and other gene products in a cell;

determining a cell identity conversion score for each protein-coding gene in the target cell based on a combination of the cell conversion ΔDBS and network score;

prioritising each protein-coding gene according to its cell identity conversion score to identify the cell identity genes for the target cell, wherein each cell identity gene encodes a factor associated with the cell identity of the target cell;

thereby determining the factors required for conversion of a source cell to a cell exhibiting at least one characteristic of a target cell type.

xxix. A method of determining the factors required for conversion of a source cell to a cell exhibiting at least one characteristic of a target cell type, the method comprising the steps of:

determining a differential broadness score (DBS) for each protein-coding gene in a source cell and in a target cell, wherein the DBS is based on the difference in breadth of H3K4me3 modified regions for all protein-coding genes compared to the median breadth of the H3K4me3 modified regions for the same protein-coding genes in a population of different cell types;

calculating the difference between the DBS of the source cell and the DBS of the target cell to obtain a cell conversion ΔDBS for each protein-coding gene;

determining a network score for cell conversion from the source cell type to the target cell type, based on the cell conversion ΔDBS and the interactions between the protein products of each gene over at least one network, wherein the network contains information of the interactions between the product of each protein-coding gene and other protein-coding gene products in the cell;

determining a cell identity conversion score (RegΔDBS) for each protein-coding gene in the target cell based on a combination of the cell conversion ΔDBS and network score prioritising each protein-coding gene according to its cell conversion RegΔDBS to identify the cell identity genes for the target cell wherein each cell identity gene encodes a factor associated with the cell identity of the target cell;

thereby determining the factors required for conversion of a source cell to a cell exhibiting at least one characteristic of a target cell type.

xxx. The method of any one of statements xxviii to xxix wherein the differential breadth of the H3K4me3 modified regions is determined by:

obtaining information on the breadth of the H3K4me3 modified region for each protein-coding gene in the source cell and the target cell to obtain a gene peak breadth score (B) for each gene in each cell type; and calculating the difference between the gene peak breadth score of each protein-coding gene in the cell type and the median gene peak breadth score for the same gene across a population of cells of different types, thereby determining a differential broadness score (DBS) for each gene in both the source and target cells.

xxxi. The method of any one of statements xxvii to xxx wherein the breadth of the H3K4me3 modified region is determined based on ChIP-seq information, preferably wherein the information is obtained from the ENCODE database.

xxxii. The method of any one of statements xxx to xxxi wherein determining the gene peak breadth score (B) comprises firstly defining regions of the genome for which there is significant H3K4me3 modification (histone modification reference peak loci, or RPL).

xxxiii. The method of statement xxxii wherein the RPL are obtained by merging ChIP-seq peak regions obtained, across all cell types, preferably wherein the peak regions are overlapping peak regions.

xxxiv. The method of any one of statements xxx to xxxiii wherein determining the gene peak breadth score (B) for each protein-coding gene comprises excluding genes for which H3K4me3 and H3K27me3 modified regions are identified, wherein the genes are identified as poised genes.

xxxv. The method of any one of statements xxviii to xxxiv wherein the H3K4me3 modification comprises H3K4me3 modification.

xxxvi. The method of any one of statements xxviii to xxxv wherein determining the DBS for each protein-coding gene in the source cell and the target cell comprises combining information on the difference in H3K4me3 breadth for each protein-coding gene with the significance of that difference.

xxxvii. The method of statement xxxvi wherein determining the DBS comprises multiplying, normalising or summing the difference in peak breadth and the significance of the difference, preferably wherein the DBS is determined by summing the difference in peak breadth with the significance of the difference.

xxxviii. The method of any one of statements xxviii to xxxvii wherein calculating the difference between the DBS of the source cell and the DBS of the target cell to obtain a cell conversion ΔDBS for each gene comprises subtracting the source cell DBS for each protein-coding gene from the target cell DBS for each gene to obtain a cell conversion ΔDBS for each gene, wherein the cell conversion ΔDBS for each protein-coding gene provides a measure of the difference in the breadth of the H3K4me3 modified region for a given protein-coding gene between the source cell and the target cell.

xxxix. The method of any one of statements xxviii to xxxviii wherein the network score for cell conversion from a source cell to a target cell is the weighted combination of the cell conversion ΔDBS of the connected genes in the network.

xxxx. The method of statement xxxix wherein determining the network score for cell conversion comprises combining information on the cell conversion ΔDBS for each gene, the number of outdegree nodes of the gene and the level of connection of the gene in the network.

xli. The method of statement xl wherein the network score is determined by summing the cell conversion ΔDBS of connected genes, weighted for the number of outdegree nodes of the gene and the level of connection to obtain a weighted sum of cell conversion ΔDBS for the connected genes in the network.

xlii. The method of any one of statements xxviii to xli wherein the protein-protein interaction network is the STRING database.

xliii. The method of any one of statements xxviii to xlii wherein determining the cell conversion RegΔDBS comprises preferentially weighting protein-coding genes which encode regulatory factors.

xliv. The method of any one of statements xxviii to xlii wherein determining the cell conversion RegΔDBS for each protein-coding gene comprises summing the cell conversion ΔDBS score with the normalised cell conversion network score across all protein-coding genes.

xlv. The method of statement xliv wherein the summing of the cell conversion ΔDBS and cell conversion network score further comprises weighting the cell conversion ΔDBS relative to the cell conversion network score by a factor of 2:1.

xlvi. The method of any one of statements xxviii to xlv wherein prioritising each protein-coding gene according to its cell conversion RegΔDBS comprises ordering the genes based on the cell conversion RegΔDBS value.

xlvii. The method of any one of statements xxviii to xlvi wherein the cell conversion factors are selected from the group consisting of receptor-ligand pairs, transcription factors, or epigenetic remodelling factors.

xlviii. The method of any one of statements xxviii to xlvii wherein the method further comprises selecting the subset of factors that are transcription factors thereby identifying the transcription factors required for conversion of a source cell to a cell exhibiting at least one characteristic of a target cell type, preferably wherein the conversion is transdifferentiation of a differentiated source cell to a differentiated target cell.

xlix. The method of any one of statements xxviii to xlvii wherein the method comprises selecting the subset of factors that are receptor-ligand pairs involved in cell signalling, thereby identifying the signalling molecules required for conversion of a source cell to a target cell, preferably wherein the factors identified are for directed differentiation of a pluripotent source cell to a differentiated target cell.

l. The method of statement xlix wherein each protein-coding gene that encodes a cell surface receptor is ranked according to its RegDBS score and each ligand associated with the receptors is ranked according to its DBS score to obtain a combined ranking of receptors and ligands and wherein the combined ranking identifies the ligands for use in supplementing culture media for maintaining the cell of interest in vitro.

li. A method of determining the factors required for conversion of a source cell to a cell exhibiting at least one characteristic of a target cell type, the method comprising the steps of:

determining a H3K4me3 gene peak breadth score (B) for each protein-coding gene (g) in a source cell interest (S), and in a target cell (T) wherein the gene breadth score is the sum of the length of the regions in the promoter of each protein-coding gene comprising H3K4me3 modifications;

determining the normalised difference in gene peak breadth score ($\Delta$peakbreadth$^S_g$) between the source cell and the median gene peak breadth score of a population of cells representative of background gene peak breadth scores, and the significance of that difference (Pval$^S_g$);

determining the normalised difference in gene peak breadth score ($\Delta$peakbreadth$^T_g$) between the target cell and the median gene breadth score of a population of cells representative of background gene peak breadth scores, and the significance of that difference (Pval$^S_g$);

summing the $\Delta$peakbreadth$^S_g$ and Pval$^T_g$ values to obtain a differential broadness score (DBS$^S_g$) for each protein-coding gene in the source cell;

summing the $\Delta$peakbreadth$^T_g$ and Pval$^T_g$ values to obtain a differential broadness score (DBS$^T_g$) for each protein-coding gene in the target cell;

subtracting the differential broadness score (DBS$^S_g$) for each protein-coding gene in the source cell from the differential broadness score (DBS$^T_g$) for the same gene in the target cell to obtain a cell conversion ΔDBS ($\Delta$DBS$^{T-S}_g$) for each protein-coding gene in the target cell;

determining a network score (Net$^{T-S}_g$) for each gene in the target cell by combining the cell conversion differential broadness score ($\Delta$DBS$^{T-S}_g$) of connected genes (r) in a network, wherein the network contains information of the interactions between the products of each protein-coding gene in the cell; wherein the differential broadness score is corrected for the number of outdegree nodes of the gene (O) and the level of connection of the gene (L); wherein preferably the weighted sum of the cell conversion differential broadness scores ($\Delta$DBS$^{T-S}_g$) is calculated up to the third level of connection;

normalising the cell conversion network score Net$^{T-S}_g$ across all protein-coding genes;

scoring each protein-coding gene based on a combination of the cell conversion differential broadness score ($\Delta$DBS$^{T-S}_g$) and cell conversion network scores (Net$^{T-S}_g$), thereby determining a cell conversion regulatory differential broadness score (RegΔDBS$^{T-S}_g$) for each protein-coding gene; wherein the RegΔDBS$^{T-S}_g$ is an indicator of the difference in the regulatory influence of each protein-coding gene on the target cell compared to the source cell;

prioritising each protein-coding gene according to its cell identity score, RegΔDBS$^{T-S}_g$ cell to identify the cell identity genes for the target cell, wherein each cell identity gene encodes a factor associated with the cell identity of the target cell;

thereby identifying the factors required for conversion of a source cell to a cell exhibiting at least one characteristic of a target cell type.

lii. The method of any one of statements xxviii to li wherein the interactions between nodes of the protein-encoding gene products in the protein-protein interaction network are selected if the experimental score in the network is greater than zero and the combined score is greater than 500.

liii. The method of any one of statements xxviii to lii wherein determining the network score comprises removing genes with no associated peak H3K4me3 breadth from the protein-protein interaction network.

liv. The method of statement xlviii further comprising the step of removing transcriptionally redundant TFs from the ranked lists from each cell type.

lv. A method of maintaining a population of cells in vitro, the method comprising:

providing a population of a cell of interest in a cell culture;

determining a differential broadness score (DBS) for each protein-coding gene in the cell of interest wherein the DBS is based on the difference in breadth of H3K4me3 modified regions for all protein-coding genes compared to the median breadth of the H3K4me3 modified regions for the same genes in a population of different cell types;

determining a network score for each protein-coding gene in the cell of interest based on the DBS and the interactions between the protein products of each gene over at least one network, wherein the network contains information of the interactions between the product of each protein-coding gene and other protein-coding gene products in the cell;

scoring each protein-coding gene in the cell of interest based on a combination of the DBS and network scores, thereby determining a RegDBS for each protein-coding gene in the cell of interest; wherein the RegDBS is an indicator of the importance of each protein-coding gene for cell identity;

prioritising each protein-coding gene according to its RegDBS thereby identifying the cell identity genes for the cell of interest, wherein each cell identity gene encodes a factor associated with the cell identity of the cell of interest;

contacting the population of the cell of interest with one or more of the factors associated with the cell identity of the cell of interest;

culturing the population of cells for a sufficient time and under conditions to allow for the maintenance of the cell of interest in the cell culture thereby maintaining a population of cells in vitro.

lvi. A method of maintaining a population of astrocytes in vitro, the method comprising the following steps in order:

providing a population of astrocytes in a cell culture;

contacting the population of astrocytes with one or more factors for maintaining at least one characteristic of an astrocyte, culturing the population of astrocytes for a sufficient time and under conditions to allow for the maintenance of the astrocytes in the cell culture;

wherein the factors are selected from: FN1, COL4A1, EDIL3, WNT5A, LAMB1, ADAM12 and COL1A2, thereby maintaining the population of astrocytes in vitro.

lvii. The method of statement lvi wherein the factors comprise, consist or consist essentially of: FN1, COL4A1, EDIL3, WNT5A, LAMB1, ADAM12 and COL1A2.

lviii. The method of statement lvi or lvii wherein the method comprises contacting the astrocytes with 1 or more of, 2 or more of, 3 or more of, 4 of more of, 5 or more of, FN1, COL4A1, EDIL3, WNT5A, LAMB1, ADAM12 and COL1A2.

lix. The method of any one of statements lvi to lix wherein the method further comprises the step of administering the astrocytes to an individual.

lx. A method of maintaining a population of cardiomyocytes in vitro, the method comprising:

providing a population of cardiomyocytes in a cell culture;

contacting the population of cardiomyocytes with one or more factors for maintaining at least one characteristic of a cardiomyocytes, culturing the population of cardiomyocytes for a sufficient time and in conditions suitable for maintaining the cardiomyocytes in the cell culture;

wherein the factors are selected from: FN1, COL3A1, TFPI, FGF7, APOE, C3, COL1A2, SERPINE1, COL6A3 and CXCL12;

thereby maintaining the population of cardiomyocytes in vitro.

lxi. The method of statement lx wherein the factors comprise, consist or consist essentially of: FN1, COL3A1, TFPI, FGF7, APOE, C3, COL1A2, SERPINE1, COL6A3 and CXCL12.

lxii. The method of statement lx or lxi wherein the method comprises contacting the cardiomyocytes with one or more of FN1, COL3A1, TFPI, FGF7, APOE, C3, COL1A2, SERPINE1, COL6A3 and CXCL12, optionally 2 or more of, 3 or more of, 4 of more of, 5 or more of, or 6 or more of FN1, COL3A1, TFPI, FGF7, APOE, C3, COL1A2, SERPINE1, COL6A3, CXCL12; preferably wherein the factors are FN1, COL3A1, TFP1, FGF7 and APOE.

lxiii. The method of any one of statements lx to lxii wherein the method further includes the step of administering the cardiomyocytes, or cell population to an individual.

lxiv. A method of conversion of a source cell to a cell exhibiting at least one characteristic of a target cell type, the method comprising the steps of:

providing a source cell;

determining the differential breadth of H3K4me3 modified regions for each protein-coding gene in a source cell and a target cell type to obtain a score of the H3K4me3 modification for each protein-coding gene (DBS) in the source and target cell type;

calculating the difference between the DBS of the source cell and the DBS of the target cell to obtain a measure of the difference in H3K4me3 modification (cell conversion ΔDBS) between the source and target cell for each protein-coding gene;

determining a network score for conversion from the source cell type to the target cell type based on the cell conversion ΔDBS and the interactions between the protein products of each protein-coding gene over at least one network, wherein the network contains information of the interactions between each protein-coding gene product and other gene products in a cell;

determining a cell identity conversion score for each protein-coding gene in the target cell based on a combination of the cell conversion ΔDBS and network score;

prioritising each protein-coding gene according to its cell identity conversion score to identify the cell identity genes for the target cell, wherein each cell identity gene encodes a factor associated with the cell identity of the target cell;

culturing the source cell for a sufficient time and under conditions to allow conversion of the source cell to a cell exhibiting at least one characteristic of a target cell type;

thereby converting a source cell to a cell exhibiting at least one characteristic of a target cell type, optionally, wherein increasing the amount of the one or more factors comprises i) contacting the source cell with factor or an agent which increases expression of the factor by the cell; or ii) transfecting the source cell with a nucleic acid that encodes the factor and expressing the nucleic acid in the cell.

lxv. A method for differentiation of a source cell, the method comprising increasing the protein expression of one or more factors, or variant thereof, in the source cell, wherein the source cell is differentiated to exhibit at least one characteristic of a target cell, wherein:

the source cell is a pluripotent stem cell and the target cell is an astrocyte; and the factors are one or more of: FN1, COL4A1, COL1A2, EDIL3, ADAM12, LAMB1 and WNT5A.

lxvi. A method of generating a cell exhibiting at least one characteristic of an astrocyte from a pluripotent stem cell or neural progenitor cell, the method comprising:

contacting a pluripotent stem cell or neural progenitor cell with one or more of the factors FN1, COL4A1, COL1A2, EDIL3, ADAM12, LAMB1 and WNT5A, or variant thereof, in the source cell; and culturing the pluripotent stem cell or neural progenitor cell for a sufficient time and under conditions to allow differentiation to an astrocyte; thereby generating the cell exhibiting at least one characteristic of an astrocyte from a pluripotent stem cell or neural progenitor cell.

lxvii. A method for differentiation of a pluripotent stem cell, preferably an embryonic stem cell or neural progenitor cell, to a cell that exhibits at least one characteristic of an astrocyte comprising: i) providing a pluripotent stem cell, or a cell population comprising a pluripotent stem cell or or neural progenitor cell; ii) transfecting said pluripotent stem cell or neural progenitor cell with one or more nucleic acids comprising a nucleotide sequence that encodes one or more factors important for astrocyte cell identity; and iii) culturing said cell or cell population, and optionally monitoring the cell or cell population for at least one characteristic of the astrocyte cell, wherein:

the factors for differentiating a pluripotent stem cell to an astrocyte, or the factors for generating a cell exhibiting at least one characteristic of an astrocyte comprise, consist or consist essentially of: FN1, COL4A1, COL1A2, EDIL3, ADAM12, LAMB1 and WNT5A.

lxviii. A method of generating a cell exhibiting at least one characteristic of an astrocyte from an embryonic stem cell or neural progenitor cell, the method comprising:

increasing the amount of any one or more of FN1, COL4A1, COL1A2, EDIL3, ADAM12, LAMB1 and WNT5A or variant thereof, in the embryonic stem cell or neural progenitor cell; and culturing the embryonic stem cell for a sufficient time and under conditions for differentiation into an astrocyte; thereby generating the cell exhibiting at least one characteristic of an astrocyte from an embryonic stem cell or neural progenitor cell.

lxix. The method of statement lxviii wherein increasing the amount of one or more of the factors comprises expressing a nucleic acid encoding one or more of the factors in the source cell.

lxx. The method of any one of statements lxiv to lxix wherein the at least one characteristic of the astrocyte is up-regulation of any one or more astrocyte markers and/or change in cell morphology, preferably wherein the astrocyte markers are selected from: GFAP, S100B, ALDH1L1, CD44 and GLAST1.

The invention claimed is:

1. A method for maintaining a cell in vitro, the method comprising the steps of:

providing a cell of interest in cell culture;

determining differential breadth of histone 3 trimethylated at lysine 4 (H3K4me3) modified regions for each protein-coding gene in said cell;

determining a differential broadness score (DBS) for each protein-coding gene in said cell;

determining a network score for each protein-coding gene in said cell based on the DBS and interactions between the protein products of each protein-coding gene over at least one network, determining a cell identity score (RegDBS) for each protein-coding gene in said cell based on a combination of the DBS and network scores;

prioritising each protein-coding gene according to its RegDBS thereby identifying cell identity genes for said cell, wherein each cell identity gene encodes a factor associated with cell identity of the cell of interest;

contacting said cell of interest with one or more of the factors associated with the cell identity of said cell;

culturing said cell of interest for a sufficient time and under conditions to allow for maintenance of said cell in cell culture;

thereby maintaining the cell of interest in vitro.

2. The method of claim 1, wherein the cell of interest is a differentiated cell, differentiating cell, undifferentiated cell or transdifferentiated cell.

3. The method of claim 1, wherein the cell of interest is a population of cells or a tissue.

4. The method of claim 1, wherein the cell of interest is selected from a cell derived from the ectoderm, mesoderm and endoderm germ layers.

5. The method of claim 1, wherein the differential breadth of the H3K4me3 modified regions is determined by:

obtaining information on the breadth of the H3K4me3 modified region for each protein-coding gene in the cell of interest to obtain a gene peak breadth score (B) for each protein-coding gene in the cell; and calculating the difference between the gene peak breadth score of each gene in the cell and the average gene peak breadth score for the same gene across a population of cells of different types, thereby determining a differential broadness score (DBS) for each protein-coding gene in the cell of interest.

6. The method of claim 5, wherein determining the gene peak breadth score (B) comprises firstly defining regions of the genome for which there is significant H3K4me3 modification and defining those regions as histone modification reference peak loci (RPL).

7. The method of claim 6, wherein the RPL are obtained by merging ChIP-seq peak regions obtained, across all cell types, wherein the peak regions that are merged are overlapping peak regions.

8. The method of claim 5, wherein the gene peak breadth score (B) for each protein-coding gene comprises excluding genes for which H3K4me3 and H3K27me3 modified regions are identified, wherein the genes are identified as poised genes.

9. The method of claim 1, wherein determining the cell identity score (RegDBS) comprises prioritizing protein-coding genes which encode regulatory factors.

10. The method of claim 1, wherein the factors for maintaining the cell of interest in vitro are selected from the group consisting of: receptor-ligand pairs involved in cell signalling, preferably the ligands of the receptor-ligand pairs, transcription factors, and epigenetic remodelling factors.

11. The method of claim 1, wherein the method comprises selecting the cell identity genes which encode receptor-ligand pairs involved in cell signalling, thereby identifying signalling molecules required for maintaining the cell of interest in vitro.

12. The method of claim 11, wherein each protein-coding gene that encodes a cell surface receptor is ranked according to its RegDBS score and each ligand associated with the receptor is ranked according to its DBS score, to obtain a combined ranking of receptors and ligands and wherein the combined ranking identifies the ligands for use in supplementing culture media for maintaining the cell of interest in vitro.

13. The method of claim 11, wherein the cell identity genes encode receptor-ligand pairs involved in cell signalling pathways.

14. The method of claim 1, wherein the method further comprises selecting the cell identity genes which encode transcription factors thereby identifying the transcription factors required for maintaining the cell of interest in vitro.

15. The method of claim 1, wherein determining the network score comprises removing protein-coding genes with no associated peak H3K4me3 breadth from the protein-protein interaction network.

16. The method of claim 13, wherein the cell identity genes encode receptor-ligand pairs involved in cell signalling pathways selected from: signalling by WNT, NOTCH, Hegdehog, Hippo, GPCR, Integrins, TGFB family (BMP, Activin, TGFB receptor), receptor tyrosine kinases (such as EGFR, FGFR, VEGF, PDGF, MET, MST, SCF-KIT, Insulin receptors, ERBB2, NTRKs), non-receptor tyrosine kinases (PTK6), MTOR, and Retinoic acid.

17. A method comprising:

(i) maintaining a cell in vitro, by performing a method comprising the steps of:

providing a cell of interest in cell culture;

determining differential breadth of histone 3 trimethylated at lysine 4 (H3K4me3) modified regions for each protein-coding gene in said cell;

determining a differential broadness score (DBS) for each protein-coding gene in said cell;

determining a network score for each protein-coding gene in said cell based on the DBS and interactions between the protein products of each protein-coding gene over at least one network, determining a cell identity score (RegDBS) for each protein-coding gene in said cell based on a combination of the DBS and network scores;

prioritising each protein-coding gene according to its RegDBS thereby identifying cell identity genes for said cell, wherein each cell identity gene encodes a factor associated with cell identity of the cell of interest;

contacting said cell of interest with one or more of the factors associated with the cell identity of said cell;

culturing said cell of interest for a sufficient time and under conditions to allow for maintenance of said cell in cell culture;

thereby maintaining the cell of interest in vitro; and (ii) administering the cell of interest to an individual, or administering a population of cells, wherein at least 5% of cells exhibit at least one characteristic of the cell of interest and those cells are produced by a method according to (i), to an individual.

\*   \*   \*   \*   \*